US012648603B2

(12) United States Patent
Suzuki et al.

(10) Patent No.:  US 12,648,603 B2
(45) Date of Patent:  Jun. 9, 2026

(54) FACE SHIELD AND MASK-EQUIPPED FACE SHIELD

(71) Applicant: DEXERIALS CORPORATION, Tochigi (JP)

(72) Inventors: Shinya Suzuki, Tochigi (JP); Chihiro Nishikawa, Tochigi (JP)

(73) Assignee: DEXERIALS CORPORATION, Tochigi (JP)

( * ) Notice: Subject to any disclaimer, the term of this patent is extended or adjusted under 35 U.S.C. 154(b) by 461 days.

(21) Appl. No.: 17/915,379

(22) PCT Filed: Apr. 23, 2021

(86) PCT No.: PCT/JP2021/016416
§ 371 (c)(1),
(2) Date: Sep. 28, 2022

(87) PCT Pub. No.: WO2021/220953
PCT Pub. Date: Nov. 4, 2021

(65) Prior Publication Data
US 2023/0132244 A1     Apr. 27, 2023

(30) Foreign Application Priority Data

May 1, 2020     (JP) ................................. 2020-081005
Jun. 26, 2020     (JP) ................................. 2020-110720

(51) Int. Cl.
*A41D 13/11*          (2006.01)
*A61F 9/04*          (2006.01)
(Continued)

(52) U.S. Cl.
CPC .......... *A41D 13/1184* (2013.01); *A61F 9/045* (2013.01); *A62B 18/082* (2013.01);
(Continued)

(58) Field of Classification Search
CPC .......... A61F 9/029; A61F 9/045; A61F 9/027; A41D 13/1184; A62B 18/02; A62B 18/082; A61B 90/05
See application file for complete search history.

(56) References Cited

U.S. PATENT DOCUMENTS 2,541,242 A * 2/1951 Grove ..................... A61F 9/045
                                                                        2/13
4,256,411 A * 3/1981 Podosek ................. B42F 13/06
                                                                        402/19
(Continued)

FOREIGN PATENT DOCUMENTS

JP          H04-108519 U          9/1992
JP          H07-030815 U          6/1995
(Continued)

OTHER PUBLICATIONS

May 29, 2024, Taiwanese Office Action issued for related TW Application No. 110115748.
(Continued)

*Primary Examiner* — Keri J Nelson
(74) *Attorney, Agent, or Firm* — Paratus Law Group, PLLC

(57)          ABSTRACT
There is provided a face shield that can easily be combined and used with various masks and a mask-equipped face shield. The face shield 1-1 is the face shield 1-1 that is attachable/detachable to/from a mask 2, and covers at least an eye of a face of a user who wears the mask 2. The face shield 1-1 is made of a film 101-1 having flexibility and translucency. At least a pair of cut lines 102L and 102R through which straps 202 of the mask 2 can be inserted are formed in both left and right parts of the face shield 1-1. The cut lines 102 have engagement parts 102a and 102b to be engaged with the straps 202 inserted through the cut lines 102.

5 Claims, 38 Drawing Sheets

(51) Int. Cl.

| | | |
|---|---|---|
| *A62B 18/08* | (2006.01) |
| *A61B 90/00* | (2016.01) |
| *A61F 9/02* | (2006.01) |
| *A62B 18/02* | (2006.01) |

(52) U.S. Cl.
   CPC .............. *A61B 90/05* (2016.02); *A61F 9/027* (2013.01); *A61F 9/029* (2013.01); *A62B 18/02* (2013.01)

(56)             References Cited

U.S. PATENT DOCUMENTS

| | | | | |
|---|---|---|---|---|
| 5,206,956 A * | 5/1993 | Olson | ..................... | G02C 7/16 |
| | | | | 128/857 |
| 5,406,944 A | 4/1995 | Gazzara | | |
| 5,446,925 A * | 9/1995 | Baker | ....................... | A61F 9/02 |
| | | | | 2/9 |
| 6,213,125 B1 * | 4/2001 | Reese | ............... | A41D 13/1184 |
| | | | | 2/9 |
| 2012/0047614 A1 | 3/2012 | Choi | | |

FOREIGN PATENT DOCUMENTS

| | | |
|---|---|---|
| JP | H07-178117 A | 7/1995 |
| JP | 2007-000378 A | 1/2007 |
| JP | 2007-068892 A | 3/2007 |
| JP | 3160039 U | 6/2010 |
| JP | 3162641 U | 9/2010 |
| JP | 2013-169346 A | 9/2013 |
| JP | 2016-029446 A | 3/2016 |
| JP | 3227242 U | 8/2020 |
| KR | 20-2008-0004323 U | 10/2008 |
| WO | WO 2016/013290 A1 | 1/2016 |

OTHER PUBLICATIONS

Jun. 21, 2024, Thai Office Action issued for related TH Application No. 2201007020.

Dec. 1, 2020, Japanese Office Action issued for related JP Application No. 2020-110720.

May 21, 2024, European Search Report issued for related EP Application No. 21796054.1.

Mar. 29, 2025, Chinese Office Action issued for related CN Application No. 202180030818.6.

Apr. 9, 2025, Taiwanese Office Action issued for related TW Application No. 110115748.

Aug. 16, 2025, Chinese Office Action issued for related CN Application No. 202180030818.6.

Oct. 16, 2025, Indian Office Action Issued for related IN Application No. 202217060897.

Nov. 15, 2025, Chinese Office Action issued for related CN Application No. 202180030818.6.

* cited by examiner

FIG. 15

| Conditions | Material Thickness (mm) | Total - Transmittance (%) | Reflectance (%) |
|---|---|---|---|
| 1:Moth eye structure (both sides) | 0.129 | 98.3 | 0.8 |
| 2:Wet AR (both sides) | 0.125 | 97.6 | 2.2 |
| 3:Wet AR (one side) | 0.115 | 94.7 | 4.7 |
| 4:Non Antireflection layer | 0.101 | 88.2 | 11.5 |
| 5:Non Antireflection layer | 0.099 | 90.6 | 8.4 |

35/41

39/41

FACE SHIELD AND MASK-EQUIPPED FACE SHIELD

CROSS REFERENCE TO PRIOR APPLICATION

This application is a National Stage Patent Application of PCT International Patent Application No. PCT/JP2021/016416 (filed on Apr. 23, 2021) under 35 U.S.C. § 371, which claims priority to Japanese Patent Application Nos. 2020-081005 (filed on May 1, 2020) and 2020-110720 (filed on Jun. 26, 2020), which are all hereby incorporated by reference in their entirety.

TECHNICAL FIELD

The present invention relates to a face shield and a mask-equipped face shield.

BACKGROUND ART

At medical institutions, masks and face shields are utilized as protective equipment for preventing droplet infection or airborne infection of virus or the like, adhesion of scattering objects such as blood and body fluids, and the like. A mask is used to cover respiratory organs (specifically, the mouth and the nose) of a user to prevent infection through the respiratory organs. A face shield is used to cover at least eyes of the face of the user to prevent infection through the eyes. Combined use of the mask and the face shield can effectively protect a healthcare worker against infection. Thus, a mask-equipped face shield in which a face shield is attached to a mask has been proposed (for example, see Patent Literature 1).

CITATION LIST

Patent Literature

Patent Literature 1: JP H7-178117A

SUMMARY OF INVENTION

Technical Problem

There are a wide variety of masks in accordance with their applications. Various masks exist and are utilized, examples of which include medical masks such as surgical masks and particulate respirator masks, masks for special users such as dust masks, and masks for normal users such as non-woven masks and gauze masks. Dimensions, materials, structures, and the like of these masks vary in accordance with applications, functions, protection grades, and the like of the masks. Thus, in order to improve convenience when a user wears a mask and a face shield, it is desired to selectively combine and use a face shield with various masks. A mask and a face shield can then readily be combined and used in accordance with a required protection grade at medical institutions, for example. In addition, in a case in which a need arises to prepare a large amount of mask-equipped face shields because of rapid expansion of an infection disease, for example, mask-equipped face shields can quickly be prepared.

With conventional technologies, however, it is difficult to selectively combine and use a face shield with various masks. In a mask-equipped face shield disclosed in Patent Literature 1, for example, the face shield is bonded and fixed to a mask with an adhesive agent or the like. It is therefore difficult to reattach the face shield to another mask.

The present invention was therefore made in view of such problems, and has an object to provide a face shield that can easily be combined and used with various masks and a mask-equipped face shield.

Solution to Problem

In order to solve the above-described problems, a face shield of the present invention is a face shield that is attachable/detachable to/from a mask, and covers at least an eye of a face of a user who wears the mask. The face shield is made of a film having flexibility and translucency. At least a pair of cut lines through which straps of the mask can be inserted are formed in both left and right parts of the face shield, and the cut lines have engagement parts to be engaged with the straps inserted through the cut lines.

The engagement parts may restrict movement of the straps in two directions, a direction in which the straps are inserted through the cut lines and a direction along the cut lines.

The straps inserted through the cut lines may be caught by portions of the film on both sides of the engagement parts of the cut lines.

The cut lines may be closed-type cut lines included in an inner side of the face shield without intersecting with an outer edge of the face shield. The engagement parts may be respectively formed at both ends of the closed-type cut lines. Two of the straps extending from one side in a left-right direction of the mask may be inserted through one of the closed-type cut lines formed on the one side in the left-right direction of the face shield. The two of the straps may be respectively engaged with two of the engagement parts formed at both ends of the one of the closed-type cut lines.

A plurality of pairs of the closed-type cut lines may be formed in both the left and right parts of the face shield, and an interval between paired ones of the closed-type cut lines may be different from pair to pair.

The cut lines may be open-type cut lines having one ends intersecting with an outer edge of the face shield, and the other ends arranged on an inner side of the face shield. The engagement parts may be formed at the other ends of the open-type cut lines. Two pairs of the open-type cut lines may be formed side by side in an up-down direction in both the left and right parts of the face shield. Two of the straps extending from one side in a left-right direction of the mask may be respectively inserted through two of the open-type cut lines formed in one side in the left-right direction of the face shield. The two of the straps may be respectively engaged with two of the engagement parts formed at the other ends of the two open-type cut lines.

The engagement parts may be portions in which the cut lines are formed into a sawtooth shape.

The engagement parts may be portions in which the cut lines are branched.

The engagement parts may be portions in which the cut lines are curved.

In order to solve the above-described problems, a face shield of the present invention is a face shield that is attachable/detachable to/from a mask, and covers at least an eye of a face of a user who wears the mask. The face shield may be made of a film having flexibility and translucency. At least a pair of changeable parts that can be deformed may be formed in both left and right parts of the face shield. Looped parts through which straps of the mask can be inserted may be formed by deformation of the changeable parts.

The changeable parts can be deformed by being partially cut out along cut lines formed in the face shield, and the looped parts may be engaged with the straps inserted through the looped parts.

Two or more of the looped parts may be formed away from each other in the left-right direction by deformation of the changeable parts on one side in the left-right direction of the face shield, and an upper one of the straps of the mask may be inserted through the two or more of the looped parts.

Two or more of the changeable parts may be formed away from each other in the left-right direction on one side in the left-right direction of the face shield, and the two or more of the looped parts may be formed by deformation of the two or more of the changeable parts.

When the upper one of the straps of the mask is inserted through the two or more of the looped parts, the looped parts may relatively be movable with respect to the strap in a direction through which the strap is inserted.

Insertion parts formed of cut lines may be formed in the face shield at positions adjacent to the changeable parts, and the looped parts may be formed by insertion of the changeable parts in the insertion parts.

Locking claws that lock the changeable parts in the insertion parts may be formed in the changeable parts.

A notch may be formed in the face shield at a position to be opposed to a respiratory organ of the user.

A through-hole may be formed in the face shield at a position to be opposed to a respiratory organ of the user or at a position lateral to or below the position to be opposed to the respiratory organ.

A folding part that is foldable toward the face of the user may be formed in the face shield at a position to be opposed to a nose of the user or at a position to be opposed to a region below the nose.

A folding part that is foldable toward the face of the user may be formed in the face shield at a position to be opposed to a forehead or a frontal region of a head of the user.

A folding part that is foldable toward the face of the user may be formed in the face shield at a position to be opposed to a jaw of the user or at a position to be opposed to a region below the jaw.

Folding lines may be arranged on the face shield between a portion to be located on a front side of the face of the user and portions to be located on lateral sides of the face of the user, and the portions to be located on the lateral sides may be foldable along the folding lines with respect to the portion to be located on the front side.

An antireflection layer may be provided on at least one of surfaces of the face shield.

The antireflection layer may have a micro concave-convex structure having a pitch smaller than or equal to a wavelength of visible light.

The face shield may have a total transmittance of more than or equal to 94.0%.

The face shield may have a formative structure that can be formed into a shape that tapers with distance from the face of the user.

In order to solve the above-described problems, a mask-equipped face shield of the present invention includes the above-described face shield, and a mask to/from which the above-described face shield is attachable/detachable.

4

Advantageous Effects of Invention

According to the present invention, a face shield can easily be combined and used with various masks.

BRIEF DESCRIPTION OF DRAWINGS

FIG. 15 is a table showing various conditions for film surface treatment.

DESCRIPTION OF EMBODIMENTS

Figure 1:
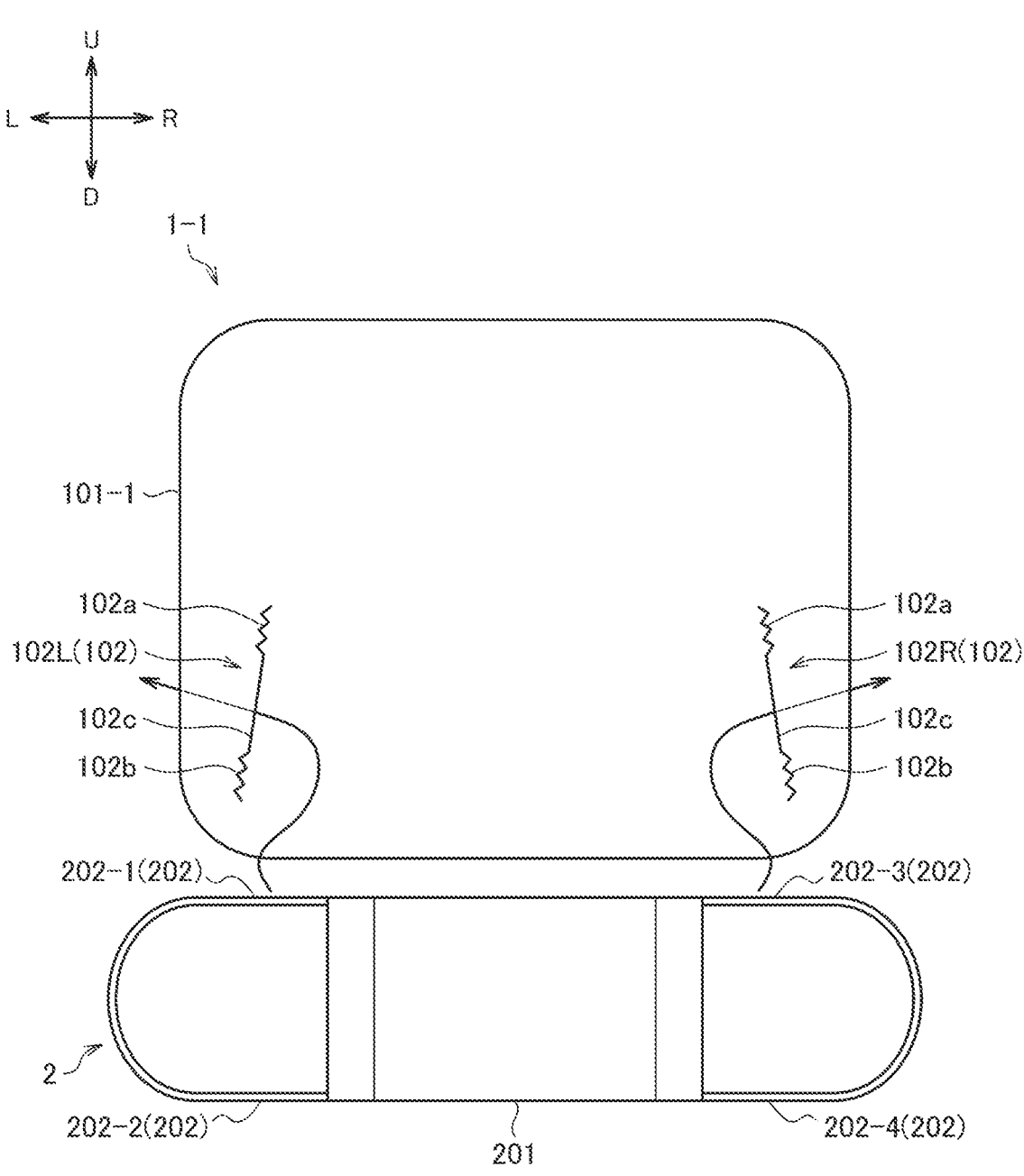
FIG. 1 is a plan view showing a face shield according to a first embodiment of the present invention.

Hereinafter, embodiments of the present invention will be described in detail with reference to the attached drawings. Dimensions, materials, other specific numerical values, and the like presented in the embodiments are merely for illustration for facilitating understanding of the invention, and do not limit the present invention unless otherwise specified. Note that in the present specification and the drawings, elements having substantially the same function and configuration have the same reference characters allotted, and repeated description will be omitted. Illustration of elements not directly related to the present invention will also be omitted.

First Embodiment

A face shield 1-1 according to a first embodiment of the present invention will be described with reference to FIGS. 1 to 3.

FIG. 1 is a plan view showing the face shield 1-1. FIG. 2 is a perspective view showing a usage state of the face shield 1-1.

As shown in FIG. 1, the face shield 1-1 is attachably/detachably mounted on the mask 2, and is used in a state attached to the mask 2. When the face shield 1-1 is used, a user (for example, a healthcare worker) wears the mask 2 to which the face shield 1-1 has been attached as shown in FIG. 2. The mask 2 covers the respiratory organs (the nose and the mouth) and their peripheries on the face of the user. On the other hand, the face shield 1-1 is arranged so as to cover the face of the user in a state supported by the mask 2, and widely covers the front and sides of the face of the user from the outside of the mask 2. A mask-equipped face shield including the face shield 1-1 and the mask 2 is used in this manner. This can prevent virus, bacteria, or the like contained in droplets in the air or scattering objects such as blood and body fluids occurred in a surgical procedure or treatment, for example, from adhering to the face of the user or entering the respiratory organs, eyes, or the like. Thus, the healthcare worker or the like can effectively be protected against infection.

Note that each of the drawings referred to in the present specification are shown with a front direction, a back direction, a left direction, a right direction, an up direction, and a down direction with respect to the user respectively indicated as an F direction, a B direction, an L direction, an R direction, a U direction, and a D direction.

The mask 2 is used to cover the respiratory organs (specifically, the mouth and the nose) of the user who wears the mask 2 to prevent infection through the respiratory organs. Note that in the present specification, the respiratory organs should only include at least the mouth, and may include both the mouth and the nose. As shown in FIG. 1, the mask 2 has a main body part 201 and straps 202.

The main body part 201 is a portion to be opposed to the respiratory organs of the user when in use to cover the respiratory organs of the user. The main body part 201 has breathability and a function of preventing virus, bacteria, or the like contained in droplets or the like from entering. The main body part 201 has a structure in which multiple layers of filters made of various materials are laminated, for example. Particularly in a case in which the mask 2 is a medical mask such as a surgical mask, the mask 2 preferably is excellent in a liquid protection property against blood, body fluids, and the like as well as a collection property of capturing bacteria or particulates contained in droplets floating in the air.

The straps 202 are string-shaped members to be worn on any region (ears in the mask 2 of FIG. 2, for example) of the head of the user when in use. The mask 2 is provided with at least a total of four straps 202 on both sides, at least two each on one side in the left-right direction of the main body part 201. The straps 202 may be of any type among an ear-hung type (see FIGS. 1 and 2), a tie-string type (see FIG. 3), and an overhead type (see FIGS. 23 and 24), or may be of any other type.

Figure 2:
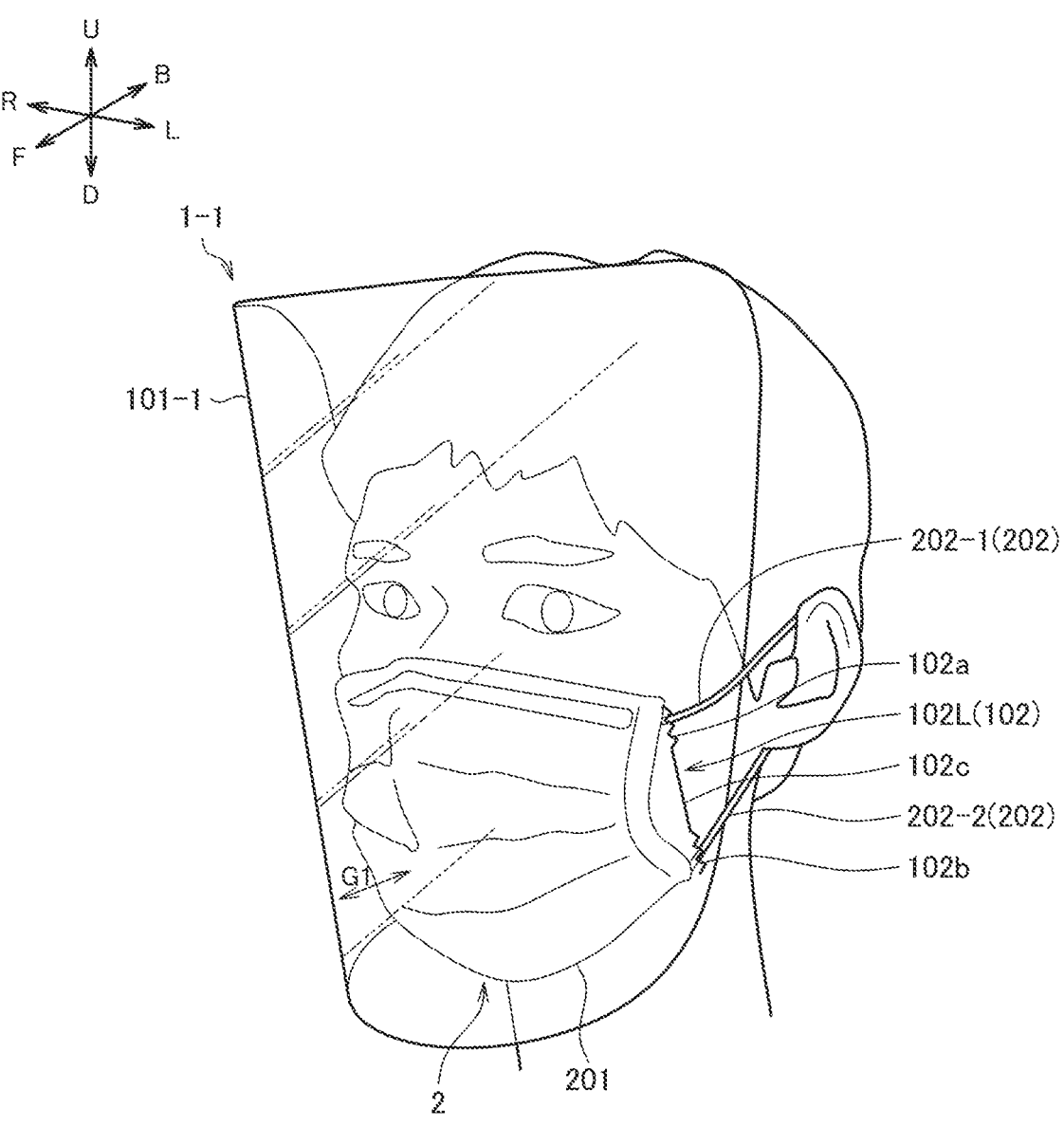
FIG. 2 is a perspective view showing a usage state of the face shield according to the first embodiment of the present invention.
Figure 3:
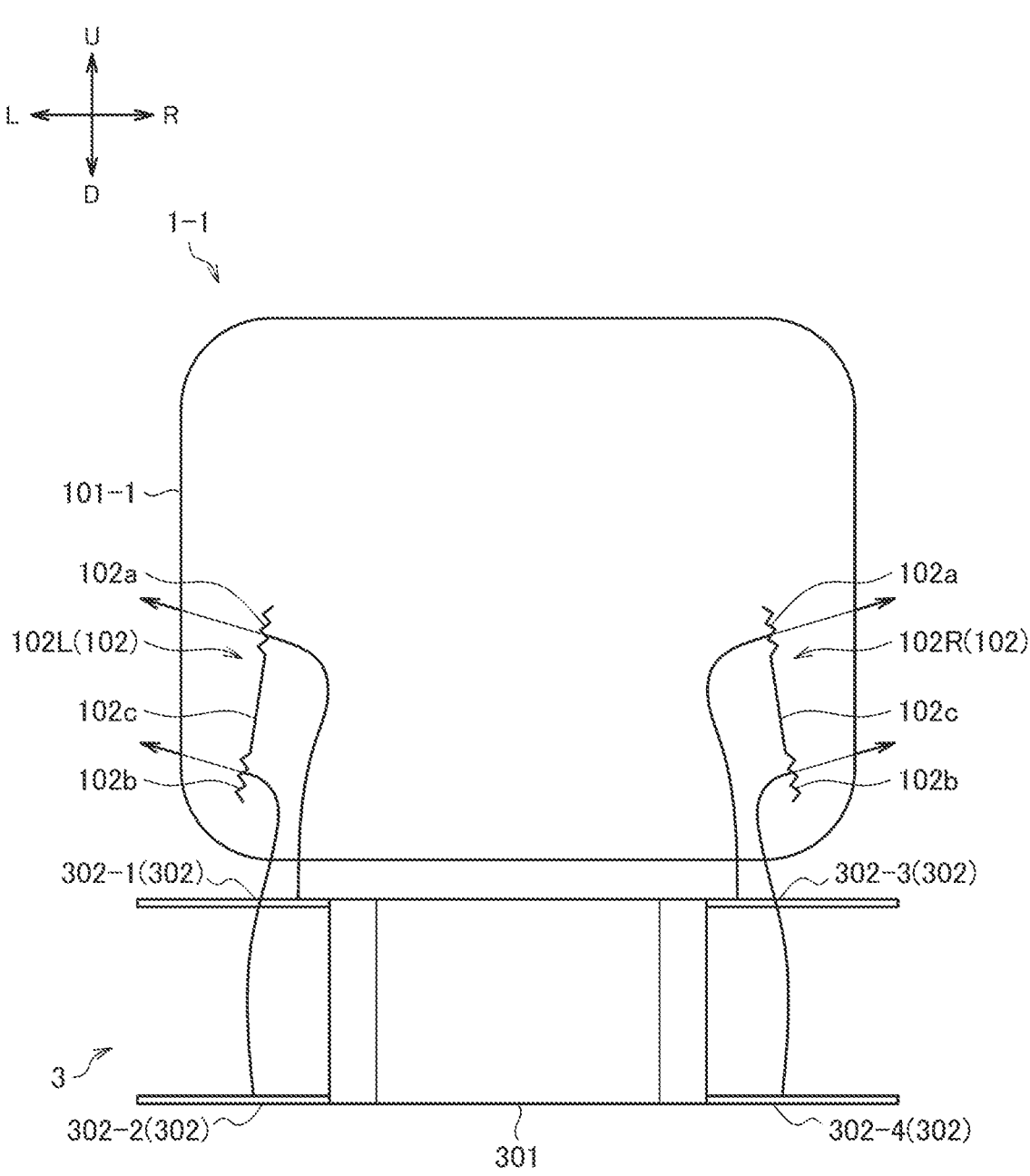
FIG. 3 is a drawing for explaining a mask different from that of FIG. 1, to which the face shield according to the first embodiment of the present invention is attachable.

In the example of the straps 202 of the ear-hung type shown in FIGS. 1 and 2, two straps 202-1 and 202-2 extend from one side in the left-right direction of the main body part 201, and two straps 202-3 and 202-4 extend from the other side in the left-right direction of the main body part 201. Specifically, the strap 202-1 extends from the upper side on the left side of the main body part 201, and the strap 202-2 extends from the lower side on the left side of the main body part 201. The strap 202-1 and the strap 202-2 are connected to each other to constitute an annular strap to be worn on the left ear of the user. The strap 202-3 extends from the upper side on the right side of the main body part 201, and the strap 202-4 extends from the lower side on the right side of the main body part 201. The strap 202-3 and the strap 202-4 are connected to each other to constitute an annular strap to be worn on the right ear of the user. From the perspective of a wearing property of the mask 2, the straps 202 preferably are composed of an elastic string member such as a rubber string.

The face shield 1-1 is protective equipment to be arranged on the front side of the face of the user who wears the mask 2 away from the face. The face shield 1-1 is used to cover at least the eyes on the face of the user to prevent infection through the eyes. However, the face shield 1-1 may entirely or partially cover the nose and mouth, jaw, left and right cheeks, forehead, ears, frontal region of the head, temporal region of the head, neck, and the like of the user, as shown in FIG. 2. As shown in FIG. 1, the face shield 1-1 is made of a film 101-1 having flexibility and translucency. Note that one or more films 101-1 may form the face shield 1-1 (for example, a plurality of films may be laminated to constitute the film 101-1 constituting the face shield 1-1).

The film 101-1 is formed of a material consisting primarily of a plastic material having transparency, for example. Examples of the material of the film 101-1 include methyl methacrylate (co)polymer, polycarbonate, styrene (co)polymer, methyl methacrylate-styrene copolymer, cellulose diacetate, cellulose triacetate, cellulose acetate butylate, polyester, polyamide, polyimide, polyethersulfone, polysulfone, polypropylene, polymethylpentene, polyvinyl chloride, polyvinyl acetal, polyether ketone, polyurethane, glass, and the like. However, the material of the film 101-1 is not limited to these materials.

In the case of using a plastic material as the film 101-1, a primer layer not shown may further be provided by surface treatment in order to further improve the surface energy, coatability, slidability, flatness, and the like of a surface of the plastic material. Examples of the primer layer include an organoalkoxymetal compound, polyester, acrylic-modified polyester, polyurethane, and the like. In addition, in order to obtain an effect equivalent to that when the primer layer is provided, a surface of the film 101-1 may be subjected to a corona discharge treatment, a UV radiation treatment, or the like.

The film 101-1 may be formed by a method such as stretching resin described above, or diluting the resin in a solvent, followed by deposition into a film shape and drying, for example. The thickness of the film 101-1 preferably is selected as appropriate in accordance with the application of the face shield 1-1, and may be more than or equal to 50 μm and less than or equal to 500 μm, for example, and preferably is more than or equal to 100 μm and less than or equal to 250 μm. From the perspective of reducing reflection of external light to keep the field of view of the user well, total transmittance of the face shield 1-1 should be more than or equal to 94.0%, and preferably should be more than or equal to 98.0%.

Note that materials of and methods of manufacturing films 101-2 to 101-21 of other embodiments which will be described later are similar to those of the film 101-1 described above.

A pair of cut lines 102L and 102R through which the straps 202 of the mask 2 can be inserted are formed in both the left and right parts of the face shield 1-1. However, there should only be at least one pair of the cut lines 102, 102 as will be described later, and there may be two or more pairs. Note that in a case of not particularly distinguishing between the cut line 102L and the cut line 102R, they will simply be called the cut lines 102 as well in the following description. Note that in the present specification, a cut line is a cut line formed by linearly cutting a film. The cut line is different from a typical opening (a typical long hole or slit having an opening width) formed so as to extend through a film. The cut line means a cut line having no opening width, rather than a slit having an opening width. In other words, portions of the film 101-1 on both sides of the cut line are divided by the cut line, but are in contact with each other with no gap therebetween.

The cut line 102 is a closed-type cut line included in an inner side of the face shield 1-1 (that is, an inner side relative to an outer edge of the film 101-1) without intersecting with an outer edge of the face shield 1-1 (that is, the outer edge of the film 101-1). The cut line 102 is formed so as to extend in a direction (such as the up-down direction or oblique direction, for example) that intersects with the left-right direction.

The cut line 102L is formed on the lower side of the left part of the film 101-1. The two straps 202-1 and 202-2 extending from the left side of the mask 2 are inserted through the cut line 102L. The cut line 102R is formed on the lower side of the right part of the film 101-1. The two straps 202-3 and 202-4 extending from the right side of the mask 2 are inserted through the cut line 102R.

The cut line 102 has engagement parts 102a and 102b to be engaged with the straps 202 inserted through the cut line 102, and a linear part 102c. The engagement parts 102a and 102b are formed respectively at both ends of the cut line 102. In the present embodiment, the engagement parts 102a and 102b are portions in which the cut line 102 is formed into a sawtooth shape (zigzag line portions). The engagement part 102a is formed at the upper end of the cut line 102, and the engagement part 102b is formed at the lower end of the cut line 102. The linear part 102c is a portion between the engagement part 102a and the engagement part 102b in the cut line 102. The linear part 102c is a portion in which the cut line 102 is formed linearly. Note that in the cut line 102 according to the present embodiment, the engagement parts 102a and 102b at both the ends are coupled by the linear part 102c which is linear, however, the present invention is not limited to such an example. A coupling line that couples the engagement parts 102a and 102b may be, for example, a curved line which is gently curved or the like rather than being linear.

The two straps 202-1 and 202-2 inserted through the cut line 102L on the left side are respectively engaged with the two engagement parts 102a and 102b formed at both the ends of the single cut line 102L. The strap 202-1 is engaged with the engagement part 102a of the cut line 102L, and the strap 202-2 is engaged with the engagement part 102b of the cut line 102L. Similarly, the two straps 202-3 and 202-4 inserted through the cut line 102R on the right side are engaged respectively with the two engagement parts 102a and 102b formed at both the ends of the single cut line 102R. The strap 202-3 is engaged with the engagement part 102a of the cut line 102R, and the strap 202-4 is engaged with the engagement part 102b of the cut line 102R. Particularly from the perspective of stably holding and fixing the face shield 1-1, portions of the straps 202 located as close to the main body part 201 as possible preferably are engaged with the engagement parts 102a and 102b.

The straps 202 inserted through the cut line 102 are caught by portions of the film 101-1 on both sides of the engagement parts 102a and 102b. The portions of the film 101-1 on both the sides of the engagement parts 102a and 102b particularly have a complicated shape as compared with portions on both sides of the linear part 102c. A large friction resistance is thereby produced between the straps 202 inserted through the cut line 102 and the engagement parts 102*a*, 102*b*, so that the straps 202 inserted through the cut line 102 are firmly caught. Displacement of the straps 202 in two directions, the direction in which the straps 202 are inserted through the cut line 102 and the direction along the cut line 102 is thereby restricted by the engagement parts 102*a* and 102*b*. Thus, merely by inserting the straps 202 through the cut line 102, the face shield 1-1 can easily be attached/detached to/from the mask 2, and the face shield 1-1 can stably be held by and fixed to the mask 2 with the straps 202 caught by the engagement parts 102*a* and 102*b* when the face shield 1-1 is used.

Note that although the example of the engagement parts 102*a* and 102*b* having a sawtooth shape has been described above, the shape of the engagement parts is not limited to this example as will be described later. The engagement parts may have any other shape as long as a larger friction resistance than in a case of a linear cut line may be produced between the engagement parts and the straps 202.

As described above, the face shield 1-1 is attached to the mask 2 by inserting the straps 202 of the mask 2 through the cut lines 102L and 102R. Then, the user wears the mask 2 to which the face shield 1-1 has been attached, as shown in FIG. 2. When the mask 2 is worn, the face shield 1-1 is deformed into a curved shape along a substantially cylindrical surface centering on a vertical axis, and covers the front and lateral faces of the face of the user in a state spaced from the face of the user. In this manner, the face shield 1-1 formed of a simple, flat-shaped film (see FIG. 1) at normal times is deformed into a shape curved in the left-right direction along the face in a state supported by the mask 2 when in use (see FIG. 2).

Next, a method of manufacturing the face shield 1-1 will be described. First, a film roll to be the material of the film 101-1 is prepared. Then, the prepared film roll is subjected to punching. In punching, a contour (that is, an outline) of the face shield 1-1 and the cut lines 102L and 102R are punched from the film roll. Both the contour of the face shield 1-1 and the cut lines 102 preferably are formed each time of punching. The face shield 1-1 is thereby manufactured easily and quickly.

The face shield 1-1 according to the first embodiment has been described above in detail. As described above, the pair of the cut lines 102L and 102R through which the straps 202 of the mask 2 can be inserted are formed in both the left and right parts of the face shield 1-1 according to the first embodiment. In addition, the cut line 102 has the engagement parts 102*a* and 102*b* to be engaged with the straps 202 inserted through the cut line 102. In particular, the cut line 102 with the engagement parts 102*a* and 102*b* formed on both the sides is adaptable to the straps 202 of the mask 2 of various types, and highly versatile. In other words, the two straps 202 are inserted through the single cut line 102, and the respective straps 202 are held by the engagement parts 102*a* and 102*b* at both the ends. Such a configuration enables the face shield 1-1 to be easily attached/detached to/from the mask 2 of various types, and the face shield 1-1 attached to the mask 2 is stably held in the state covering the face of the user. The face shield 1-1 can thus be selectively combined with various masks and easily used. This enables a mask and the face shield 1-1 to readily be combined and used at medical institutions, for example, in accordance with a required protection grade, which improves convenience. In addition, in a case in which a need arises to prepare a large amount of mask-equipped face shields because of rapid expansion of an infection disease, for example, mask-equipped face shields can quickly be prepared.

In addition, the face shield 1-1 according to the present embodiment can easily be mounted on and integrated with commercially-available various masks. In addition, at the time of mounting, no special attachment instrument or component is required, so that an operation of attaching/detaching the face shield 1-1 and the mask 2 is easy and convenient. In addition, by removing the face shield 1-1 from the mask 2, only the face shield 1-1 or only the mask 2 can be replaced.

Further, the face shield 1-1 according to the first embodiment enables a gap G1 (see FIG. 2) to be formed between the mask 2 and the face shield 1-1. This can prevent the face shield 1-1 from fogging up because of exhaled air of the user, and enables the field of view to be kept well. Note that the gap G1 can be adjusted by adjusting positions of the straps 202 of the mask 2 engaged with the engagement parts 102*a* and 102*b*, for example. Thus, the gap G1 can be adjusted as appropriate in accordance with the size of the mask 2 or the size of the face of the user. Note that adjustment of the gap G1 also enables the face shield 1-1 to fit well to the face of the user.

Further, the face shield 1-1 according to the first embodiment eliminates the need for attachment equipment such as a dedicated frame for mounting the face shield 1-1. Thus, the protective equipment to be worn by the user can be reduced in weight as a whole. This can reduce fatigue of the user, and can also improve a wearing feeling. In addition, it does not appear to be heavy equipment, so that people around the user can have a good impression on the appearance.

Further, the face shield 1-1 according to the first embodiment eliminates a step of bonding the face shield 1-1 to the mask 2 (such as a gluing step through use of an adhesive agent or the like, or a welding step, for example). This can shorten a manufacturing process, and also facilitates manufacturing.

Further, the face shield 1-1 according to the first embodiment enables the face shield 1-1 to be distributed alone separately from the mask 2. In addition, a plurality of the face shields 1-1 as flat films can be packed and transported in a state stacked one upon another. This facilitates packaging and distribution, and can reduce a storage space and a transportation space.

Further, in a case in which either the face shield 1-1 or the mask 2 is damaged or contaminated, the face shield 1-1 according to the first embodiment enables a sound one of the members to be used continually by replacing a damaged or contaminated one of the members. This enables effective utilization of the face shield 1-1 and the mask 2 without unnecessary disposal.

In particular, in the face shield 1-1 according to the first embodiment, the two straps 202 extending from one side in the left-right direction of the mask 2 are inserted through the cut line 102 which is a single closed-type cut line formed on one side in the left-right direction of the face shield 1-1. Then, the two straps 202 are engaged respectively with the two engagement parts 102*a* and 102*b* formed at both the ends of the single cut line 102. The face shield 1-1 is thereby supported by a total of the four straps 202 at four points. This enables the face shield 1-1 to be held and fixed more stably when in use.

Note that although the example in which the face shield 1-1 is attached to the mask 2 of the ear-hung type has been described above, the face shield 1-1 may be attached to a mask of another type. FIG. 3 is a plan view showing an example of attaching the face shield 1-1 to a mask 3 of the tie-string type. As shown in FIG. 3, the mask 3 has a main body part 301 and straps 302.

The main body part 301 has a configuration similar to that of the main body part 201 described above. A strap 302-1 extends from the upper side on the left side of the main body part 301, and a strap 302-2 extends from the lower side on the left side of the main body part 301. In the mask 3 of the tie-string type, the strap 302-1 and the strap 302-2 are separate from each other unlike the above-described mask 2 of the ear-hung type. A strap 302-3 extends from the upper side on the right side of the main body part 301, and a strap 302-4 extends from the lower side on the right side of the main body part 301. The strap 302-3 and the strap 302-4 are separate from each other similarly to the strap 302-1 and the strap 302-2. When the face shield 1-1 and the mask 3 are used, the strap 302-1 and the strap 302-3 are tied to each other on the upper side at the back of the head of the user, and the strap 302-2 and the strap 302-4 are tied to each other on the lower side at the back of the head of the user. In the mask 3 of the tie-string type, the face shield 1-1 is worn on the user together with the mask 3.

The two straps 302-1 and 302-2 extending from the left side of the mask 3 are inserted through the cut line 102L of the face shield 1-1. The two straps 302-3 and 302-4 extending from the right side of the mask 3 are inserted through the cut line 102R of the face shield 1-1. The strap 302-1 is engaged with the engagement part 102a of the cut line 102L, and the strap 302-2 is engaged with the engagement part 102b of the cut line 102L. The strap 302-3 is engaged with the engagement part 102a of the cut line 102R, and the strap 302-4 is engaged with the engagement part 102b of the cut line 102R. The face shield 1-1 can thereby easily be attached/detached to/from the mask 3 of the tie-string type similarly to the mask 2 of the ear-hung type, and the face shield 1-1 can stably be held by the mask 3.

Second Embodiment

A face shield 1-2 according to a second embodiment of the present invention will be described with reference to FIGS. 4 and 5.

Figure 4:
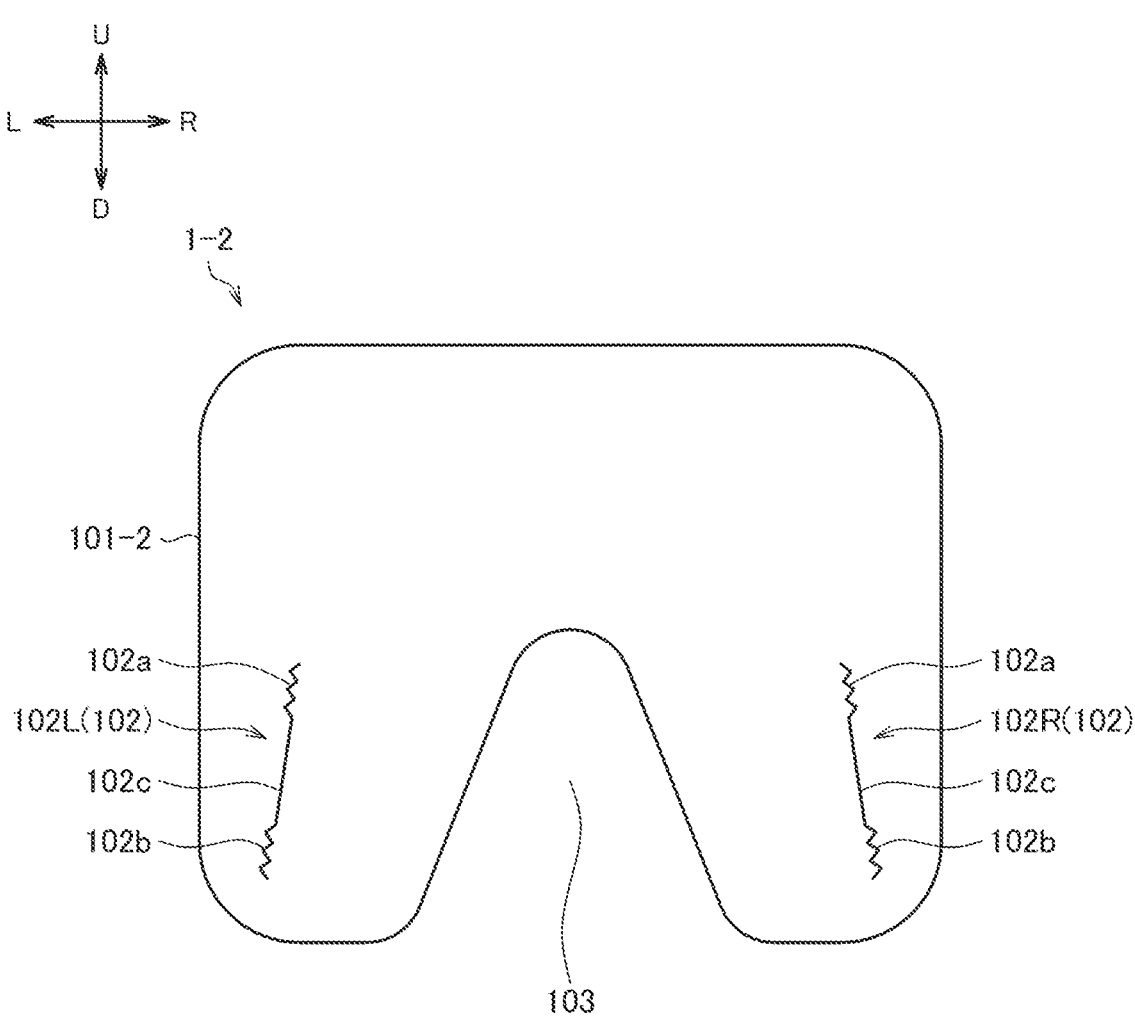
FIG. 4 is a plan view showing a face shield according to a second embodiment of the present invention.

FIG. 4 is a plan view showing the face shield 1-2. FIG. 5 is a perspective view showing a usage state of the face shield 1-2. FIG. 5 shows an example in which the face shield 1-2 is attached to the mask 2 of the ear-hung type. However, the face shield 1-2 can easily be combined and used with various masks similarly to the face shield 1-1.

The face shield 1-2 according to the second embodiment is different from the face shield 1-1 according to the first embodiment in that a notch 103 is formed in the face shield 1-2 at a position to be opposed to the respiratory organs of a user.

Figure 5:
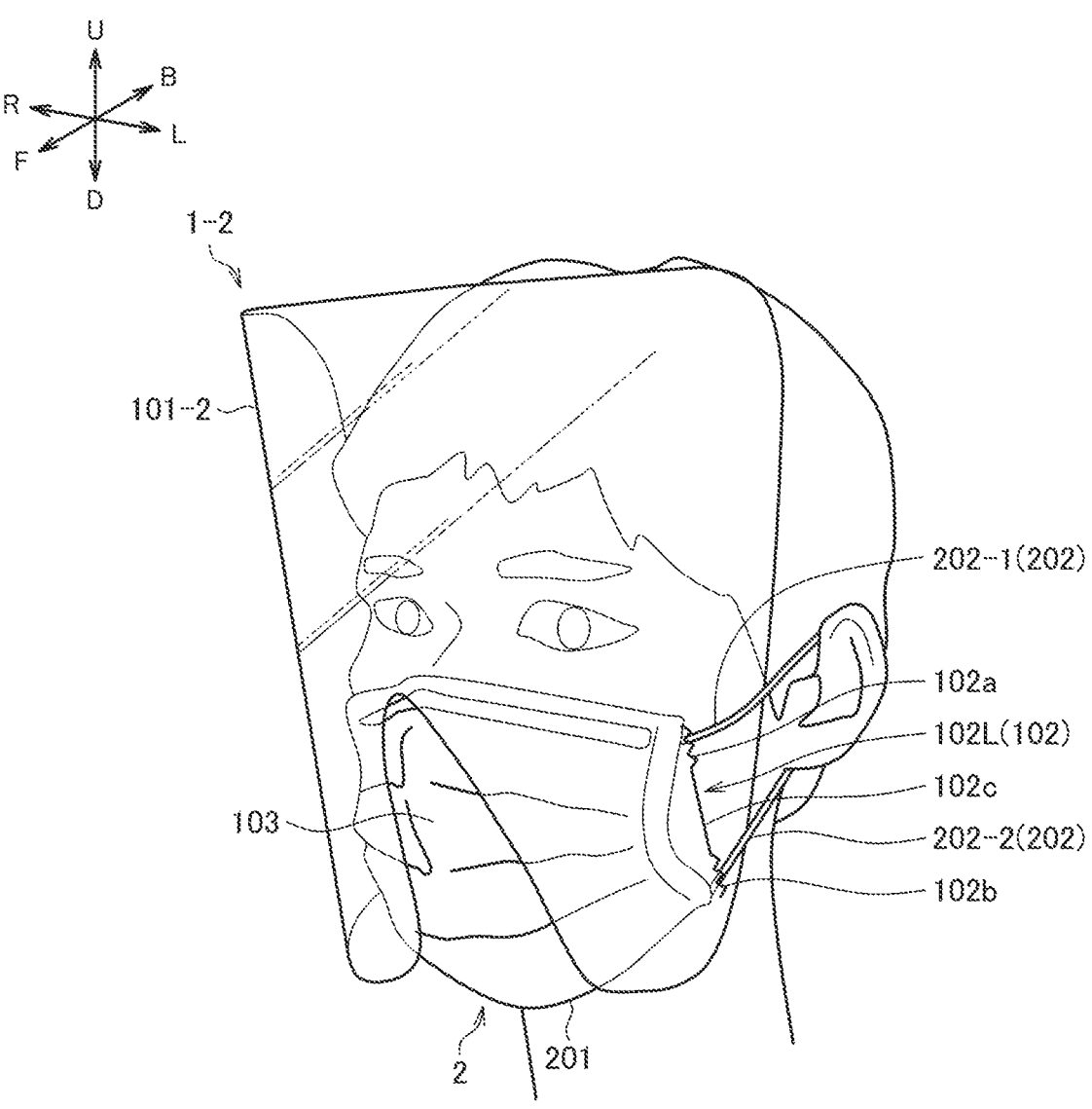
FIG. 5 is a perspective view showing a usage state of the face shield according to the second embodiment of the present invention.

As shown in FIGS. 4 and 5, the notch 103 is arranged in a region between the cut line 102L and the cut line 102R in the face shield 1-2 (specifically, a film 101-2 that forms the face shield 1-2). The notch 103 is formed so as to extend upward from a lower end of a central part of the face shield 1-2. The notch 103 has a shape whose width in the left-right direction is narrowed upward (for example, a substantially triangular shape). However, the shape of the notch 103 is not limited to this example, and may be rectangular, for example.

As shown in FIG. 5, the notch 103 is formed at a position to be opposed to the respiratory organs (for example, the mouth and the nose) of the user when in use. Since the notch 103 is thereby arranged outside a portion of the mask 2 that covers the respiratory organs of the user, the relevant portion of the mask 2 is exposed to the outside through the notch 103 without being covered by the face shield 1-2. Thus, air exhaled from the respiratory organs of the user passes through or bypasses the mask 2, and is then discharged to the outside of the face shield 1-2 through the notch 103. This can effectively prevent the face shield 1-2 from fogging up because of exhaled air of the user, and enables the field of view to be kept well.

Third Embodiment

A face shield 1-3 according to a third embodiment of the present invention will be described with reference to FIG. 6.

Figure 6:
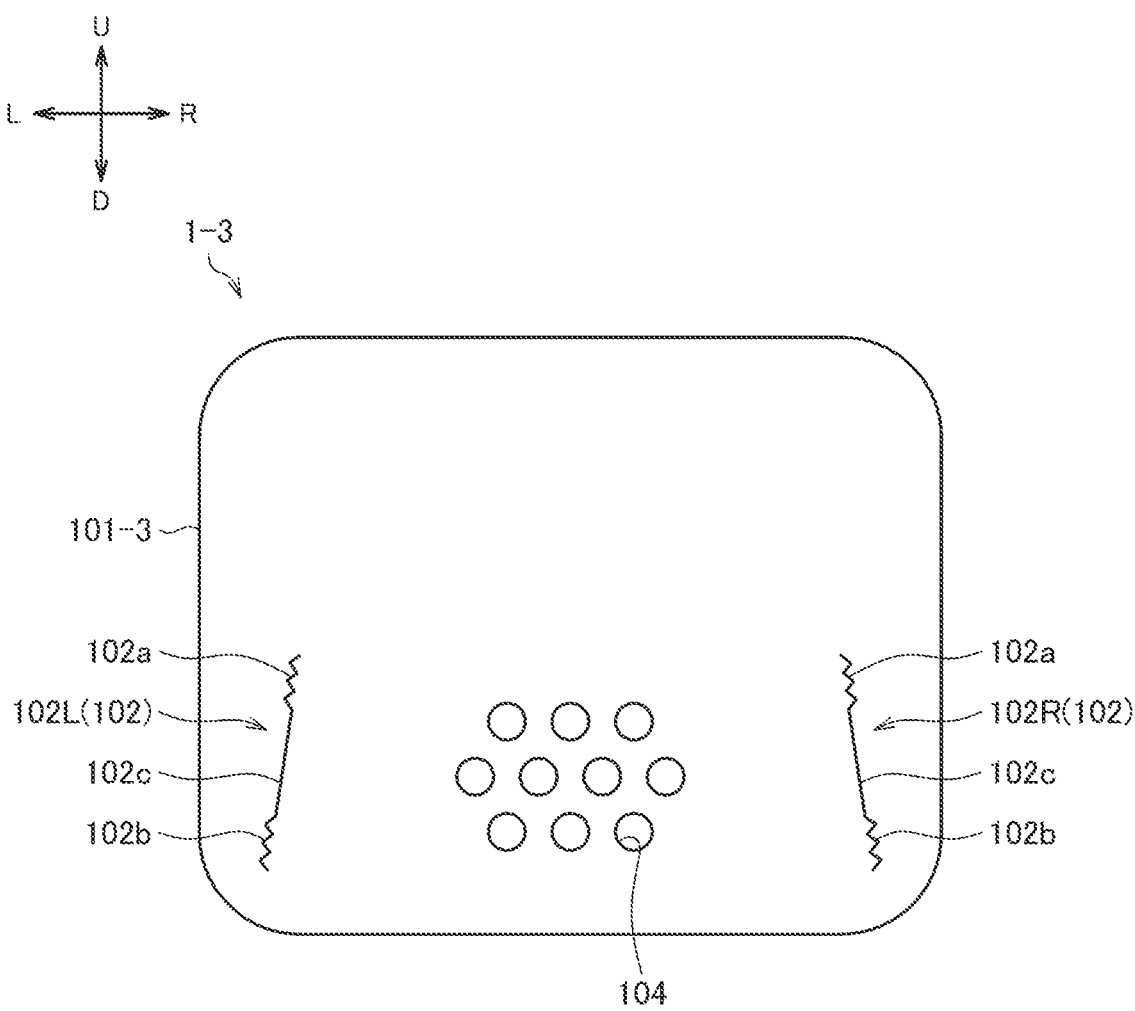
FIG. 6 is a plan view showing a face shield according to a third embodiment of the present invention.

FIG. 6 is a plan view showing the face shield 1-3.

The face shield 1-3 according to the third embodiment is different from the face shield 1-1 according to the first embodiment in that through-holes 104 are formed in the face shield 1-3 at a position to be opposed to the respiratory organs of a user. The face shield 1-3 according to the third embodiment is equivalent to an example in which a portion of the face shield 1-3 through which exhaled air passes is changed from the notch 103 of the face shield 1-2 according to the second embodiment to the through-holes 104.

As shown in FIG. 6, the plurality of through-holes 104 are formed in a region between the cut line 102L and the cut line 102R of the face shield 1-3 (specifically, a film 101-3 that forms the face shield 1-3). The through-holes 104 have a circular shape, for example, but are not limited to this example, and may have an oval shape or a polygonal shape, for example. In addition, the arrangement of the through-holes 104 is not limited to the example shown in FIG. 6. For example, the through-holes 104 may be arranged at regular intervals, or may be arranged at unequal intervals. Alternatively, the through-holes 104 may be arranged around the position to be opposed to the respiratory organs (for example, a position lateral to or below the position to be opposed to the respiratory organs). In addition, the number of the through-holes 104 provided is not limited to that of the example shown in FIG. 6, and there may be a single through-hole 104, for example.

The through-holes 104 are arranged at the position to be opposed to the respiratory organs (for example, the mouth and the nose) of the user or a position in a peripheral lateral or lower part when in use, and function as ventilation holes. Thus, air exhaled from the respiratory organs of the user passes through or bypasses the mask 2, and is then discharged to the outside of the face shield 1-3 through the through-holes 104. This can effectively prevent the face shield 1-3 from fogging up because of exhaled air of the user, and enables the field of view to be kept well. In addition, the presence of the through-holes 104 also exerts an effect that makes voice of the user more audible to a conversational partner during a conversation.

Fourth Embodiment

A face shield 1-4 according to a fourth embodiment of the present invention will be described with reference to FIGS. 7 and 8.

Figure 7:
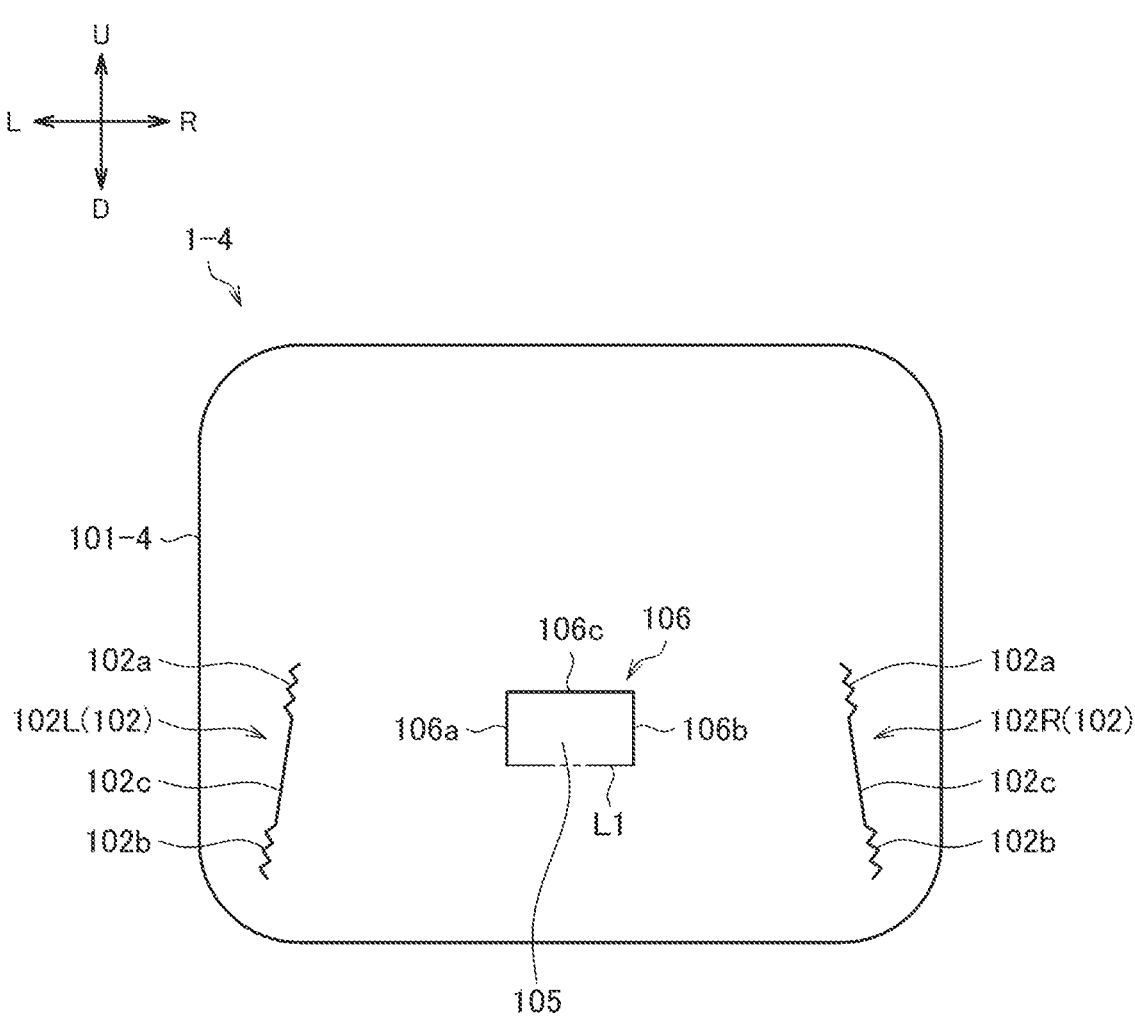
FIG. 7 is a plan view showing a face shield according to a fourth embodiment of the present invention.

FIG. 7 is a plan view showing the face shield 1-4. FIG. 8 is a perspective view showing a usage state of the face shield 1-4. FIG. 8 shows an example in which the face shield 1-4 is attached to the mask 2 of the ear-hung type. However, the face shield 1-4 can easily be combined and used with various masks similarly to the face shield 1-1.

The face shield 1-4 according to the fourth embodiment is different from the face shield 1-1 according to the first embodiment in that a folding part 105 that is foldable toward the face of a user is formed in the face shield 1-4 at a position to be opposed to the nose of the user or at a position to be opposed to a region below the nose.

As shown in FIG. 7, a cut line 106 for forming the folding part 105 is formed in a region between the cut line 102L and the cut line 102R of the face shield 1-4 (specifically, a film 101-4 that forms the face shield 1-4). The cut line 106 has a U-shape. The cut line 106 has a linear part 106a, a linear part 106b, and a linear part 106c. The linear parts 106a and 106b are linear parts of the cut line 106 that extend in the up-down direction. The linear parts 106a and 106b are spaced from each other in the left-right direction, and arranged in parallel. The linear part 106c is a linear part of the cut line 106 that extends in the left-right direction. The linear part 106c is formed so as to connect the upper end of the linear part 106a and the upper end of the linear part 106b. However, the shape of the cut line 106 is not limited to this example, and may be an arc shape, for example. Alternatively, an arrangement obtained by rotating this example by 90 degrees may be adopted, or a plurality of folding parts may be arranged. Alternatively, a structure may be adopted in which a plurality of cut lines are provided in parallel and folded in multiple steps.

The folding part 105 is a portion of the face shield 1-4 that can be deformed by being partially cut out along the cut line 106. The folding part 105 is foldable along a folding line L1 formed so as to connect the lower end of the linear part 106a and the lower end of the linear part 106b. The folding line L1 may be perforated so as to facilitate folding of the folding part 105.

Figure 8:
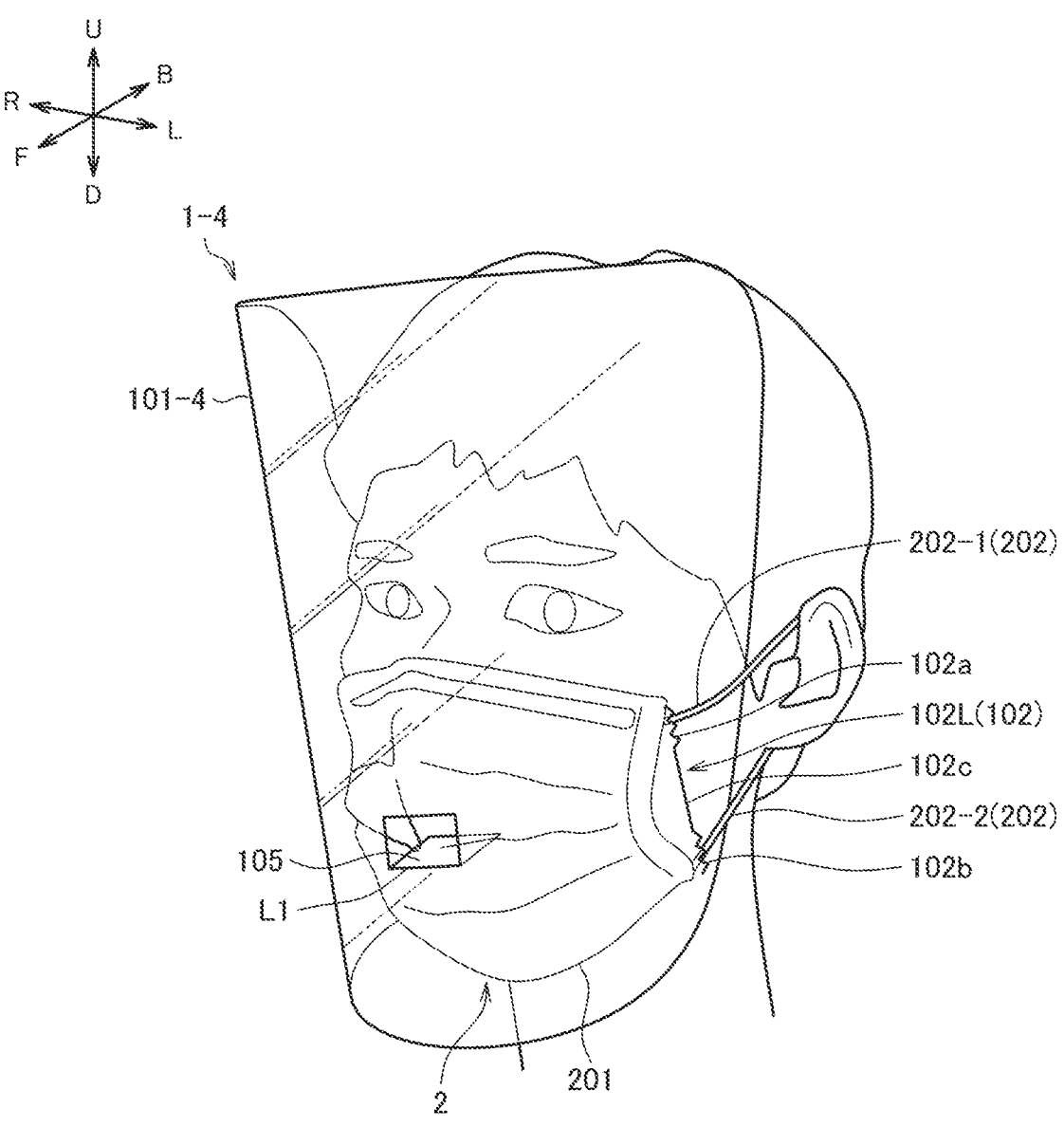
FIG. 8 is a perspective view showing a usage state of the face shield according to the fourth embodiment of the present invention.

When the face shield 1-4 is used, the folding part 105 is in a state folded along the folding line L1 toward the face of the user as shown in FIG. 8. Thus, the folding part 105 comes into contact with a portion of the mask 2 that covers the nose of the user or a region below the nose. The face shield 1-4 is thereby also supported at the folding part 105 in addition to the engagement parts 102a and 102b of the cut line 102 engaged with the straps 202 of the mask 2. Thus, the face shield 1-4 can be held and fixed more stably in a state in which the face of the user is covered by the face shield 1-4.

Further, the folding part 105 enables a gap in accordance with a protruding length of the folding part 105 to be reliably ensured between the face shield 1-4 and the face of the user. This can improve breathability between the face shield 1-4 and the face of the user, which can prevent the face shield 1-4 from fogging up, and can reduce a feeling of stuffiness of the user to improve the wearing property of the face shield 1-4.

Fifth Embodiment

A face shield 1-5 according to a fifth embodiment of the present invention will be described with reference to FIGS. 9 and 10.

Figure 9:
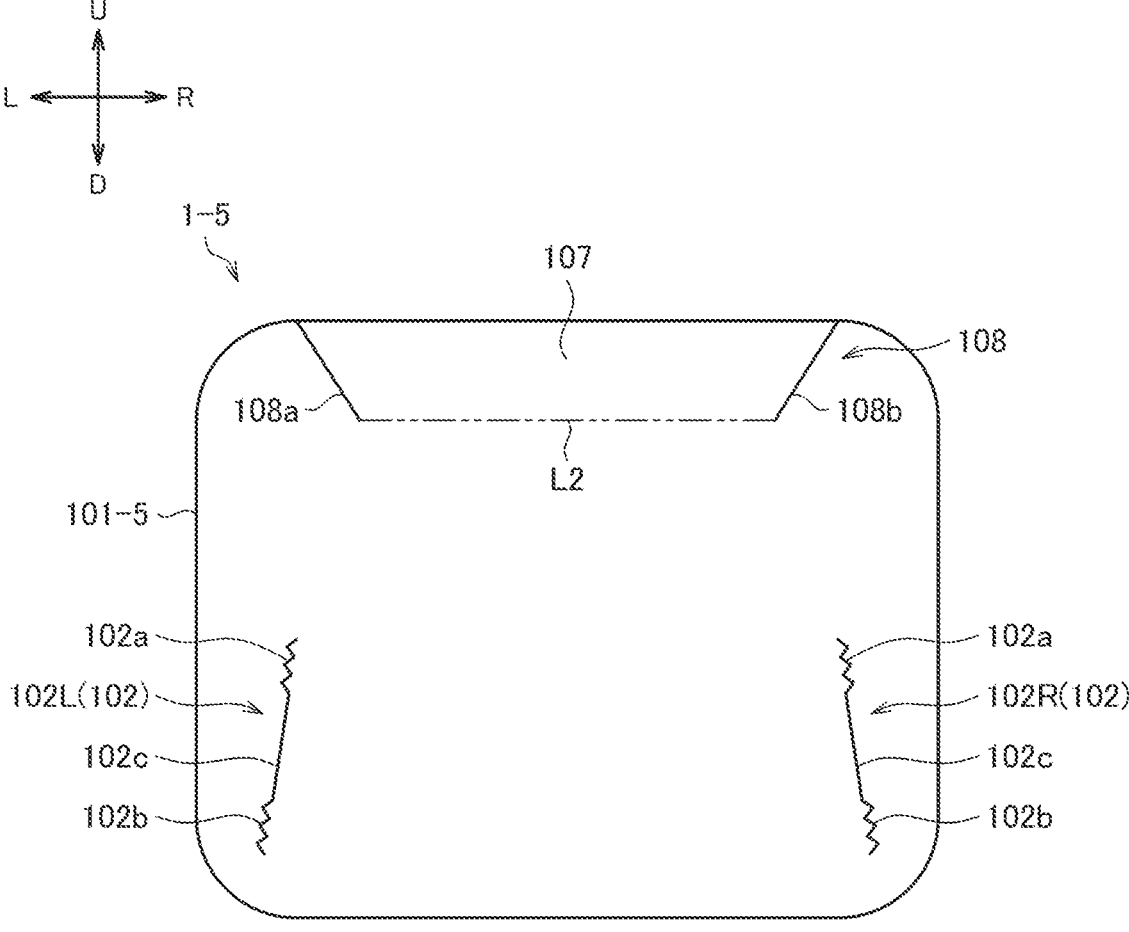
FIG. 9 is a plan view showing a face shield according to a fifth embodiment of the present invention.

FIG. 9 is a plan view showing the face shield 1-5. FIG. 10 is a perspective view showing a usage state of the face shield 1-5. FIG. 10 shows an example in which the face shield 1-5 is attached to the mask 2 of the ear-hung type. However, the face shield 1-5 can easily be combined and used with various masks similarly to the face shield 1-1.

The face shield 1-5 according to the fifth embodiment is different from the face shield 1-1 according to the first embodiment in that a folding part 107 that is foldable toward the face of a user is formed in the face shield 1-5 at a position to be opposed to the forehead or the frontal region of the head of the user.

As shown in FIG. 9, a cut part 108 for forming the folding part 107 is formed at an upper part of the face shield 1-5 (specifically, a film 101-5 that forms the face shield 1-5). The cut part 108 has a pair of left and right cut lines 108a and 108b. The cut lines 108a and 108b are open-type cut lines each having one end intersecting with an outer edge of the face shield 1-5 (that is, an outer edge of the film 101-5) and the other end arranged on an inner side of the face shield 1-5 (that is, an inner side relative to the outer edge of the film 101-5). The cut line 108a is formed on the left side of the upper part of the face shield 1-5. The cut line 108a is inclined downward in the right direction, and has a linear shape. The cut line 108b formed on the right side of the upper part of the face shield 1-5. The cut line 108b is inclined downward in the left direction, and has a linear shape. However, the shape of the cut lines 108a and 108b is not limited to this example, and may be an arc shape, for example. Alternatively, a structure may be adopted in which the upper part of the face shield 1-5 as a whole is just simply folded without providing the cut lines 108a and 108b.

The folding part 107 is a portion of the face shield 1-5 that can be deformed by being partially cut out along the cut lines 108a and 108b. The folding part 107 is foldable along a folding line L2 formed so as to connect the lower end of the cut line 108a and the lower end of the cut line 108b. The folding line L2 may be perforated so as to facilitate folding of the folding part 107. In addition, portions outside the cut lines 108a and 108b in the left-right direction and above the folding line L2 can also be deformed similarly to the folding part 107, and may be folded toward the face and used.

Figure 10:
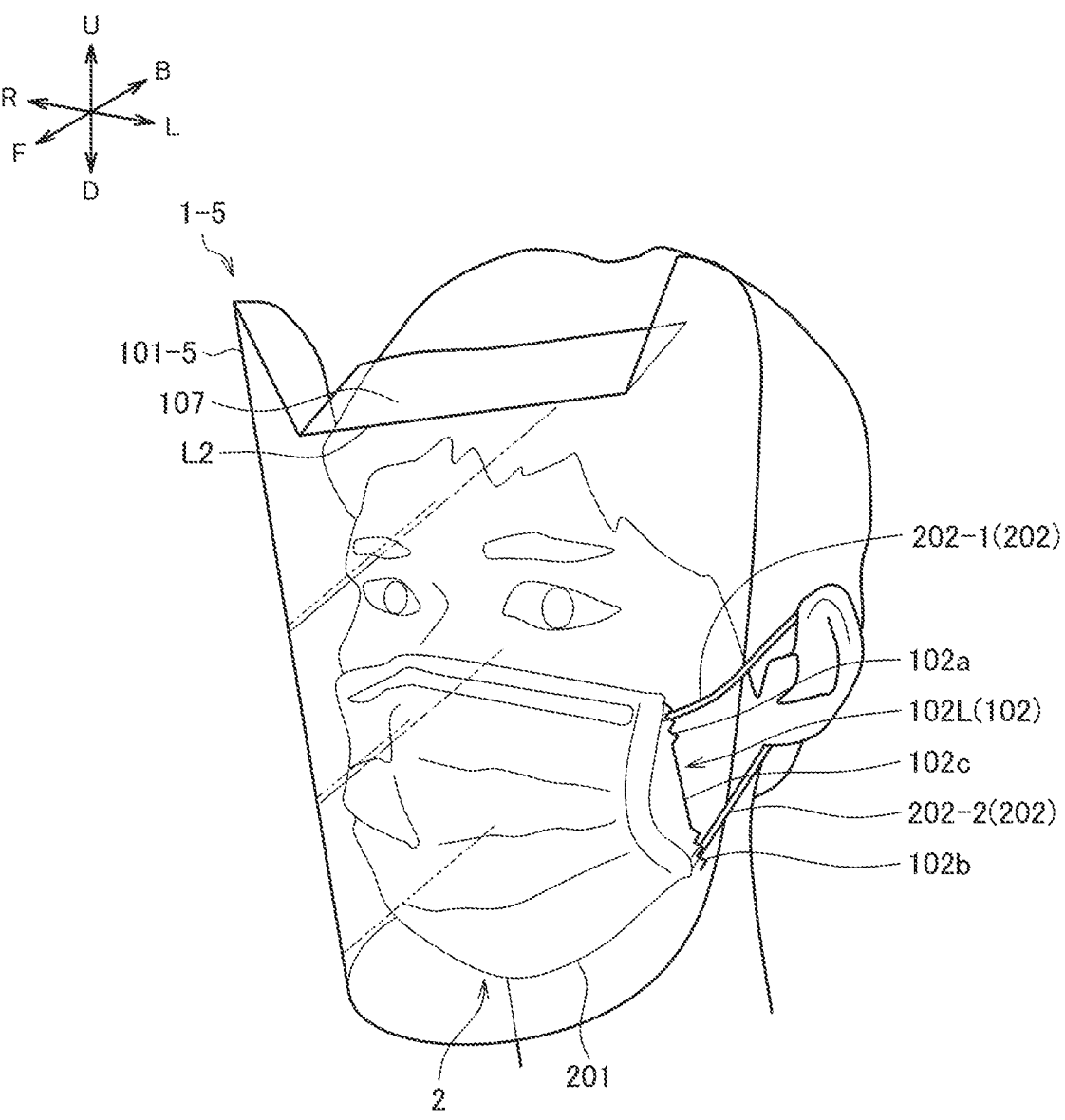
FIG. 10 is a perspective view showing a usage state of the face shield according to the fifth embodiment of the present invention.

When the face shield 1-5 is used, the folding part 107 is in a state folded along the folding line L2 toward the face of the user as shown in FIG. 10. Thus, the folding part 107 comes into contact with the forehead or the frontal region of the head of the user. The face shield 1-5 is thereby also supported at the folding part 107 in addition to the engagement parts 102a and 102b of the cut line 102 engaged with the straps 202 of the mask 2. Thus, the face shield 1-5 can be held and fixed more stably in a state in which the face of the user is covered by the face shield 1-5.

Further, the folding part 107 can prevent a foreign matter from entering the gap between the face shield 1-5 and the face of the user from above.

While the face shield 1-5 is provided with the folding part 107 at a position to be opposed to the forehead or the frontal region of the head of the user, a folding part (a portion that is foldable toward the face of the user) may also be provided similarly at a position to be opposed to the jaw of the user or at a position to be opposed to a region below the jaw. This can also prevent a foreign matter from entering the gap between the face shield 1-5 and the face of the user from below.

Sixth Embodiment

A face shield 1-6 according to a sixth embodiment of the present invention will be described with reference to FIGS. 11 and 12.

Figure 11:
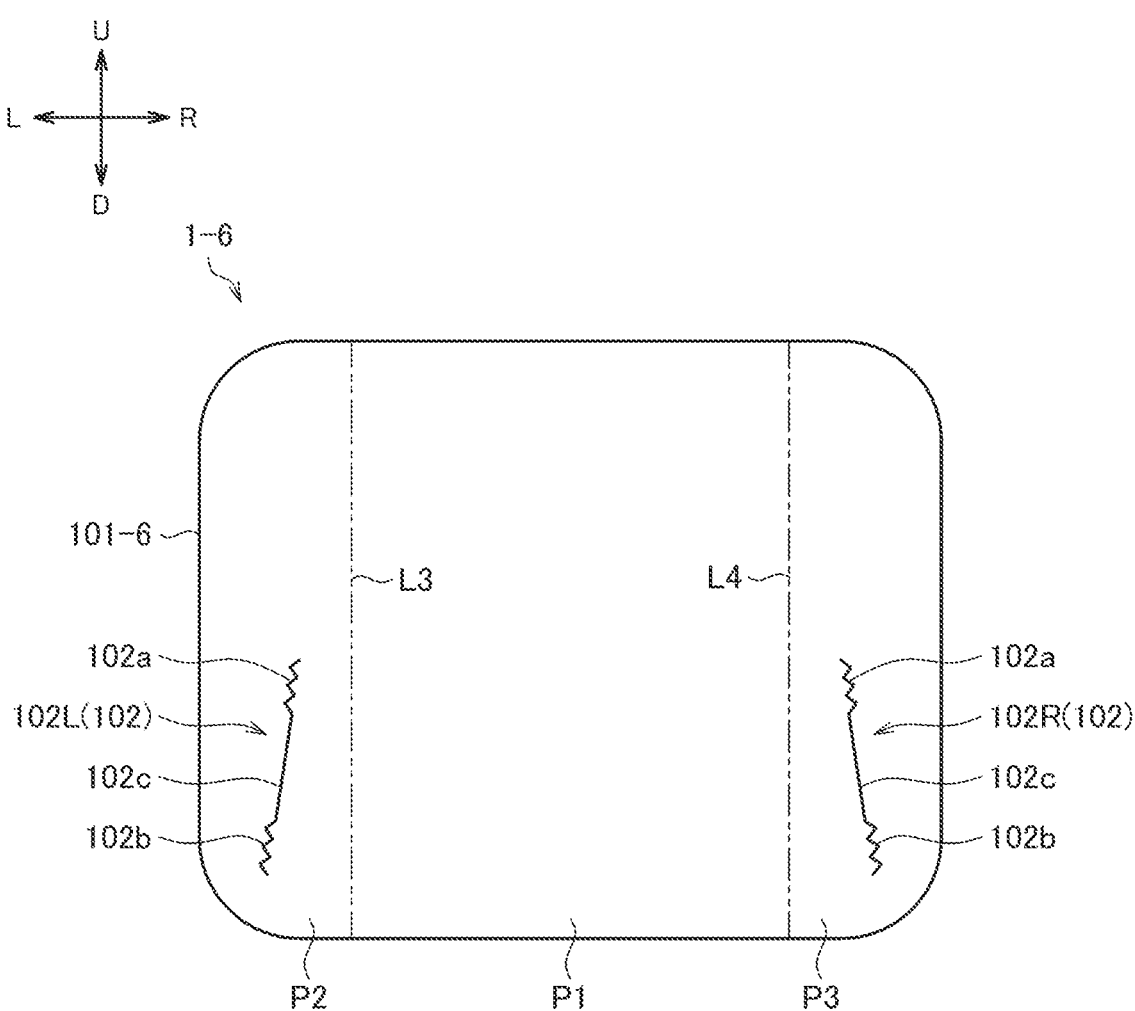
FIG. 11 is a plan view showing a face shield according to a sixth embodiment of the present invention.

FIG. 11 is a plan view showing the face shield 1-6. FIG. 12 is a perspective view showing a usage state of the face shield 1-6. FIG. 12 shows an example in which the face shield 1-6 is attached to the mask 2 of the ear-hung type. However, the face shield 1-6 can easily be combined and used with various masks similarly to the face shield 1-1.

The face shield 1-6 according to the sixth embodiment is different from the face shield 1-1 according to the first embodiment in that folding lines L3 and L4 are arranged on the face shield 1-6 between a portion P1 to be located on the front side of the face of a user and portions P2, P3 to be located on the lateral sides of the face of the user.

As shown in FIG. 11, a central part of the face shield 1-6 (specifically, a film 101-6 that forms the face shield 1-6) between the cut line 102L and the cut line 102R is the portion P1 (hereinafter referred to as "the front portion P1") to be located on the front side of the face of the user. A left part of the face shield 1-6 (specifically, the film 101-6 that forms the face shield 1-6) in which the cut line 102L is formed is the portion P2 to be located on the left lateral side of the face of the user (hereinafter referred to as "the left lateral portion P2"). A right part of the face shield 1-6 (specifically, the film 101-6 that forms the face shield 1-6) in which the cut line 102R is formed is the portion P3 to be located on the right lateral side of the face of the user (hereinafter referred to as "the right lateral portion P3").

The folding line L3 is formed between the front portion P1 and the left lateral portion P2. The folding line L4 is formed between the front portion P1 and the right lateral portion P3. The folding lines L3 and L4 are formed so as to extend in the up-down direction. The left lateral portion P2 is foldable along the folding line L3 with respect to the front portion P1. The right lateral portion P3 is foldable along the folding line L4 with respect to the front portion P1. The folding lines L3 and L4 may be perforated so as to facilitate folding of the left lateral portion P2 and the right lateral portion P3.

Figure 12:
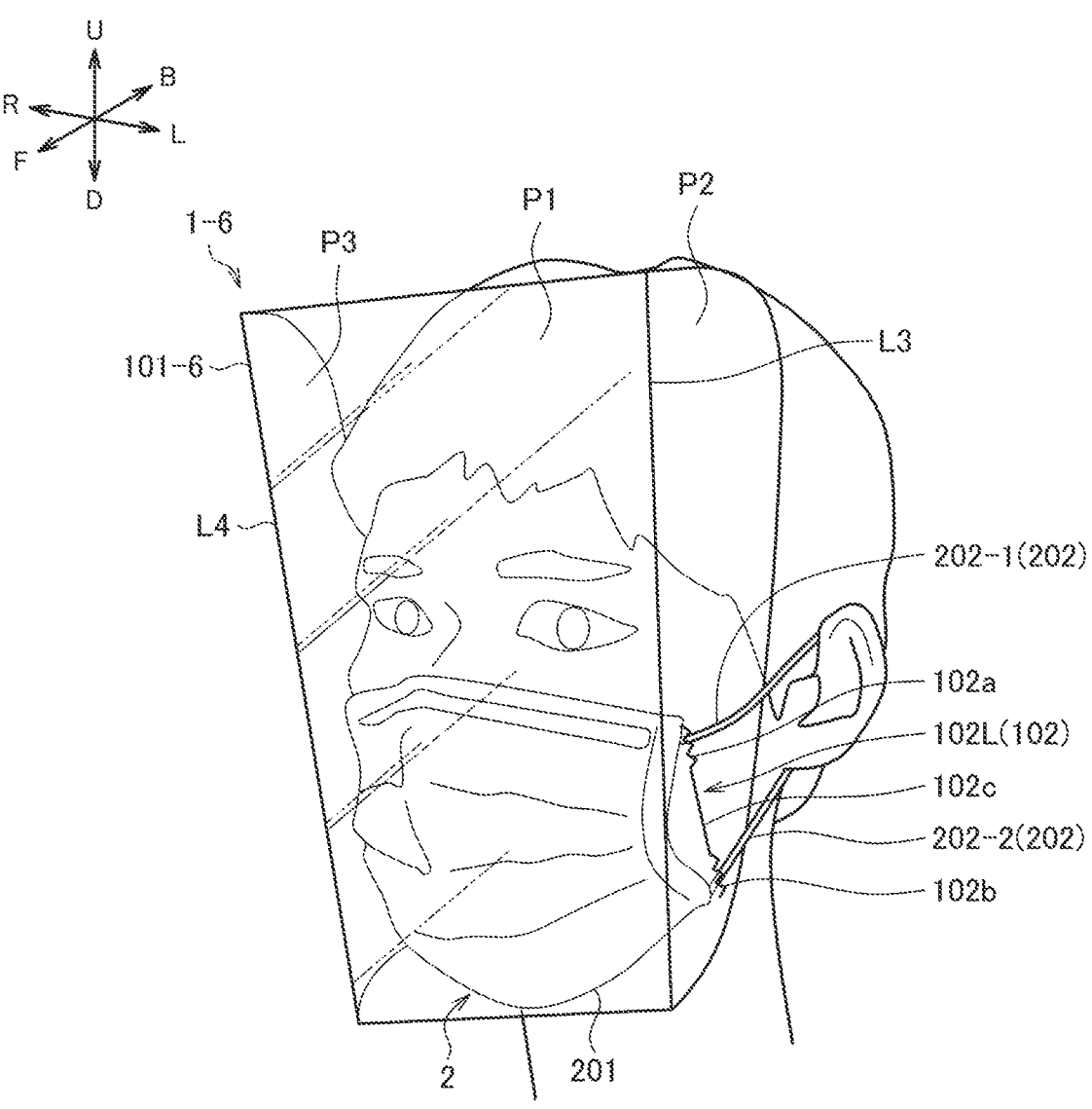
FIG. 12 is a perspective view showing a usage state of the face shield according to the sixth embodiment of the present invention.

When the face shield 1-6 is used, the left lateral portion P2 and the right lateral portion P3 are in a state folded along the folding lines L3 and L4 toward the face of the user as shown in FIG. 12. Thus, the front portion P1 of the face shield 1-6 is opposed to the face of the user in a state in which a planar shape is maintained. In the case in which the front portion P1 of the face shield 1-6 has a planar shape, reflection of external light can thereby be reduced as compared with a case in which the front portion P1 has a curved shape, which enables the field of view to be kept well.

Seventh Embodiment

A face shield 1-7 according to a seventh embodiment of the present invention will be described with reference to FIGS. 13 to 16.

Figure 13:
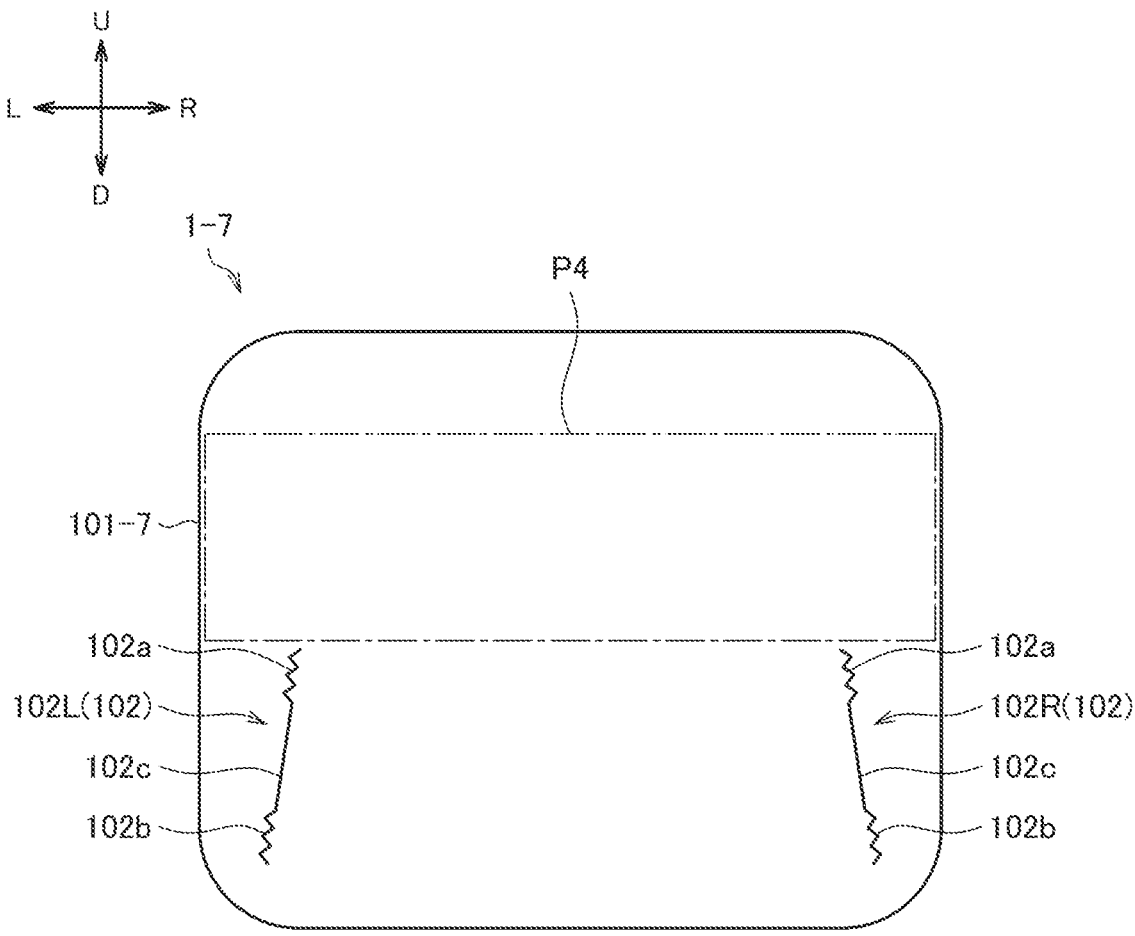
FIG. 13 is a plan view showing a face shield according to a seventh embodiment of the present invention.
Figure 14:
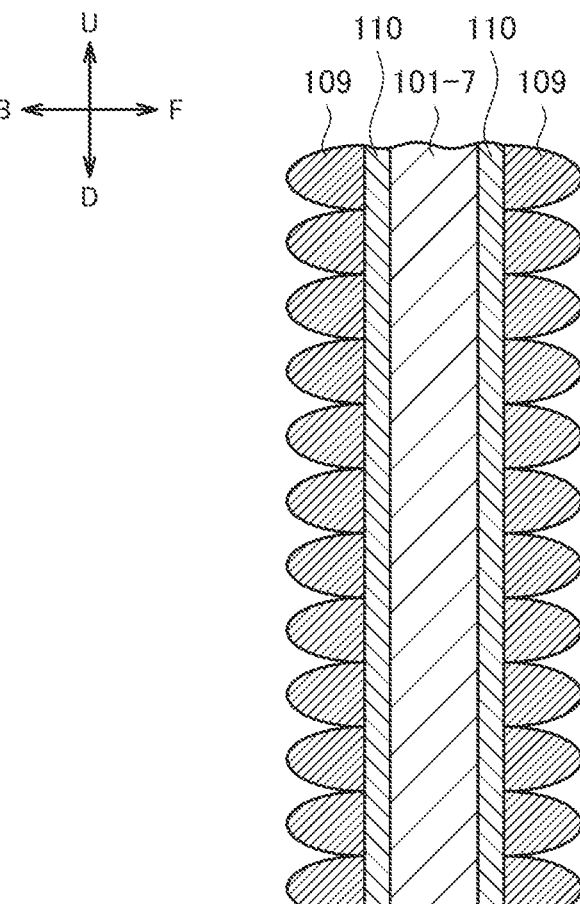
FIG. 14 is a partially magnified cross-sectional view showing the face shield according to the seventh embodiment of the present invention.

FIG. 13 is a plan view showing the face shield 1-7. FIG. 14 is a partially magnified cross-sectional view showing the face shield 1-7. Specifically, FIG. 14 is a cross-sectional view showing a cross section orthogonal to a surface of the face shield 1-7 in a field-of-view region P4 (see FIG. 13) of the face shield 1-7.

The face shield 1-7 according to the seventh embodiment is different from the face shield 1-1 according to the first embodiment in that an antireflection layer 109 (see FIG. 14) is provided.

The antireflection layer 109 may partially be provided only in the filed-of-view region P4 (see FIG. 13), for example, in the face shield 1-7 (specifically, a film 101-7 that forms the face shield 1-7). The filed-of-view region P4 is a region of the film 101-7 that mainly comes into the field of view of a user when the face shield 1-7 is used, and is a region above the cut lines 102L and 102R of the face shield 1-7, for example. However, the region in which the antireflection layer 109 is provided in the face shield 1-7 is not particularly limited, and the antireflection layer 109 may be provided in the whole region of the face shield 1-7, for example. In addition, from the perspective of increasing the antireflection effect, the antireflection layers 109 preferably are provided on both front and rear surfaces of the face shield 1-7 (specifically, the film 101-7 that forms the face shield 1-7). However, the antireflection layer 109 should only be provided on at least one of the surfaces of the face shield 1-7, and may be provided on only one of the surfaces of the face shield 1-7.

As shown in FIG. 14, the antireflection layers 109 are provided on both the surfaces of the film 101-7 with the interposition of base layers 110. The base layers 110 are provided to improve adhesion of the antireflection layers 109 to the film 101-7. The base layers 110 are optical layers formed integrally with the antireflection layers 109, for example, has transparency, and are formed by curing an energy beam-curable resin composition or the like similar to the antireflection layers 109. Note that the antireflection layers 109 may be formed directly on the surfaces of the film 101-7 without the interposition of the base layers 110. The antireflection layers 109 are provided to reduce reflection of external light and to improve the total transmittance of the face shield 1-7. Note that from the perspective of keeping the field of view of the user well as described above, the total transmittance of the face shield 1-7 should be more than or equal to 94.0%, and preferably more than or equal to 98.0%.

The antireflection layer 109 is composed of a micro concave-convex structure having a pitch smaller than or equal to a wavelength of visible light, for example. Concavities and convexities (convexities and concavities) of the micro concave-convex structure are formed periodically on the surfaces of the film 101-7 in vertical and lateral planar directions. An average period (average pitch) of the concavities and convexities of the micro concave-convex structure is less than or equal to the wavelength of visible light. The wavelength band of visible light ranges from 360 nm to 830 nm. In the present embodiment, the concavities and convexities of the micro concave-convex structure are regularly arrayed in a size less than or equal to the wavelength band of visible light. From such a perspective, the average period (average pitch) of the concavities and convexities shall be less than or equal to 350 nm. For example, the average period of the concavities and convexities preferably is more than or equal to 100 nm and less than or equal to 350 nm, more preferably is more than or equal to 120 nm and less than or equal to 280 nm, and still more preferably is 130 to 270 nm. Therefore, the micro concave-convex structure is what is called a moth-eye structure, and has an antireflection function. Herein, in a case in which the average period is less than 100 nm, it may be difficult to form the micro concave-convex structure, which is not preferable. Alternatively, in a case in which the average period exceeds 350 nm, diffracted light may be increased in intensity, so that external light may be diffracted at the surface on which the micro concave-convex structure is formed, which may degrade the antireflection effect.

Note that an average height of the micro concave-convex structure is not particularly restricted, and preferably is more than or equal to 100 nm and less than or equal to 300 nm, more preferably is more than or equal to 130 nm and less than or equal to 300 nm, and still more preferably is more than or equal to 150 nm and less than or equal to 230 nm, for example. The average height of the micro concave-convex structure is an arithmetic mean value of heights of a plurality of convexities constituting the micro concave-convex structure. For example, the heights of some of the convexities of the micro concave-convex structure are measured, and their arithmetic mean value can be calculated as the average height of the micro concave-convex structure. In addition, the convexities of the micro concave-convex structure extend in a direction vertical to the surfaces of the film 101-7. In addition, the convexities of the micro concave-convex structure may have any shape such as a pyramidal shape, a pillar shape, or a needle shape, for example.

In a case of manufacturing the micro concave-convex structure, a concave-convex pattern is transferred to a transfer material such as an energy beam-curable resin composition applied to a base material of the film 101-7 using a roll master exposure device on which a pattern in accordance with a moth-eye structure has been formed, and then the transfer material is cured, as will be described later.

Herein, a cured product of the transfer material may have hydrophilicity. The transfer material preferably contains one or more types of functional groups having hydrophilicity. Examples of such functional groups having hydrophilicity include a hydroxyl group, a carboxyl group, a carbonyl group, and the like.

In addition, an energy beam-curable resin product may have physical properties different from each other between both surfaces of the base material of the film 101-7. By differently using water repellency and hydrophilicity depending on the application of the face shield 1-7, for example, a function such as an anti-fogging function can be imparted to a specific surface.

A UV-curable resin composition, for example, preferably is used as the energy beam-curable resin composition. In addition, the energy beam-curable resin composition may contain a filler, a functional additive, and the like according to necessity. The UV-curable resin composition contains an acrylate and an initiator, for example. The UV-curable resin composition may contain a monofunctional monomer, a bifunctional monomer, a polyfunctional monomer, or the like, for example.

As described above, the face shield 1-7 according to the seventh embodiment is provided with the antireflection layer 109 on at least one of the surfaces of the film 101-7. This can reduce reflection of external light when the face shield 1-7 is used, which enables the field of view to be kept well.

Although antireflection coating (for example, AR coating) can be used as the antireflection layer 109, the moth-eye structure (see FIG. 14) composed of the micro concave-convex structure as described above preferably is used. In particular, the micro concave-convex structure having an average period less than or equal to the wavelength of visible light preferably is composed of resin having hydrophilicity as the antireflection layer 109. This enables high-level antireflection performance to be obtained, and enables an anti-fogging property to be added. The use of the moth-eye structure composed of the micro concave-convex structure can increase the antireflection performance of the face shield 1-7, so that the total transmittance of the face shield 1-7 can be more than or equal to 98.0%, for example. However, the use of another type of antireflection means such as Wet or Dry AR coating also enables a total transmittance of more than or equal to 94.0%, for example, to be obtained. Note that the AR coating is a technology for generating a thin film on a surface of a base material to cause interference of light, thereby reducing reflection light. The Wet AR coating includes spin coating, dipping, gravure coating, and the like. The Dry AR coating includes coating through use of the vacuum deposition method, the sputtering method, and the like.

Herein, a relationship between conditions for film surface treatment and a transmittance property will be described with reference to FIGS. 15 and 16.

FIG. 15 is a table showing various conditions for film surface treatment. Optical properties in surface treatment under each of Condition 1 to Condition 5 are shown in FIG. 15. Under Condition 1, moth-eye structures composed of micro concave-convex structures are formed on both sides of a film. Under Condition 2, both the sides of a film are subjected to the Wet AR coating. Under Condition 3, one side of a film is subjected to the Wet AR coating. Under Condition 4 and Condition 5, an antireflection layer is not provided on a film. In FIG. 15, respective rows correspond to optical properties under the respective conditions, and the material thickness (mm), total transmittance (%), and reflectance (%) are sequentially indicated from the left. Note that the base material of the films is polyethylene terephthalate. In addition, the total transmittance is measured with Haze Meter HM-150 manufactured by MURAKAMI COLOR RESEARCH LABORATORY CO., LTD. based on JIS K 7361.

Under Condition 1, the material thickness is 0.129 mm, the total transmittance is 98.3%, and the reflectance is 0.8%.

Under Condition 2, the material thickness is 0.125 mm, the total transmittance is 97.6%, and the reflectance is 2.2%.

Under Condition 3, the material thickness is 0.115 mm, the total transmittance is 94.7%, and the reflectance is 4.7%.

Under Condition 4, the material thickness is 0.101 mm, the total transmittance is 88.2%, and the reflectance is 11.5%.

Under Condition 5, the material thickness is 0.099 mm, the total transmittance is 90.6%, and the reflectance is 8.4%.

Figure 16:
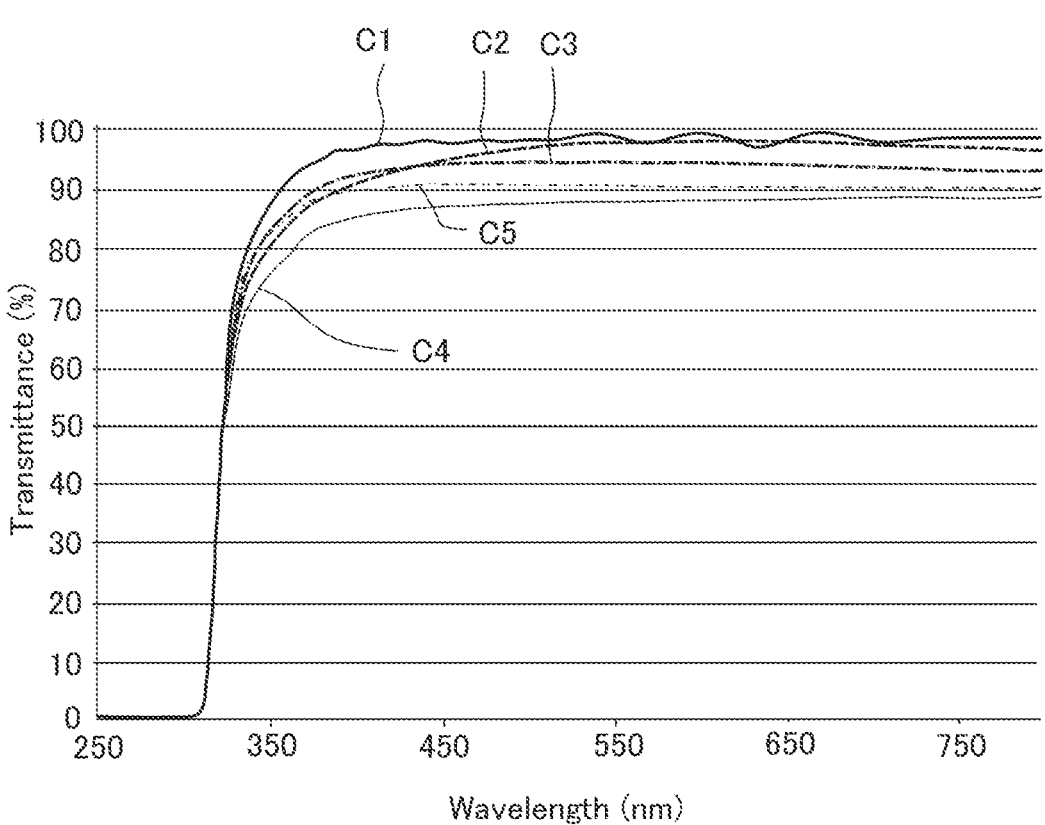
FIG. 16 is a diagram showing transmittance properties under various conditions for film surface treatment.

FIG. 16 is a diagram showing transmittance properties under the various conditions for film surface treatment. In FIG. 16, transmittance for light of each wavelength is indicated as a transmittance property for each of Condition 1 to Condition 5 shown in FIG. 15. Lines C1, C2, C3, C4, and C5 in FIG. 16 respectively indicate the transmittance properties under Condition 1, Condition 2, Condition 3, Condition 4, and Condition 5. FIG. 16 reveals that under Condition 2 and Condition 3 through use of the Wet AR coating, the transmittance is improved at each wavelength as compared with Condition 4 and Condition 5 in which no antireflection layer is provided. It is further revealed that under Condition 1 through use of the moth-eye structures composed of the micro concave-convex structures, the transmittance is improved at each wavelength as compared with Condition 2 and Condition 3 through use of the Wet AR coating.

Further, by forming the antireflection layers 109 composed of the micro concave-convex structures on both the sides of the base material of the film 101-7, more excellent antireflection performance can be imparted.

In addition, although not shown, a film laminate in which a plurality of transparent films, on each of which the antireflection layer 109 has been formed on both the sides or one side, are peelably laminated with an adhesive layer interposed between the respective transparent films may be used for the face shield 1-7 according to the present embodiment. By using such a film laminate in which the plurality of films are peelably laminated, contaminated films should only be peeled one by one even in a case in which there is not enough time to wipe off a contaminant or in a case in which it is originally not preferable to touch the contaminant because the contaminant is a hazardous material. Thus, the field of view can instantly be recovered, and further, the need to touch the hazardous material is eliminated. Note that the above-described plurality of transparent films may be laminated only on a portion to be opposed to the eyes.

Next, a method of manufacturing the face shield 1-7 including the antireflection layers 109 composed of the micro concave-convex structures on the surfaces of the film 101-7 will be described.

In the case of manufacturing the face shield 1-7, a micro concave-convex structure (moth-eye structure) is first formed on a surface of a film roll to be the material of the film 101-7 using an energy beam-curable resin composition such as a UV curing resin, for example. At this time, a roll master exposure device on which a concave-convex pattern corresponding to the micro concave-convex structure has been formed is used to transfer the concave-convex pattern to the energy beam-curable resin composition on a surface of the film 101-7, thereby forming the micro concave-convex structure. Thereafter, a contour of the face shield 1-7 and the shapes of the cut lines 102L and 102R are formed. Each step of such a manufacturing method will be described below.

Preparation of Master

First, a master for micro concavities and convexities having an inverted shape of the micro concave-convex structure of the antireflection layer 109 is prepared. The master for micro concavities and convexities is a master for use in the nano-imprinting method, which may be a cylindrical or pillar-shaped roll master, for example, or may be a master having another shape (for example, a planar shape). In the case of using the roll master, the micro concave-convex structure of the master for micro concavities and convexities can seamlessly be transferred to the base material of the film 101-7 by the roll-to-roll method. The pillar surface or cylindrical surface of the roll master serves as a molding surface for molding the concave-convex structure on the surface of the base material of the film 101-7. On this molding surface, a predetermined micro concave-convex structure is two-dimensionally arrayed by dry etching, wet etching, or the like, for example. Glass, for example, can be used as the material of the roll master, but the material of the roll master is not particularly limited to this material. The micro concave-convex structure arranged on the molding surface of the roll master and the micro concave-convex structure (moth-eye structure) formed on the surface of the base material of the film 101-7 described above have an inverted concave-convex relationship.

Transfer Step

Then, uncured resin is applied to the surface of the base material of the film 101-7 to form an uncured resin layer (a transfer material layer). The uncured resin layer is composed of uncured curable resin such as UV curing resin. Then, the roll master is brought into close contact with the uncured resin layer of the film 101-7 by the roll-to-roll method, for example. Further, the uncured resin layer is irradiated with an energy beam such as ultraviolet rays from an energy beam source, so that the uncured resin is cured. Note that the energy beam source is not particularly limited as long as an energy beam such as an electron beam, ultraviolet light, infrared light, laser beam, visible light, ionization radiation (such as X-rays, α-rays, β-rays, or γ-rays), microwave, or radio-frequency wave can be discharged.

Thereafter, the base material integrated with the cured uncured resin is peeled from the roll master. The micro concave-convex structure on the roll master is thereby transferred to the surface of the base material of the film 101-7, so that the micro concave-convex structure (moth-eye structure) to be the antireflection layer 109 is formed on the surface of the base material of the film 101-7. The micro concave-convex structure on the surface of the base material of the film 101-7 has an inverted shape of the micro concave-convex structure of the roll master.

Note that in the case of forming the antireflection layers 109 composed of the micro concave-convex structures on both the sides of the base material of the film 101-7, the micro concave-convex structure should also be transferred to a surface on the other side of the base material similarly to the foregoing. In addition, a protective film may be pasted to the surface of the film 101-7 obtained in the above-described transfer step. This can prevent the micro concave-convex structure of the film 101-7 from being broken in a subsequent step, during transport, or the like.

Shield Molding Process Step

The film 101-7 obtained in the above-described step is cut up into a predetermined shape of the face shield 1-7, and is subjected to processing of forming the cut lines 102 described above, thereby molding the face shield 1-7. A cutting machine, a laser processing device, a punching press device, or the like as numerically controlled can be used for a molding process for forming the cut lines 102 and cutting into the predetermined shape. The use of punching press processing enables forming processing of the cut lines 102 and cutting into the predetermined shape to be performed in one step, which is suitable.

Eighth Embodiment

A face shield 1-8 according to an eighth embodiment of the present invention will be described with reference to FIG. 17.

Figure 17:
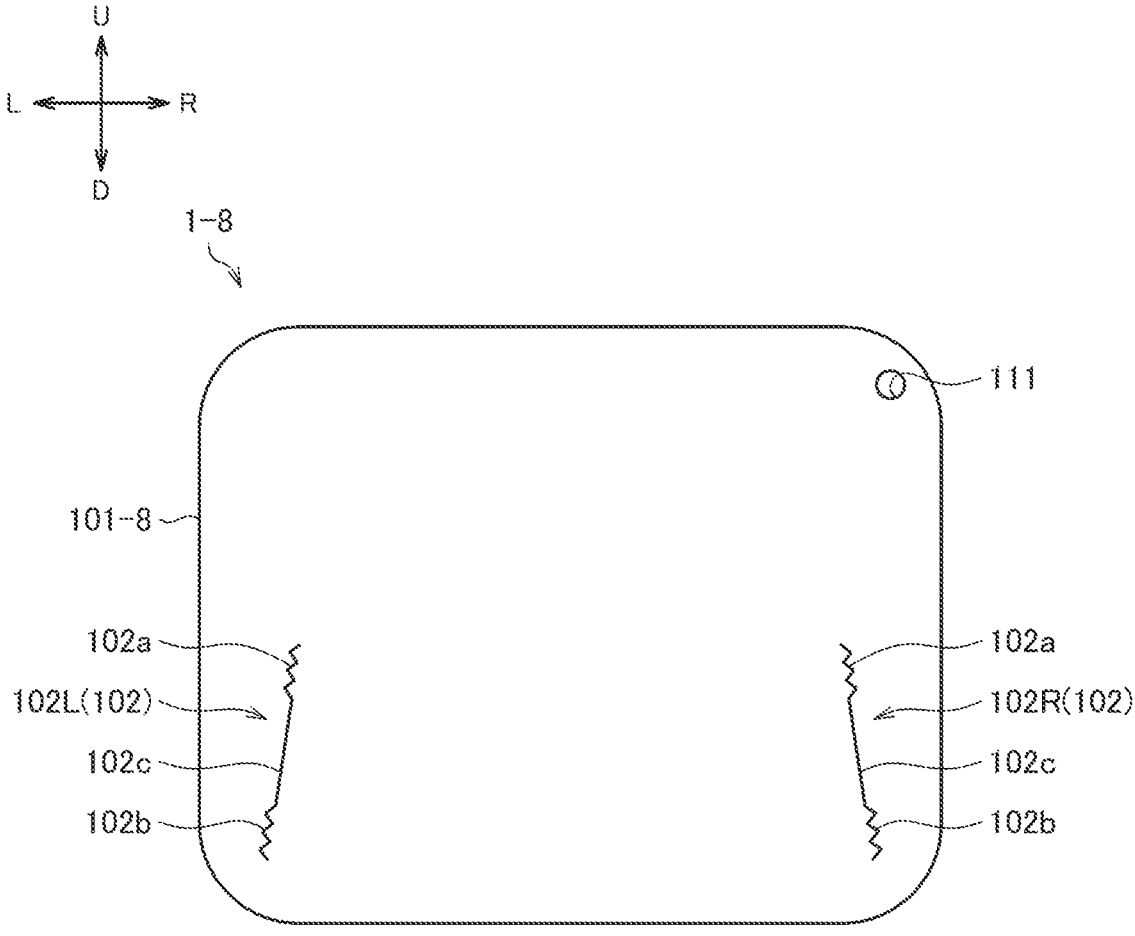
FIG. 17 is a plan view showing a face shield according to an eighth embodiment of the present invention.

FIG. 17 is a plan view showing the face shield 1-8.

The face shield 1-8 according to the eighth embodiment is different from the face shield 1-1 according to the first embodiment in that a through-hole 111 through which a hook for cleaning and drying is to be inserted is formed.

As shown in FIG. 17, the through-hole 111 is formed in the vicinity of an outer edge of the face shield 1-8 (specifically, a film 101-8 that forms the face shield 1-8). The through-hole 111 is arranged at a right upper end of the face shield 1-8. The through-hole 111 has a circular shape. However, the shape of the through-hole 111 is not limited to this example, and may have an oval shape or a polygonal shape, for example. Alternatively, an arc-shaped cut line may be formed in the face shield 1-8 instead of the through-hole 111, and a through-part formed by folding a portion partially cut out by the cut line may function as a portion through which the hook for cleaning and drying is inserted. Furthermore, a hook-shaped notch may be provided at an outer edge part of the face shield 1-8, and the notch may function as a portion through which the hook for cleaning and drying is inserted. In addition, the arrangement of the through-hole 111 is not limited to the example shown in FIG. 17. For example, the through-hole 111 may be arranged on a left upper end, or may be arranged on the central side of an upper end.

The hook is inserted through the through-hole 111 when the face shield 1-8 is cleaned and dried. For example, the face shield 1-8 is immersed into a cleaning liquid and cleaned in a state being hung from the hook. In addition, the face shield 1-8 is dried in the state being hung from the hook.

The face shield 1-8 having been contaminated can thereby be cleaned and dried for reuse.

Ninth Embodiment

A face shield 1-9 according to a ninth embodiment of the present invention will be described with reference to FIG. 18.

Figure 18:
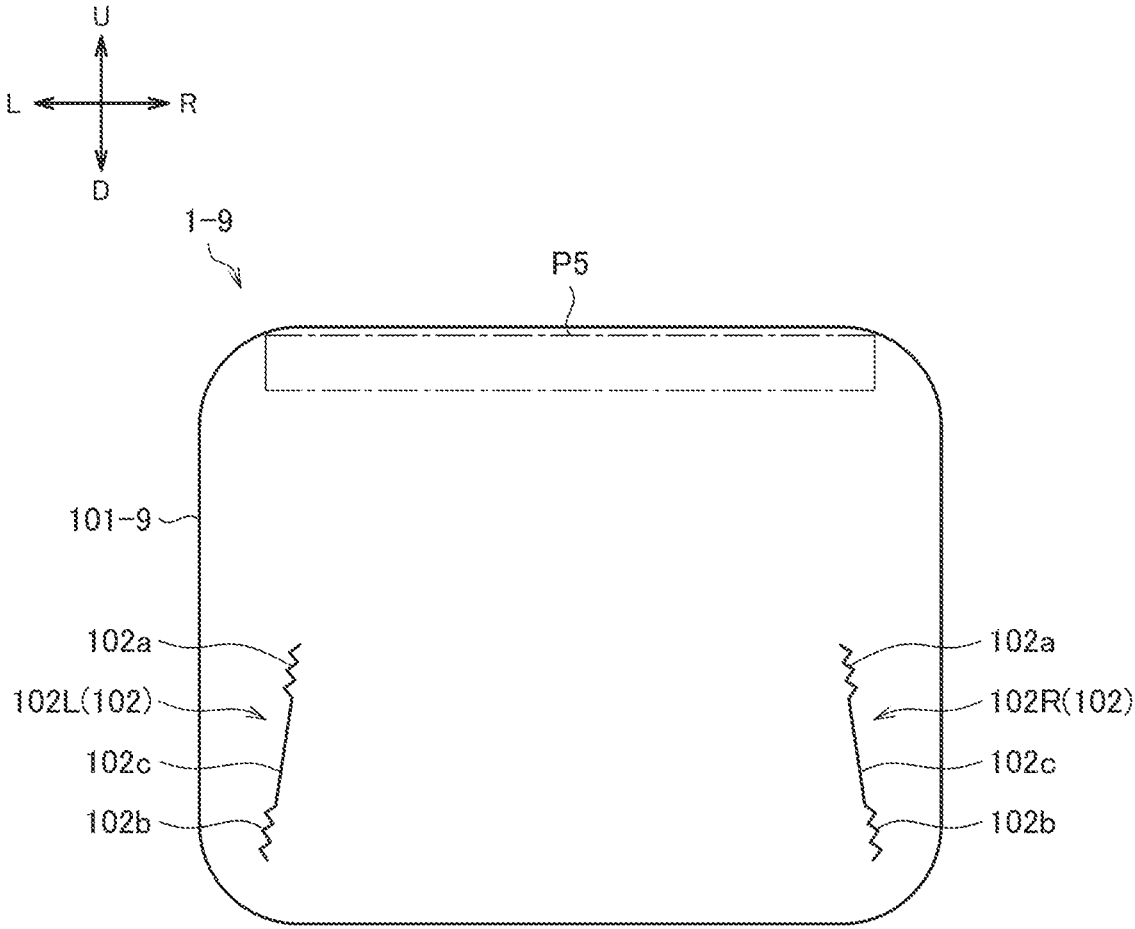
FIG. 18 is a plan view showing a face shield according to a ninth embodiment of the present invention.

FIG. 18 is a plan view showing the face shield 1-9.

The face shield 1-9 according to the ninth embodiment is different from the face shield 1-1 according to the first embodiment in that a mark for facilitating finding of the face shield 1-9 is formed.

For example, the above-described mark is formed in an upper region P5 (see FIG. 18) of the face shield 1-9. Examples of the mark formed in the upper region P5 include the name of a manufacturer, a pattern that shines by reflecting light, or the like. However, the mark formed on the face shield 1-9 is not limited to this example, and may be any character, figure, or symbol, or a combination thereof, for example. In addition, a position at which the mark is formed on the face shield 1-9 may be other than the upper region P5, and may be a left region or a right region, for example. A method of forming the above-described mark is not limited as long as the mark is visually recognizable. The above-described mark may be formed by a cut line, or may be formed by forming micro concavities and convexities on the surface of the face shield 1-9 to reflect, diffract, or interfere with light. Alternatively, the above-described mark may be formed by a slit having an opening, or may be formed by ink, a seal, or the like.

As described above, the face shield 1-9 is made of a thin transparent film having high transparency. Thus, a situation may arise in which the face shield 1-9 put on a place such as a table, for example, is difficult to visually recognize. In addition, a state may arise in which if a mounting position of the face shield 1-9 is displaced when mounting the face shield 1-9, for example, a user is not aware of the displacement. Thus, forming the mark on the face shield 1-9 can facilitate visual recognition of the face shield 1-9, resulting in convenient handling. Mounting at a proper position enables an infection preventing property to be maintained.

Tenth Embodiment

A face shield 1-10 according to a tenth embodiment of the present invention will be described with reference to FIGS. 19 and 20.

Figure 19:
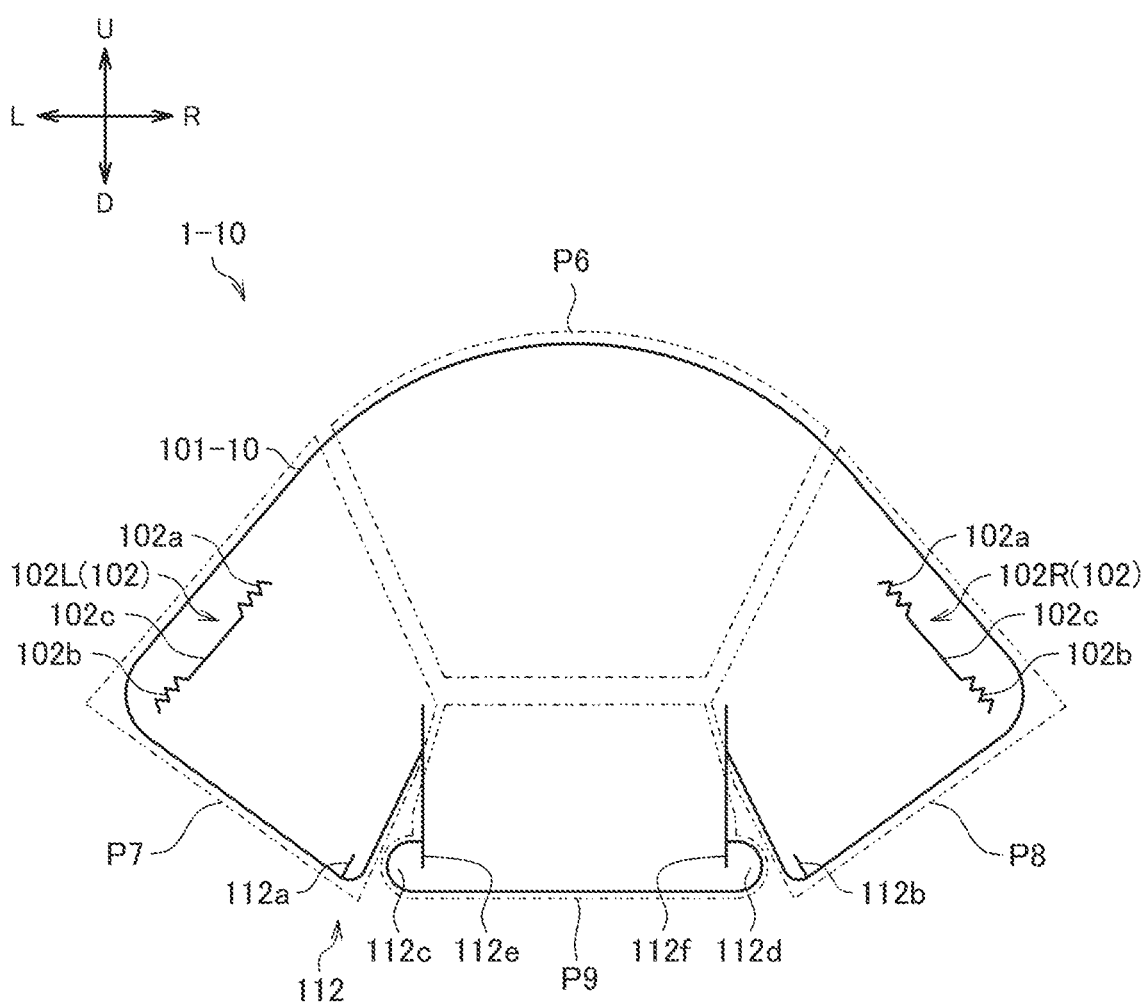
FIG. 19 is a plan view showing a face shield according to a tenth embodiment of the present invention.

FIG. 19 is a plan view showing the face shield 1-10. FIG. 20 is a perspective view showing a usage state of the face shield 1-10. FIG. 20 shows an example in which the face shield 1-10 is attached to the mask 2 of the ear-hung type. However, the face shield 1-10 can easily be combined and used with various masks similarly to the face shield 1-1.

The face shield 1-10 according to the tenth embodiment is different from the face shield 1-1 according to the first embodiment in that the face shield 1-10 has a formative structure 112 that can be formed into a shape that tapers with distance from the face of a user.

As shown in FIG. 19, the face shield 1-10 (specifically, a film 101-10 that forms the face shield 1-10) has a portion P6 to be located on the front side of the face of the user and opposed to the eyes, a portion P7 to be located on the left lateral side of the face of the user, a portion P8 to be located on the right lateral side of the face of the user, and a portion P9 to be located on the front side of the face of the user and opposed to the respiratory organs.

In the plan view shown in FIG. 19, the portion P6 is an upper part of the face shield 1-10, and has a fan shape with the center arranged on the lower side. The portion P7 is a left part of the face shield 1-10, and is formed so as to extend from the portion P6 in a lower left direction. The cut line 102L is formed in the portion P7. The portion P8 is a right part of the face shield 1-10, and is formed so as to extend from the portion P6 in a lower right direction. The cut line 102R is formed in the portion P8. The portion P9 is a lower part of the face shield 1-10, and is formed between the portion P7 and the portion P8 so as to extend from the portion P6 in the down direction. The portion P9 is spaced from each of the portion P7 and the portion P8 in the left-right direction.

The formative structure 112 includes a cut line 112*a* formed in the portion P7, a cut line 112*b* formed in the portion P8, and projecting parts 112*c*, 112*d* and cut lines 112*e*, 112*f* formed in the portion P9. The cut lines 112*a*, 112*b*, 112*e*, and 112*f* are open-type cut lines each having one end intersecting with an outer edge of the face shield 1-10 (that is, an outer edge of the film 101-10), and the other end arranged on an inner side of the face shield 1-10 (that is, an inner side relative to the outer edge of the film 101-10).

The cut line 112*a* intersects with an outer edge of the portion P7 on a lower left side, is formed close to the portion P9 in the portion P7, and extends in the upper right direction. The cut line 112*b* intersects with an outer edge of the portion P8 on a lower right side, is formed close to the portion P9 in the portion P8, and extends in the upper left direction. The projecting part 112*c* projects from the lower end of the portion P9 to the left side. The cut line 112*e* intersects with an upper portion of an outer edge of the projecting part 112*c*, and extends in the down direction. The projecting part 112*d* projects from a lower end of the portion P9 to the right side. The cut line 112*f* intersects with an upper portion of an outer edge of the projecting part 112*d*, and extends in the down direction.

Figure 20:
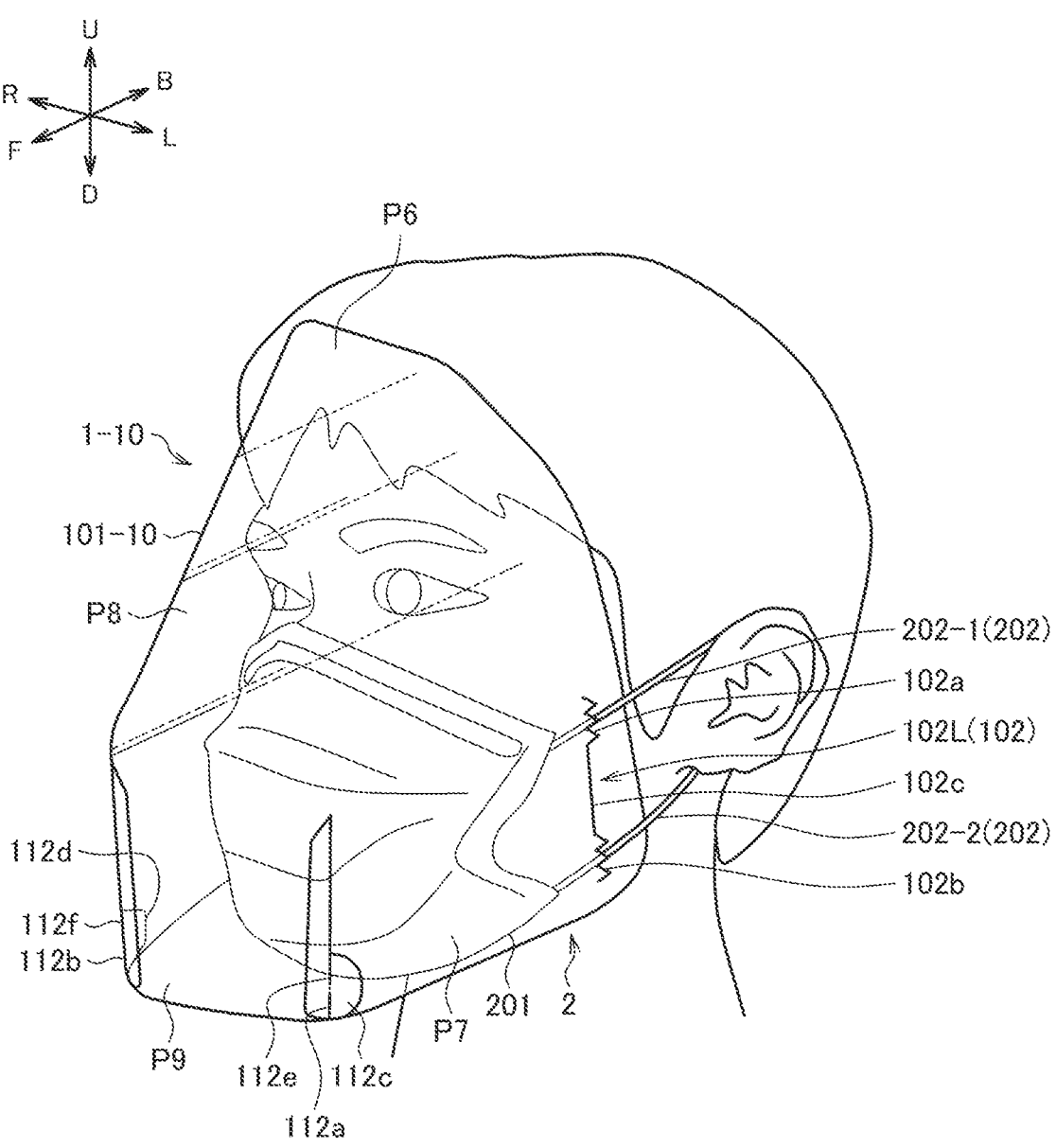
FIG. 20 is a perspective view showing a usage state of the face shield according to the tenth embodiment of the present invention.

As shown in FIG. 20, in the case of forming the face shield 1-10 using the formative structure 112, the projecting part 112*c* in the portion P9 is put into the cut line 112*a* in the portion P7 in a state in which the cut line 112*a* in the portion P7 and the cut line 112*e* in the portion P9 are coaxial. In addition, the projecting part 112*d* in the portion P9 is put into the cut line 112*b* in the portion P8 in a state in which the cut line 112*b* in the portion P8 and the cut line 112*f* in the portion P9 are coaxial. In this manner, the face shield 1-10 is formed into a three-dimensional spatial shape that tapers with distance from the face of the user. However, the formative structure 112 is not particularly limited to the above-described example as long as the face shield can be formed into a shape that tapers with distance from the face of the user. Various structures such as a formative structure 132 according to an eighteenth embodiment which will be described later, for example, may be adopted as such a structure.

In the face shield 1-1 according to the first embodiment shown in FIG. 2, the film 101-1 has a spatial shape simply curved in the left-right direction. In contrast, in the face shield 1-10 according to the tenth embodiment shown in FIG. 20, the film 101-10 is formed into the three-dimensional spatial shape that tapers with distance from the face of the user. The tapering three-dimensional spatial shape is achieved by forming the four portions P6, P7, P8, and P9 using the formative structure 112 such that the planar directions of the four portions P6, P7, P8, and P9 of the film 101-10 described above are directed to directions different from one another.

The portion P6 of the face shield 1-10 comes into contact with the forehead of the user when in use. The face shield 1-10 is thereby also supported at the portion P6 in addition to the engagement parts 102a and 102b of the cut line 102 engaged with the straps 202 of the mask 2. Thus, the face shield 1-10 can be held and fixed more stably when in use.

Further, the portion P6 prevents a foreign matter from entering a gap between the face shield 1-10 and the face of the user from above.

Further, since the portion P6 of the face shield 1-10 coming into contact with the forehead of the user prevents light from above from entering the gap between the face shield 1-10 and the face of the user, which prevents light from above from being reflected by the face shield 1-10 toward the user. Thus, the field of view can be kept well.

Further, since the face shield 1-10 has the center of gravity closer to the user than the face shield 1-1 according to the first embodiment, for example, the face shield 1-10 can be held and fixed more stably when in use.

In the tenth embodiment, the spatial shape shown in FIG. 20 is formed by connecting the portion P7 and the portion P9, and the portion P8 and the portion P9 with the formative structure 112. On the other hand, since there are a plurality of planar shapes when a spatial shape is developed, a similar spatial shape can also be formed from a shape other than the shape in the plan view shown in FIG. 19. For example, the spatial shape shown in FIG. 20 can also be formed by arranging a formative structure in the vicinity of a portion between the portion P6 and the portion P7 and a portion between the portion P6 and the portion P8 instead of the formative structure 112 arranged in the vicinity of a spaced portion between the portion P7 and the portion P9 and a spaced portion between the portion P8 and the portion P9.

In addition, in the tenth embodiment, the spaced portion between the portion P7 and the portion P9 and the spaced portion between the portion P8 and the portion P9 disappear without any gaps by means of the formative structure 112, however, such a shape that gaps are left after forming the spatial shape, for example, can also be adopted to cause the gaps to serve as through-holes as those of the third embodiment.

In addition, the tenth embodiment has a structure in which the portion P6 of the face shield 1-10 comes into contact with the forehead of the user, so that the portion P6 prevents a foreign matter from entering the gap between the face shield 1-10 and the face of the user from above, however, a structure in which a vertically-inverted form, for example, prevents a foreign matter from entering from below can also be adopted.

Eleventh Embodiment

A face shield 1-11 according to an eleventh embodiment of the present invention will be described with reference to FIG. 21.

Figure 21:
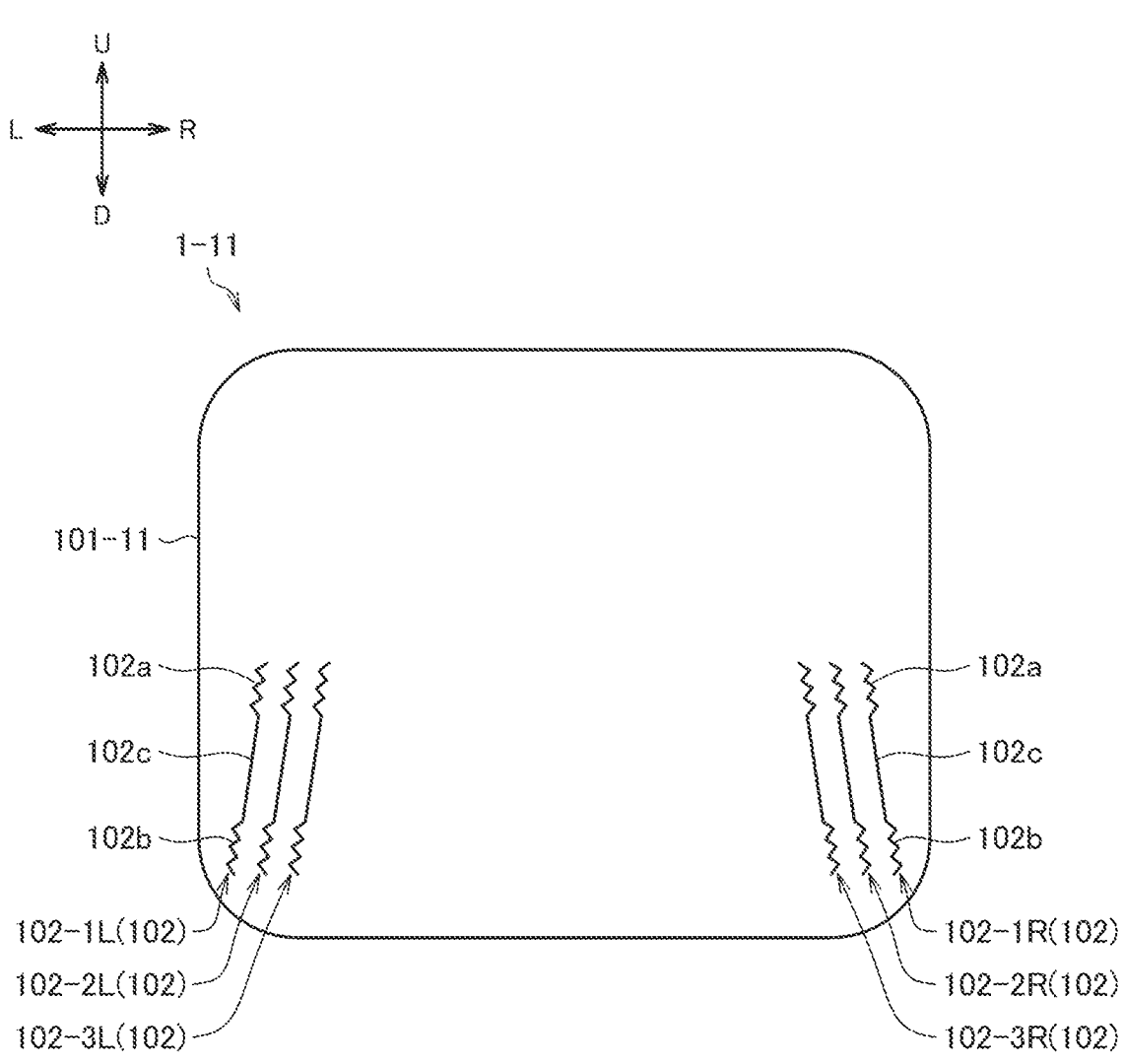
FIG. 21 is a plan view showing a face shield according to an eleventh embodiment of the present invention.

FIG. 21 is a plan view showing the face shield 1-11.

The face shield 1-11 according to the eleventh embodiment is different from the face shield 1-1 according to the first embodiment in that a plurality of pairs of the cut lines 102 are formed in both left and right parts of the face shield 1-11.

As shown in FIG. 21, three pairs of the cut lines 102 (cut lines 102-1L, 102-1R, cut lines 102-2L, 102-2R, and cut lines 102-3L, 102-3R) are formed in both the left and right parts of the face shield 1-11 (specifically, a film 101-11 that forms the face shield 1-11). The cut line 102-1L and the cut line 102-1R form the first pair. The cut line 102-2L and the cut line 102-2R form the second pair. The cut line 102-3L and the cut line 102-3R form the third pair. However, the number of pairs of the cut lines 102 may be two, or four or more. In addition, the engagement parts 102a and 102b may have a sawtooth shape as shown in FIG. 21, or may be replaced by a branched shape (see engagement parts 113a and 113b in FIG. 23), a curved shape (see engagement parts 114a and 114b in FIG. 24), or a changeable part (see a changeable part 116 in FIG. 27 and the like) which will be described later. In addition, the engagement parts may have different shapes from pair to pair.

The cut lines 102-1L, 102-2L, and 102-3L are formed on the lower side of the left part of the film 101-11. The cut lines 102-1L, 102-2L, and 102-3L are arrayed in this order from the left side to the right side. The cut lines 102-1R, 102-2R, and 102-3R are formed on the lower side of the right part of the film 101-11. The cut lines 102-1R, 102-2R, and 102-3R are arrayed in this order from the right side to the left side. Thus, the interval between the paired cut lines 102 is different from pair to pair. Specifically, the interval between the cut line 102-1L and the cut line 102-1R that form the first pair is the largest. The interval between the cut line 102-2L and the cut line 102-2R that form the second pair is the second largest. The interval between the cut line 102-3L and the cut line 102-3R that form the third pair is the smallest.

As described above, in the face shield 1-11 according to the eleventh embodiment, a plurality of pairs of the cut lines 102 are formed. Therefore, by selecting a pair of the cut lines 102 to be used in accordance with the size of the face of a user or the mask, the gap between the face shield 1-11 and the mask 2 can be adjusted, and the face shield 1-11 can fit well to the face of the user.

A user whose face is large, for example, can use the cut lines 102-1L and 102-1R that form the first pair to maintain the gap between the face shield 1-11 and the mask 2, and cause the face shield 1-11 to fit well to his/her face. In this case, the two straps 202-1 and 202-2 extending from the left side of the mask 2 are inserted through the cut line 102-1L, and the two straps 202-3 and 202-4 extending from the right side of the mask 2 are inserted through the cut line 102-1R.

Alternatively, a user whose face is small, for example, can use the cut lines 102-3L and 102-3R that form the third pair to maintain the gap between the face shield 1-11 and the mask 2, and cause the face shield 1-11 to fit well to his/her face. In this case, the two straps 202-1 and 202-2 extending from the left side of the mask 2 are inserted through the cut line 102-3L, and the two straps 202-3 and 202-4 extending from the right side of the mask 2 are inserted through the cut line 102-3R.

Twelfth Embodiment

A face shield 1-12 according to a twelfth embodiment of the present invention will be described with reference to FIG. 22.

Figure 22:
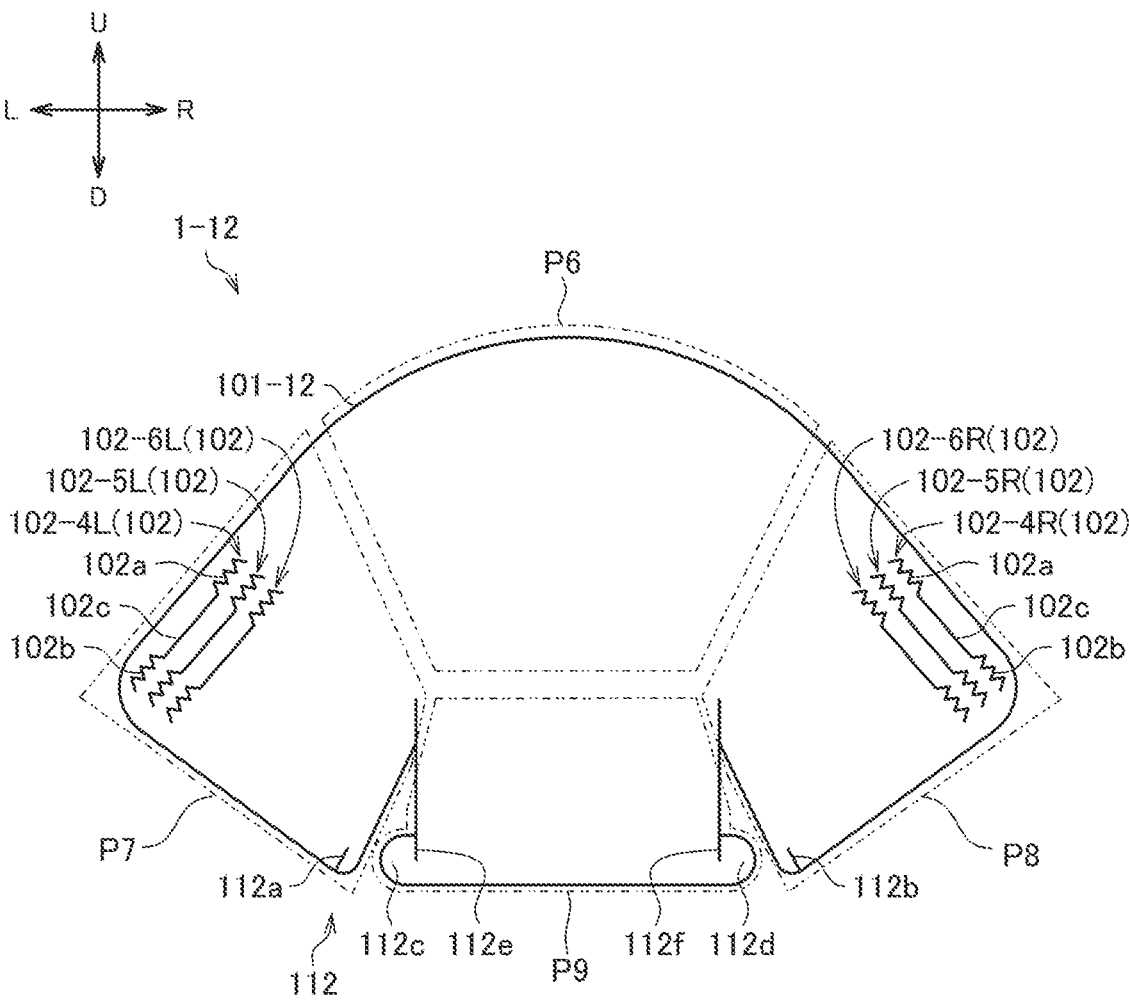
FIG. 22 is a plan view showing a face shield according to a twelfth embodiment of the present invention.

FIG. 22 is a plan view showing the face shield 1-12.

The face shield 1-12 according to the twelfth embodiment is different from the face shield 1-10 according to the tenth embodiment in that a plurality of pairs of the cut lines 102 are formed in both the left and right parts of the face shield 1-12.

As shown in FIG. 22, three pairs of the cut lines 102 (cut lines 102-4L, 102-4R, cut lines 102-5L, 102-5R, and cut lines 102-6L, 102-6R) are formed in both the left and right parts of the face shield 1-12 (specifically, a film 101-12 that forms the face shield 1-12). The cut line 102-4L and the cut line 102-4R form the first pair. The cut line 102-5L and the cut line 102-5R form the second pair. The cut line 102-6L and the cut line 102-6R form the third pair. However, the number of pairs of the cut lines 102 may be two, or four or more.

The cut lines 102-4L, 102-5L, and 102-6L are formed in the portion P7 which is the left part of the film 101-12. The cut lines 102-4L, 102-5L, and 102-6L are arrayed in this order from the left side to the right side. The cut lines 102-4R, 102-5R, and 102-6R are formed in the portion P8 which is the right part of the film 101-12. The cut lines 102-4R, 102-5R, and 102-6R are arrayed in this order from the right side to the left side. Thus, the interval between the paired cut lines 102 differs from pair to pair. Specifically, the interval between the cut line 102-4L and the cut line 102-4R that form the first pair is the largest. The interval between the cut line 102-5L and the cut line 102-5R that form the second pair is the second largest. The interval between the cut line 102-6L and the cut line 102-6R that form the third pair is the smallest.

As described above, in the face shield 1-12 according to the twelfth embodiment, a plurality of pairs of the cut lines 102 are formed similarly to the face shield 1-11 according to the eleventh embodiment. Therefore, by selecting a pair of the cut lines 102 to be used in accordance with the size of the face of the user or the mask, the gap between the face shield 1-12 and the mask 2 can be adjusted, and the face shield 1-12 can fit well to the face of the user. A user whose face is large, for example, can use the cut lines 102-4L and 102-4R that form the first pair to maintain the gap between the face shield 1-12 and the mask 2, and cause the face shield 1-12 to fit well to his/her face. Alternatively, a user whose face is small, for example, can use the cut lines 102-6L and 102-6R that form the third pair to maintain the gap between the face shield 1-12 and the mask 2, and cause the face shield 1-12 to fit well to his/her face.

Thirteenth Embodiment

A face shield 1-13 according to a thirteenth embodiment of the present invention will be described with reference to FIG. 23.

Figure 23:
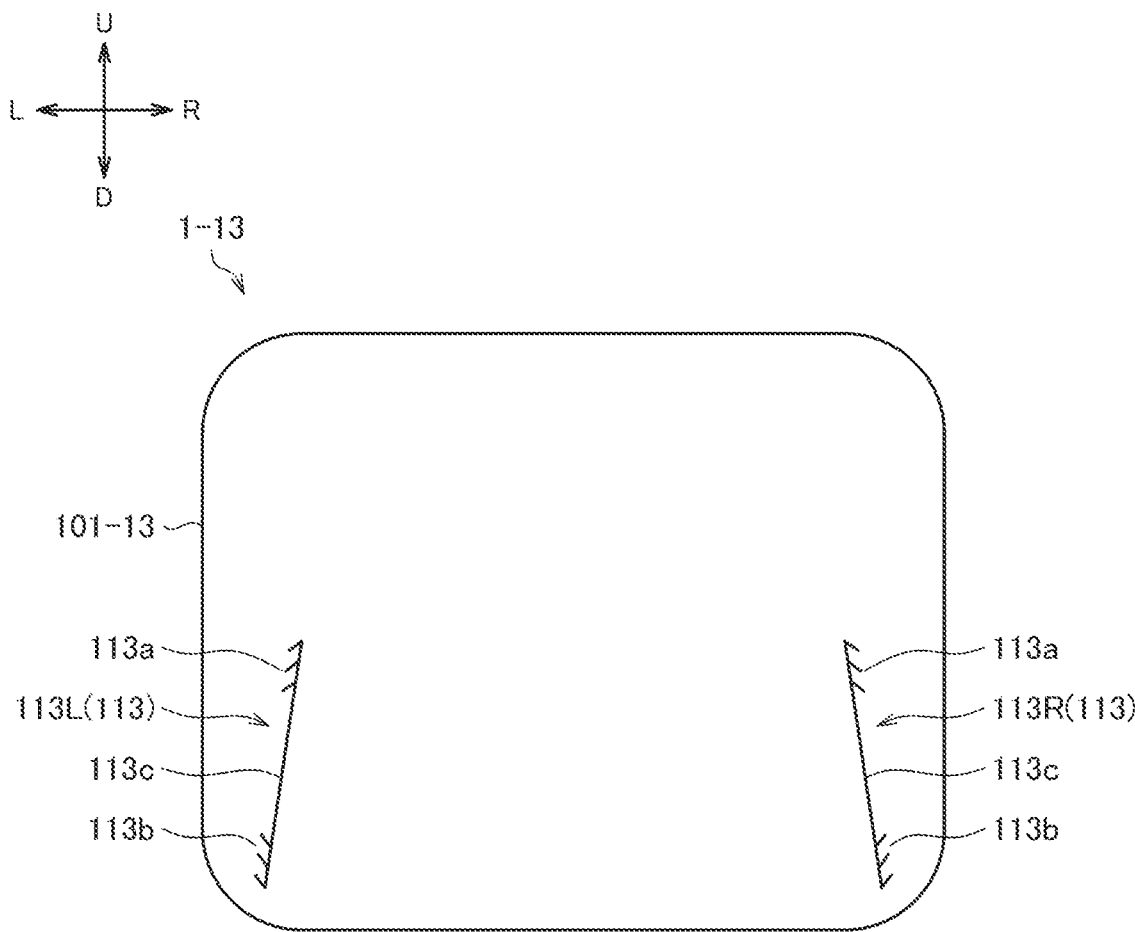
FIG. 23 is a plan view showing a face shield according to a thirteenth embodiment of the present invention.

FIG. 23 is a plan view showing the face shield 1-13.

The face shield 1-13 according to the thirteenth embodiment is different from the face shield 1-1 according to the first embodiment in terms of the shape of engagement parts 113*a* and 113*b* formed on cut lines 113.

As shown in FIG. 23, a pair of cut lines 113L and 113R through which the straps 202 of the mask 2 can be inserted are formed in both the left and right parts of the face shield 1-13 (specifically, a film 101-13 that forms the face shield 1-13). Note that in a case of not particularly distinguishing between the cut line 113L and the cut line 113R, they will simply be called the cut line 113 as well.

The cut line 113 is a closed-type cut line included in an inner side of the face shield 1-13 (that is, an inner side relative to an outer edge of the film 101-13) without intersecting with an outer edge of the face shield 1-13 (that is, the outer edge of the film 101-13). The cut line 113 is formed so as to extend in a direction that intersects with the left-right direction.

The cut line 113L is formed on the lower side of the left part of the film 101-13. The two straps 202-1 and 202-2 extending from the left side of the mask 2 are inserted through the cut line 113L. The cut line 113R is formed on the lower side of the right part of the film 101-13. The two straps 202-3 and 202-4 extending from the right side of the mask 2 are inserted through the cut line 113R.

The cut line 113 has the engagement parts 113*a* and 113*b* to be engaged with the straps 202 inserted through the cut line 113, and a linear part 113*c*. The engagement parts 113*a* and 113*b* are formed respectively at both ends of the cut line 113. In the present embodiment, the engagement parts 113*a* and 113*b* are portions (branched portions) in which the cut line 113 is branched. Note that although FIG. 23 shows an example in which the cut line 113 is branched at three places in the engagement parts 113*a* and 113*b*, the number of branched portions of the cut line 113 may be other than three. In addition, although FIG. 23 shows an example in which the cut line 113 is branched into two lines at each of the branched portions in the engagement parts 113*a* and 113*b*, the cut line 113 may be branched into three or more lines. In addition, although FIG. 23 shows an example in which the cut line 113 is branched in the engagement parts 113*a* and 113*b* to one side with respect to the linear part 113*c*, the cut line 113 may be branched to both sides.

The engagement part 113*a* is formed at the upper end of the cut line 113, and the engagement part 113*b* is formed at the lower end of the cut line 113. The linear part 113*c* is a portion between the engagement part 113*a* and the engagement part 113*b* on the cut line 113. The linear part 113*c* is a portion in which the cut line 113 is formed linearly. Note that in the cut line 113 according to the present embodiment, the engagement parts 113*a* and 113*b* at both the ends are coupled by the linear part 113*c* which is linear, however, the present invention is not limited to such an example. The coupling line that couples the engagement parts 113*a* and 113*b* may be, for example, a curved line which is gently curved or the like rather than being linear. The strap 202-1 is engaged with the engagement part 113*a* of the cut line 113L, and the strap 202-2 is engaged with the engagement part 113*b* of the cut line 113L. The strap 202-3 is engaged with the engagement part 113*a* of the cut line 113R, and the strap 202-4 is engaged with the engagement part 113*b* of the cut line 113R.

As described above, in the face shield 1-13 according to the thirteenth embodiment, the engagement parts 113*a* and 113*b* are portions in which the cut line 113 is branched. Thus, portions of the film 101-13 on both the sides of the engagement parts 113*a* and 113*b* have a complicated shape as compared with portions on both the sides of the linear part 113*c*. A large friction resistance is thereby produced between the straps 202 inserted through the cut line 113 and the engagement parts 113*a* and 113*b*, so that the straps 202 inserted through the cut line 113 are firmly caught. Displacement of the straps 202 in two directions, the direction in which the straps 202 are inserted through the cut line 113 and the direction along the cut line 113 can thereby be restricted by the engagement parts 113*a* and 113*b*.

Fourteenth Embodiment

A face shield 1-14 according to a fourteenth embodiment of the present invention will be described with reference to FIG. 24.

Figure 24:
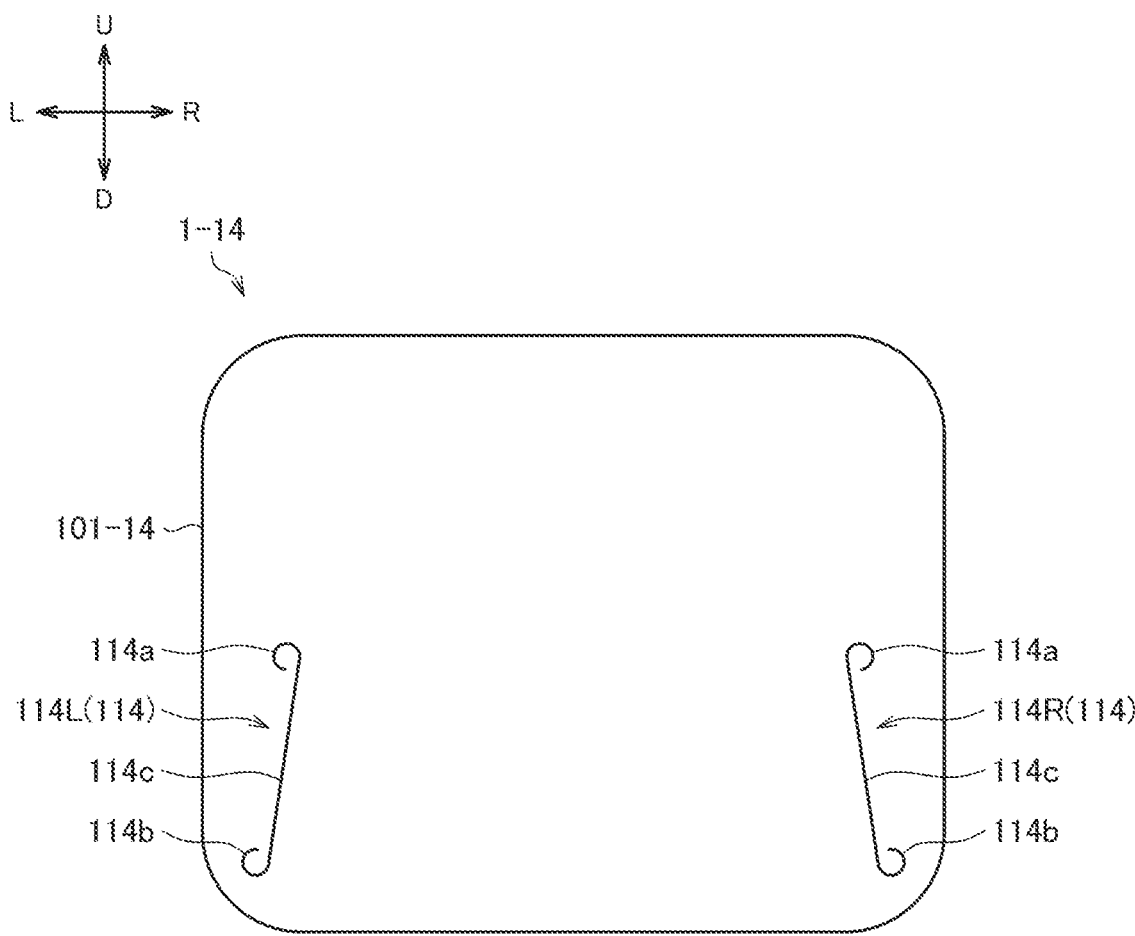
FIG. 24 is a plan view showing a face shield according to a fourteenth embodiment of the present invention.

FIG. 24 is a plan view showing the face shield 1-14.

The face shield 1-14 according to the fourteenth embodiment is different from the face shield 1-1 according to the first embodiment in terms of the shape of engagement parts 114*a* and 114*b* formed on cut lines 114.

As shown in FIG. 24, a pair of cut lines 114L and 114R through which the straps 202 of the mask 2 can be inserted are formed in both left and right parts of the face shield 1-14 (specifically, a film 101-14 that forms the face shield 1-14). Note that in a case of not particularly distinguishing between the cut line 114L and the cut line 114R, they will simply be called the cut line 114 as well.

The cut line 114 is a closed-type cut line included in an inner side of the face shield 1-14 (that is, an inner side relative to an outer edge of the film 101-14) without intersecting with an outer edge of the face shield 1-14 (that is, the outer edge of the film 101-14). The cut line 114 is formed so as to extend in a direction that intersects with the left-right direction.

The cut line 114L is formed on the lower side of the left part of the film 101-14. The two straps 202-1 and 202-2 extending from the left side of the mask 2 are inserted through the cut line 114L. The cut line 114R is formed on the lower side of the right part of the film 101-14. The two straps 202-3 and 202-4 extending from the right side of the mask 2 are inserted through the cut line 114R.

The cut line 114 has the engagement parts 114a and 114b to be engaged with the straps 202 inserted through the cut line 114, and a linear part 114c. The engagement parts 114a and 114b are formed respectively at both ends of the cut line 114. In the present embodiment, the engagement parts 114a and 114b are portions (curved portions) in which the cut line 114 is curved. Note that although FIG. 24 shows an example in which the engagement parts 114a and 114b have an arc shape, the shape of the engagement parts 114a and 114b is not limited to this example. For example, the engagement parts 114a and 114b may have an oval shape or may have a shape including a linear part as long as it is a shape at least partially curved.

The engagement part 114a is formed at the upper end of the cut line 114, and the engagement part 114b is formed at the lower end of the cut line 114. The linear part 114c is a portion between the engagement part 114a and the engagement part 114b on the cut line 114. The linear part 114c is a portion in which the cut line 114 is formed linearly. Note that in the cut line 114 according to the present embodiment, the engagement parts 114a and 114b at both the ends are coupled by the linear part 114c which is linear, however, the present invention is not limited to such an example. The coupling line that couples the engagement parts 114a and 114b may be, for example, a curved line which is gently curved or the like rather than being linear. The strap 202-1 is engaged with the engagement part 114a of the cut line 114L, and the strap 202-2 is engaged with the engagement part 114b of the cut line 114L. The strap 202-3 is engaged with the engagement part 114a of the cut line 114R, and the strap 202-4 is engaged with the engagement part 114b of the cut line 114R.

As described above, in the face shield 1-14 according to the fourteenth embodiment, the engagement parts 114a and 114b are portions in which the cut line 114 is curved. Thus, portions of the film 101-14 on both the sides of the engagement parts 114a and 114b have a complicated shape as compared with portions on both the sides of the linear part 114c. A large friction resistance is thereby produced between the straps 202 inserted through the cut line 114 and the engagement parts 114a and 114b, so that the straps 202 inserted through the cut line 114 are firmly caught. Displacement of the straps 202 in two directions, the direction in which the straps 202 are inserted through the cut line 114 and the direction along the cut line 114 can thereby be restricted by the engagement parts 114a and 114b.

Fifteenth Embodiment

A face shield 1-15 according to a fifteenth embodiment of the present invention will be described with reference to FIGS. 25 and 26.

Figure 25:
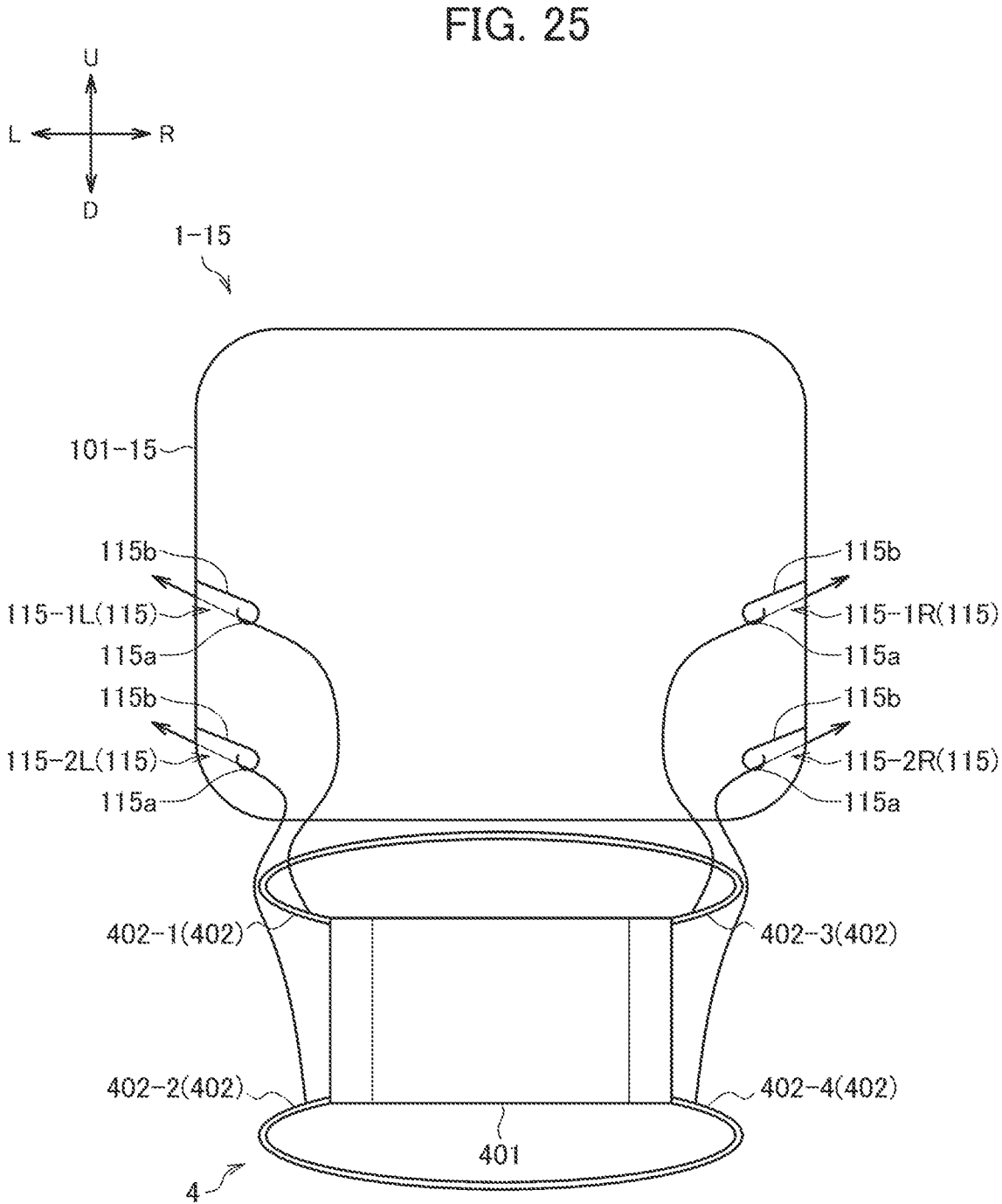
FIG. 25 is a plan view showing a face shield according to a fifteenth embodiment of the present invention.
Figure 26:
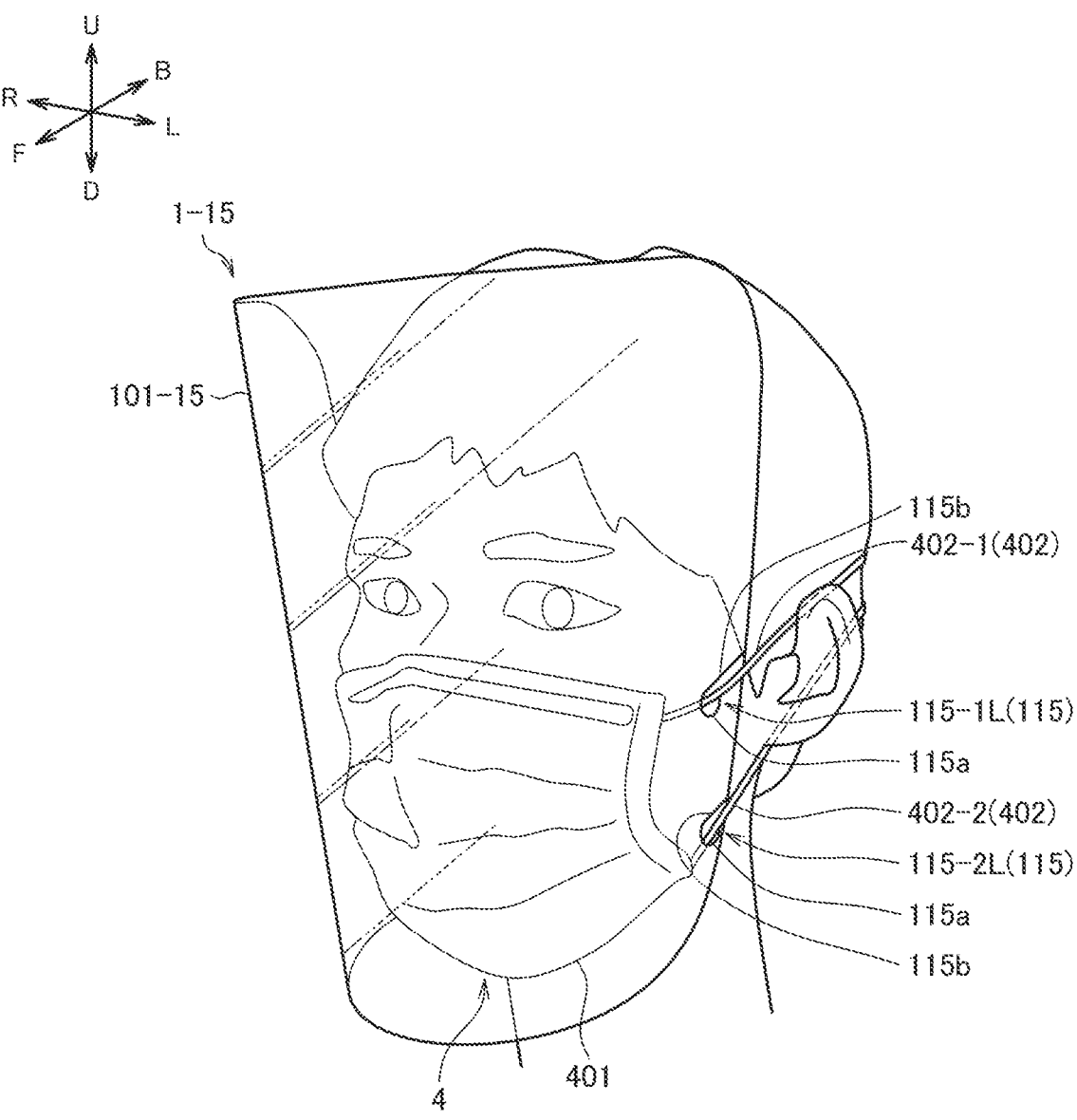
FIG. 26 is a perspective view showing a usage state of the face shield according to the fifteenth embodiment of the present invention.

FIG. 25 is a plan view showing the face shield 1-15. FIG. 26 is a perspective view showing a usage state of the face shield 1-15. FIGS. 25 and 26 show an example in which the face shield 1-15 is attached to a mask 4 of the overhead type. However, the face shield 1-15 can easily be combined and used with various masks similarly to the face shield 1-1. For example, the face shield 1-15 can also be attached/detached to/from the mask 2 of the ear-hung type described above.

As shown in FIG. 25, the mask 4 has a main body part 401 and straps 402.

The main body part 401 has a configuration similar to that of the main body part 201 of the mask 2 described above. A strap 402-1 extends from the upper side on the left side of the main body part 401, and a strap 402-2 extends from the lower side on the left side of the main body part 401. A strap 402-3 extends from the upper side on the right side of the main body part 401, and a strap 402-4 extends from the lower side on the right side of the main body part 401. The straps 402-1 and the strap 402-3 are connected to each other, and are wound around and worn on the head of a user. The strap 402-2 and the strap 402-4 are connected to each other, and are wound around and worn on a portion of the head of the user that is located below the position at which the strap 402-1 and the strap 402-3 are worn. In this manner, the mask 4 is what is called an overhead type mask.

The face shield 1-15 according to the fifteenth embodiment is different from the face shield 1-1 according to the first embodiment in that cut lines 115 through which the straps 402 of the mask 4 are to be inserted are open-type cut lines. This enables the face shield 1-15 to be attached/detached to/from the mask 4 of the overhead type besides the mask 2 of the ear-hung type and the mask 3 of the tie-string type.

As shown in FIG. 25, two pairs of the cut lines 115 (cut lines 115-1L, 115-1R and cut lines 115-2L, 115-2R) are formed in both left and right parts of the face shield 1-15 (specifically, a film 101-15 that forms the face shield 1-15). The straps 402 of the mask 4 can be inserted through the cut lines 115. The cut line 115-1L and the cut line 115-1R form the first pair. The cut line 115-2L and the cut line 115-2R form the second pair. The two pairs of the cut lines 115 (that is, the cut lines 115-1L, 115-1R and the cut lines 115-2L, 115-2R) are formed side by side in the up-down direction. Specifically, the cut lines 115-1L and 115-1R are arranged above the cut lines 115-2L and 115-2R. However, the number of pairs of the cut lines 115 should only be at least one, and a single pair or three or more pairs may be provided.

The cut line 115 is an open-type cut line having one end intersecting with an outer edge of the face shield 1-15 (that is, an outer edge of the film 101-15), and the other end arranged on an inner side of the face shield 1-15 (that is, an inner side relative to the outer edge of the film 101-15).

The cut line 115-1L and the cut line 115-2L are formed so as to intersect with the outer edge on the left side of the film 101-15 and incline downward in the right direction. The strap 402-1 extending from the left side of the mask 4 is inserted through the cut line 115-1L. The strap 402-2 extending from the left side of the mask 4 is inserted through the cut line 115-2L. The cut line 115-1R and the cut line 115-2R are formed so as to intersect with the outer edge on the right side of the film 101-15 and incline downward in the left direction. The strap 402-3 extending from the right side of the mask 4 is inserted through the cut line 115-1R. The strap 402-4 extending from the right side of the mask 4 is inserted through the cut line 115-2R.

The cut line 115 has an engagement part 115*a* to be engaged with the strap 402 inserted through the cut line 115, and a linear part 115*b*. The engagement part 115*a* is formed at the other end of the cut line 115 (that is, an end arranged on the inner side of the face shield 1-15). In the present embodiment, the engagement part 115*a* is a portion in which the cut line 115 is curved similarly to the engagement parts 114*a* and 114*b* of the cut line 114 of the fourteenth embodiment. However, the shape of the engagement part 115*a* is not limited to this example. For example, the engagement part 115*a* may be a portion in which the cut line 115 is formed into a sawtooth shape as in the first embodiment, or may be a portion in which the cut line 115 is branched as in the thirteenth embodiment. The linear part 115*b* is a portion between the engagement part 115*a* of the cut line 115 and the outer edge of the film 101-15. The linear part 115*b* is a portion in which the cut line 115 is formed linearly. Note that in the cut line 115 according to the present embodiment, the engagement part 115*a* and the outer edge of the film 101-15 are coupled by the linear part 115*b* which is linear, however, the present invention is not limited to such an example. The coupling line that couples the engagement part 115*a* and the outer edge of the film 101-15 may be, for example, a curved line which is gently curved or the like rather than being linear. In addition, the coupling line may be formed into a complicated shape such as a sawtooth shape, for example, in order to prevent the straps 402 from coming off.

Two straps 402-1 and 402-2 extending from the left side of the mask 4 are respectively engaged with the two engagement parts 115*a* formed in the cut lines 115-1L and 115-2L which are two open-type cut lines formed on the left side of the face shield 1-15. The strap 402-1 is engaged with the engagement part 115*a* of the cut line 115-1L, and the strap 402-2 is engaged with the engagement part 115*a* of the cut line 115-2L. Two straps 402-3 and 402-4 extending from the right side of the mask 4 are respectively engaged with the two engagement parts 115*a* formed in the cut lines 115-1R and 115-2R which are two open-type cut lines formed on the right side of the face shield 1-15. The strap 402-3 is engaged with the engagement part 115*a* of the cut line 115-1R, and the strap 402-4 is engaged with the engagement part 115*a* of the cut line 115-2R. Particularly from the perspective of stably holding and fixing the face shield 1-15, portions of the straps 402 located as close to the main body part 401 as possible preferably are engaged with the engagement parts 115*a*.

The strap 402 inserted through the cut line 115 is caught by portions of the film 101-15 on both the sides of the engagement part 115*a*. Displacement of the strap 402 in two directions, the direction in which the strap 402 is inserted through the cut line 115 and the direction along the cut line 115 is thereby restricted by the engagement part 115*a*. Thus, the face shield 1-15 can easily be attached/detached to/from the mask 4, and the face shield 1-15 can stably be held by and fixed to the mask 4 when in use.

In particular, in the face shield 1-15 according to the fifteenth embodiment, the two straps 402 extending from one side in the left-right direction of the mask 4 are respectively inserted through the two open-type cut lines formed on one side in the left-right direction of the face shield 1-15. Then, the two straps 402 are respectively engaged with the two engagement parts 115*a* formed at the other end of the cut lines 115 which are two open-type cut lines. The face shield 1-15 is thereby supported by a total of the four straps 402 at four points. Thus, the face shield 1-15 can be held and fixed more stably when in use.

Sixteenth Embodiment

A face shield 1-16 according to a sixteenth embodiment of the present invention will be described with reference to FIGS. 27 to 29.

Figure 27:
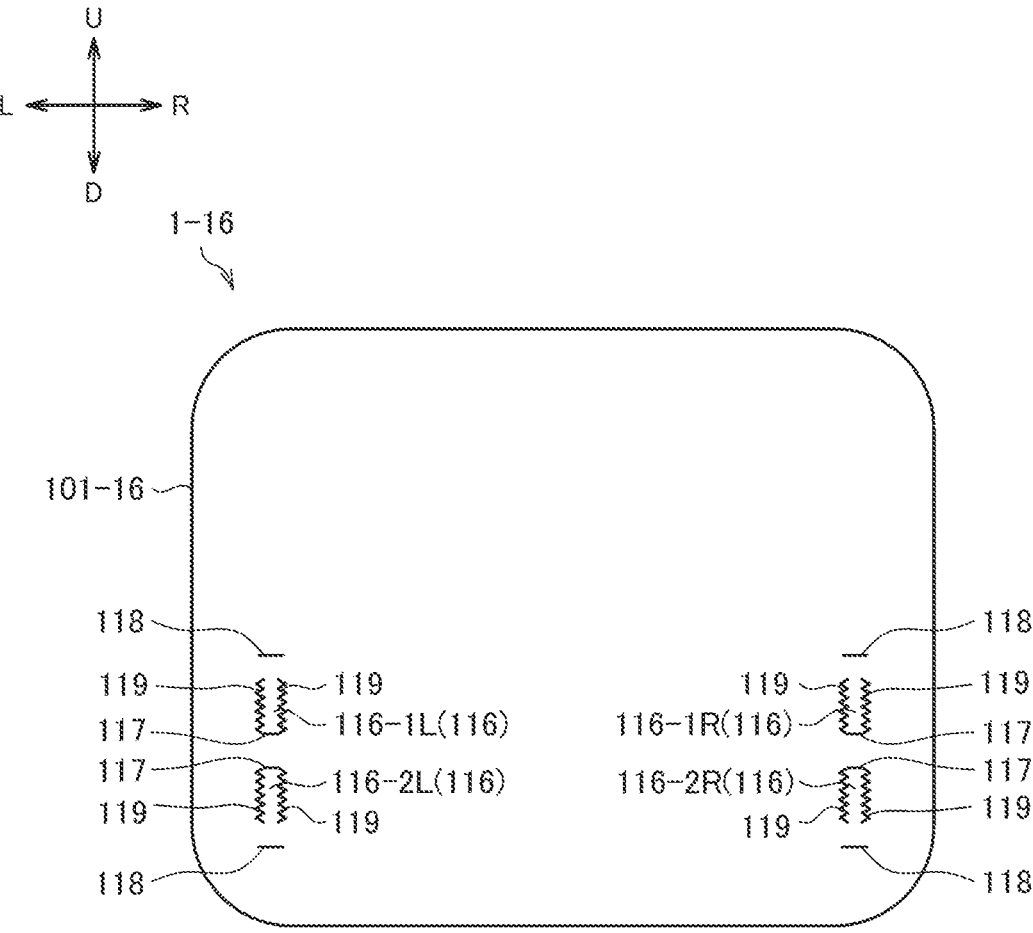
FIG. 27 is a plan view showing a face shield according to a sixteenth embodiment of the present invention.

FIG. 27 is a plan view showing the face shield 1-16. FIG. 28 is a schematic view showing states before and after a changeable part 116 which will be described later is deformed. Specifically, FIG. 28 is a drawing of the face shield 1-16 as seen from behind (that is, as seen from the user side). FIG. 29 is a cross-sectional view showing the state after the changeable part 116 which will be described later is deformed. Specifically, FIG. 29 is a cross-sectional view showing a cross section orthogonal to a surface of the face shield 1-16.

The face shield 1-16 according to the sixteenth embodiment can also be attached/detached to/from the mask 4 of the overhead type besides the mask 2 of the ear-hung type or the mask 3 of the tie-string type similarly to the face shield 1-15 according to the fifteenth embodiment. Hereinafter, an example in which the face shield 1-16 is attached to the mask 4 of the overhead type will be described as an example.

The face shield 1-16 according to the sixteenth embodiment is different from the face shield 1-15 according to the fifteenth embodiment in terms of a mechanism through which the straps 402 of the mask 4 are inserted and a mechanism in which the face shield 1-16 and the straps 402 are engaged with each other.

As shown in FIG. 27, two pairs of the changeable parts 116 (changeable parts 116-1L, 116-1R and changeable parts 116-2L, 116-2R) are formed in both left and right parts of the face shield 1-16 (specifically, a film 101-16 that forms the face shield 1-16). The changeable parts 116 are part of the film 101-16. In other words, the changeable parts 116 are portions of the film 101-16 that can be deformed by partially cutting out part of the film 101-16 along cut lines 117 formed in the face shield 1-16.

The changeable part 116-1L and the changeable part 116-1R form the first pair. The changeable part 116-2L and the changeable part 116-2R form the second pair. The two pairs of the changeable parts 116 (that is, the changeable parts 116-1L, 116-1R and the changeable parts 116-2L, 116-2R) are formed side by side in the up-down direction. Specifically, the changeable parts 116-1L and 116-1R are arranged above the changeable parts 116-2L and 116-2R. However, there should only be at least one pair of the changeable parts 116, and a single pair or three or more pairs may be provided.

The cut lines 117 have a U-shape. Both ends of the cut lines 117 that form the changeable parts 116-1L and 116-1R are arranged on the upper side, and the cut lines 117 are formed so as to extend downward from both the ends. Thus, the respective changeable parts 116 of the changeable parts 116-1L and 116-1R are foldable using the upper ends of the respective changeable parts 116 as fulcrum points. Both ends of the cut lines 117 that form the changeable parts 116-2L and 116-2R are arranged on the lower side, and the cut lines 117 are formed so as to extend upward from both the ends. Thus, the respective changeable parts 116 of the changeable parts 116-2L and 116-2R are foldable using the lower ends of the respective changeable parts 116 as fulcrum points. However, the shape of the cut lines 117 is not limited to this example, and may be an arc shape, for example.

Insertion parts 118 in which the changeable parts 116 can be inserted are formed in the face shield 1-16 at positions adjacent to the changeable parts 116. The insertion parts 118 are formed of cut lines (specifically, closed-type cut lines formed so as to extend in the left-right direction). The insertion parts 118 in which the changeable parts 116-1L and 116-1R can be inserted are formed above the respective changeable parts 116. The insertion parts 118 in which the changeable parts 116-2L and 116-2R can be inserted are formed below the respective changeable parts 116.

Figure 28:
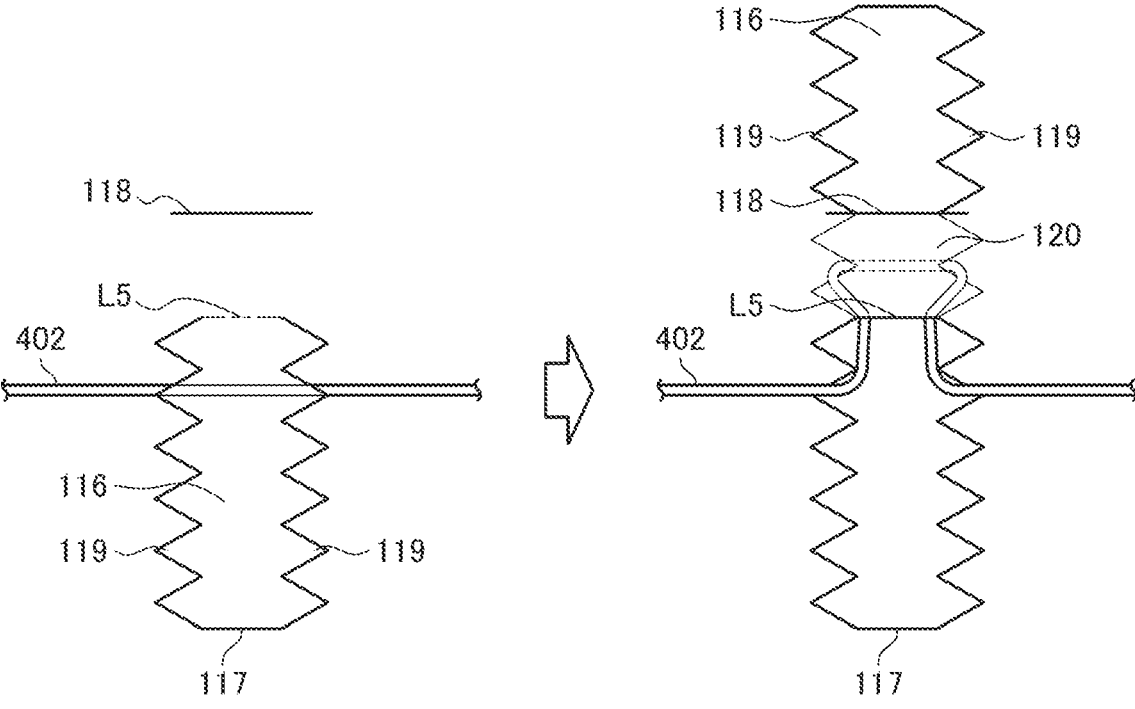
FIG. 28 is a schematic view showing states before and after a changeable part according to the sixteenth embodiment of the present invention is deformed.
Figure 29:
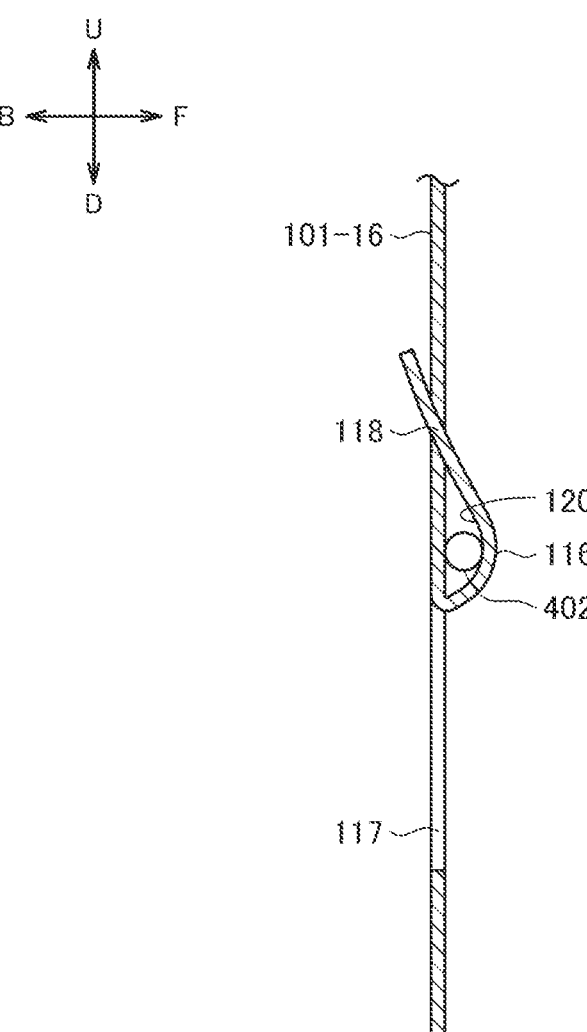
FIG. 29 is a cross-sectional view showing the state after the changeable part is deformed according to the sixteenth embodiment of the present invention.

As shown in FIG. 28, the changeable part 116 is deformed such that a leading end of the changeable part 116 is inserted in the insertion part 118. Before the changeable part 116 is deformed, the strap 402 of the mask 4 is set in a state being caught in the front-back direction by the changeable part 116 and portions of the film 101-16 on both the sides of the changeable part 116. In this state, specifically, the strap 402 of the mask 4 passes behind the portions of the film 101-16 on both the sides of the changeable part 116, and passes in front of the changeable part 116. The changeable part 116 is folded from this state together with the strap 402, and is inserted in the insertion part 118. At this time, the changeable part 116 is folded along a folding line L5 arranged at a base end of the changeable part 116.

Herein, locking claws 119 for locking the changeable part 116 in the insertion part 118 are formed on both the left and right sides of the changeable part 116. In the example shown in FIG. 28, a plurality of the locking claws 119 are formed respectively on both the left and right sides of the changeable part 116 by formation of both the left and right sides of the changeable part 116 into a sawtooth shape. The changeable part 116 is locked in the insertion part 118 with the locking claws 119 in a state in which the changeable part 116 is inserted in the insertion part 118. After the changeable part 116 is deformed, a looped part 120 through which the strap 402 of the mask 4 can be inserted is formed by the changeable part 116 having been deformed and the film 101-16, as shown in FIGS. 28 and 29. The looped part 120 is engaged with the strap 402 inserted through the looped part 120. The looped part 120 should only be a closed-type annular portion that forms an inner space through which the strap 402 can be inserted, and the shape of the looped part 120 is not particularly limited. For example, the looped part 120 may have a circular shape, an oval shape, or a shape including a linear part.

Specifically, the strap 402-1 extending from the left side of the mask 4 is inserted through the looped part 120 formed by the changeable part 116-1L, and is engaged with the looped part 120. The strap 402-2 extending from the left side of the mask 4 is inserted through the looped part 120 formed by the changeable part 116-2L, and is engaged with the looped part 120. The strap 402-3 extending from the right side of the mask 4 is inserted through the looped part 120 formed by the changeable part 116-1R, and is engaged with the looped part 120. The strap 402-4 extending from the right side of the mask 4 is inserted through the looped part 120 formed by the changeable part 116-2R, and is engaged with the looped part 120. Particularly from the perspective of stably holding and fixing the face shield 1-16, a portion of the strap 402 located as close to the main body part 401 as possible preferably is engaged with the looped part 120.

As described above, in the face shield 1-16 according to the sixteenth embodiment, the looped part 120 through which the strap 402 of the mask 4 can be inserted is formed by deformation of the changeable part 116. Specifically, the looped part 120 is formed by insertion of the changeable part 116 in the insertion part 118. In particular, the looped part 120 is stably formed by locking of the changeable part 116 in the insertion part 118 with the locking claws 119. The looped part 120 is then engaged with the strap 402 inserted through the looped part 120. Displacement of the strap 402 in the direction in which the strap 402 is inserted through the looped part 120 is thereby restricted. Thus, the face shield 1-16 can easily be attached/detached to/from the mask 4, and the face shield 1-16 can stably be held by and fixed to the mask 4 when in use.

In particular, in the face shield 1-16 according to the sixteenth embodiment, the looped parts 120 formed by the two changeable parts 116 formed on one side in the left-right direction of the face shield 1-16 are respectively engaged with the two straps 402 extending from one side in the left-right direction of the mask 4. The face shield 1-16 is thereby supported by a total of the four straps 402 at four points. Thus, the face shield 1-16 can be held and fixed more stably when in use.

Seventeenth Embodiment

A face shield 1-17 according to a seventeenth embodiment of the present invention will be described with reference to FIGS. 30 to 32.

Figure 30:
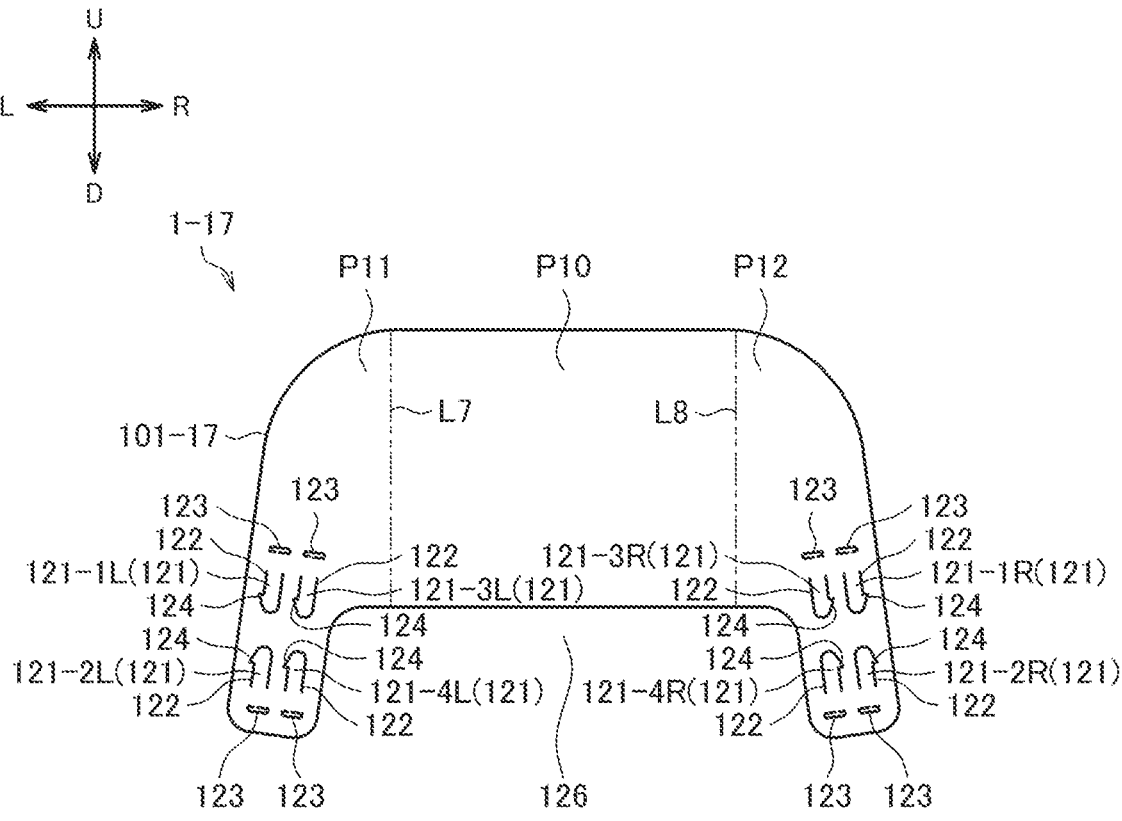
FIG. 30 is a plan view showing a face shield according to a seventeenth embodiment of the present invention.

FIG. 30 is a plan view showing the face shield 1-17. FIG. 31 is a schematic view showing states before and after a changeable part 121 which will be described later is deformed. Specifically, FIG. 31 is a drawing of the face shield 1-17 as seen from behind (that is, as seen from the user side). FIG. 32 is a perspective view showing a usage state of the face shield 1-17. FIG. 32 shows an example in which the face shield 1-17 is attached to the mask 4 of the overhead type. However, the face shield 1-17 can also be attached/detached to/from the mask 2 of the ear-hung type or the mask 3 of the tie-string type besides the mask 4 of the overhead type similarly to the face shields 1-15 and 1-16.

The face shield 1-17 according to the seventeenth embodiment is different from the face shield 1-16 according to the sixteenth embodiment in terms of a configuration of the changeable parts 121.

As shown in FIG. 30, four pairs of the changeable parts 121 (changeable parts 121-1L, 121-1R, changeable parts 121-2L, 121-2R, changeable parts 121-3L, 121-3R, and changeable parts 121-4L, 121-4R) are formed in both the left and right parts of the face shield 1-17 (specifically, a film 101-17 that forms the face shield 1-17). The changeable parts 121 are portions that can be deformed by being partially cut out along cut lines 122 formed in the face shield 1-17.

The changeable part 121-1L and the changeable part 121-1R form the first pair. The changeable part 121-2L and the changeable part 121-2R form the second pair. The changeable part 121-3L and the changeable part 121-3R form the third pair. The changeable part 121-4L and the changeable part 121-4R form the fourth pair. The changeable parts 121-1L and 121-1R (the first pair) are arranged above the changeable parts 121-2L and 121-2R (the second pair). The changeable parts 121-3L and 121-3R (the third pair) are arranged above the changeable parts 121-4L and 121-4R (the fourth pair). The changeable parts 121-1L and 121-1R (the first pair) are arranged on the outer side of the face shield 1-17 with respect to the changeable parts 121-3L and 121-3R (the third pair). The changeable parts 121-2L and 121-2R (the second pair) are arranged on the outer side of the face shield 1-17 with respect to the changeable parts 121-4L and 121-4R (the fourth pair). However, the number of pairs of the changeable parts 121 should only be at least one, and may be other than four.

The cut lines 122 have a U-shape. Both ends of the cut lines 122 that form the changeable parts 121-1L and 121-1R (the first pair) and the changeable parts 121-3L and 121-3R (the third pair) are arranged on the upper side, and the cut lines 122 are formed so as to extend downward from both the ends. Thus, the respective changeable parts 121 of the changeable parts 121-1L and 121-1R (the first pair) and the changeable parts 121-3L and 121-3R (the third pair) are foldable using the upper ends of the respective changeable parts 121 as fulcrum points. Both ends of the cut lines 122 that form the changeable parts 121-2L and 121-2R (the second pair) and the changeable parts 121-4L and 121-4R (the fourth pair) are arranged on the lower side, and the cut lines 122 are formed so as to extend upward from both the ends. Thus, the respective changeable parts 121 of the changeable parts 121-2L and 121-2R (the second pair) and the changeable parts 121-4L and 121-4R (the fourth pair) are foldable using the lower ends of the respective changeable parts 121 as fulcrum points. However, the shape of the cut lines 122 is not limited to this example, and may be an arc shape, for example.

Insertion parts 123 in which the changeable parts 121 can be inserted are formed in the face shield 1-17 at positions adjacent to the changeable parts 121. The insertion parts 123 are formed of cut lines (specifically, U-shaped closed-type cut lines). However, the insertion parts 123 may be closed-type cut lines formed so as to extend in the left-right direction as in the sixteenth embodiment. Specifically, the insertion parts 123 in which the changeable parts 121-1L and 121-1R (the first pair) and the changeable parts 121-3L and 121-3R (the third pair) can be inserted are formed above the respective changeable parts 121. The insertion parts 123 in which the changeable parts 121-2L and 121-2R (the second pair) and the changeable parts 121-4L and 121-4R (the fourth pair) can be inserted are formed below the respective changeable parts 121.

Figure 31:
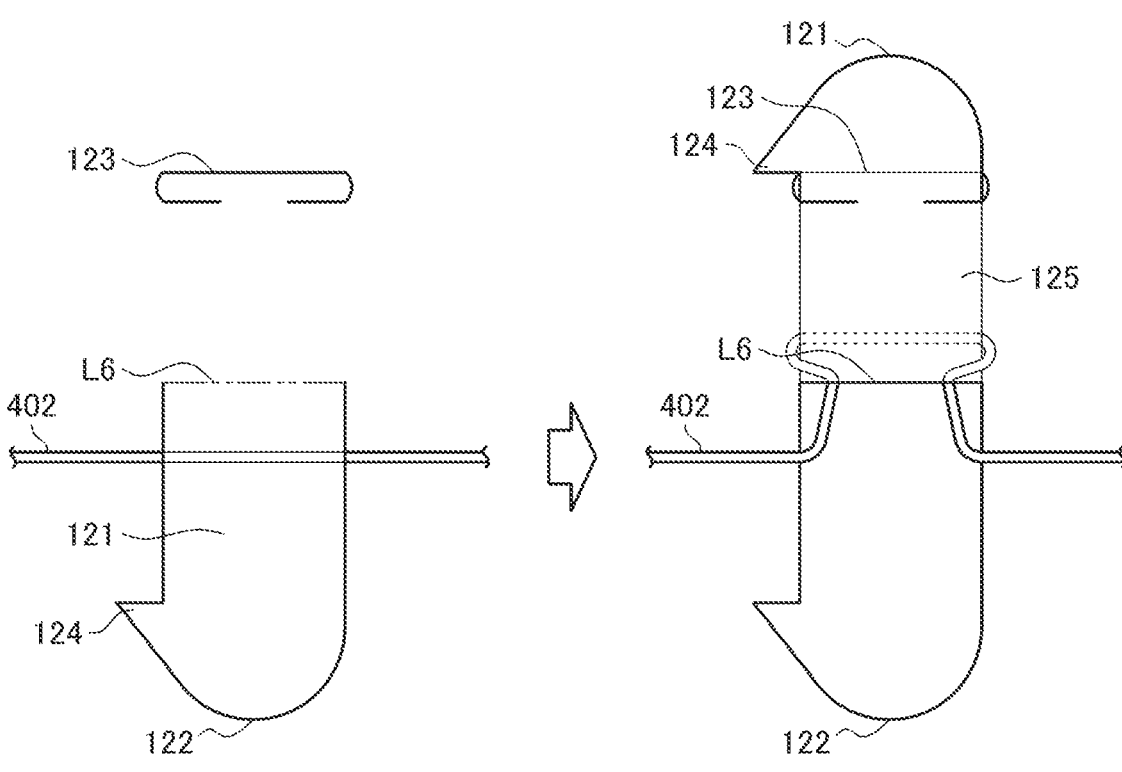
FIG. 31 is a schematic view showing states before and after a changeable part according to the seventeenth embodiment of the present invention is deformed.

As shown in FIG. 31, the changeable part 121 is deformed such that a leading end of the changeable part 121 is inserted in the insertion part 123. Before the changeable part 121 is deformed, the strap 402 of the mask 4 is set in a state being caught in the front-back direction by the changeable part 121 and portions of the film 101-17 on both the sides of the changeable part 121. In this state, specifically, the strap 402 of the mask 4 passes behind the portions of the changeable part 121 on both the sides of the film 101-17, and passes in front of the changeable part 121. The changeable part 121 is folded from this state together with the strap 402, and is inserted in the insertion part 123. At this time, the changeable part 121 is folded along a folding line L6 arranged at a base end of the changeable part 121.

Herein, a locking claw 124 for locking the changeable part 121 in the insertion part 123 is formed on a side of the changeable part 121. The locking claw 124 is a hook-shaped portion protruding from the side of the changeable part 121 toward the outside. The changeable part 121 is locked in the insertion part 123 with the locking claw 124 in a state in which the changeable part 121 is inserted in the insertion part 123. After the changeable part 121 is deformed, a looped part 125 through which the strap 402 of the mask 4 can be inserted is formed by the changeable part 121 having been deformed and the film 101-17 similarly to the sixteenth embodiment. The looped part 125 is engaged with the strap 402 inserted through the looped part 125. Note that the shape of the looped part 125 is not particularly limited similarly to the looped parts 120 according to the sixteenth embodiment.

Specifically, the strap 402-1 extending from the left side of the mask 4 is inserted through the looped part 125 formed by the changeable part 121-1L or the changeable part 121-3L, and is engaged with the looped part 125. The strap 402-2 extending from the left side of the mask 4 is inserted through the looped part 125 formed by the changeable part 121-2L or the changeable part 121-4L, and is engaged with the looped part 125. The strap 402-3 extending from the right side of the mask 4 is inserted through the looped part 125 formed by the changeable part 121-1R or the changeable part 121-3R, and is engaged with the looped part 125. The strap 402-4 extending from the right side of the mask 4 is inserted through the looped part 125 formed by the changeable part 121-2R or the changeable part 121-4R, and is engaged with the looped part 125. Particularly from the perspective of stably holding and fixing the face shield 1-17, a portion of the strap 402 located as close to the main body part 401 as possible preferably is engaged with the looped part 125.

As described above, in the face shield 1-17 according to the seventeenth embodiment, the looped part 125 is formed by deformation of the changeable part 121 similarly to the sixteenth embodiment. Specifically, the looped part 125 is formed by insertion of the changeable part 121 in the insertion part 123. The looped part 125 is stably formed particularly by locking of the changeable part 121 in the insertion part 123 with the locking claw 124. Then, movement of the strap 402 in the direction in which the strap 402 is inserted through the looped part 125 is restricted by engagement of the strap 402 with the looped part 125. Thus, the face shield 1-17 can easily be attached/detached to/from the mask 4, and the face shield 1-17 can stably be held by and fixed to the mask 4 when in use.

Herein, the interval from the changeable part 121-1L and the changeable part 121-2L to the changeable part 121-1R and the changeable part 121-2R is wider than the interval from the changeable part 121-3L and the changeable part 121-4L to the changeable part 121-3R and the changeable part 121-4R. Thus, by selecting a pair of the changeable parts 121 to be used in accordance with the size of the face of a user or the mask, the gap between the face shield 1-17 and the mask 4 can be maintained, and the face shield 1-17 can fit well to the face of the user.

A user whose face is large, for example, can use the changeable part 121-1L and the changeable part 121-2L as well as the changeable part 121-1R and the changeable part 121-2R to maintain the gap between the face shield 1-17 and the mask 4, and the face shield 1-17 can fit well to his/her face. In this case, the strap 402-1 extending from the left side of the mask 4 is inserted through the looped part 125 formed by the changeable part 121-1L, and the strap 402-2 extending from the left side of the mask 4 is inserted through the looped part 125 formed by the changeable part 121-2L. In addition, the strap 402-3 extending from the right side of the mask 4 is inserted through the looped part 125 formed by the changeable part 121-1R, and the strap 402-4 extending from the right side of the mask 4 is inserted through the looped part 125 formed by the changeable part 121-2R.

Alternatively, a user whose face is small, for example, can use the changeable part 121-3L and the changeable part 121-4L as well as the changeable part 121-3R and the changeable part 121-4R to maintain the gap between the face shield 1-17 and the mask 4, and the face shield 1-17 can fit well to his/her face. In this case, the strap 402-1 extending from the left side of the mask 4 is inserted through the looped part 125 formed by the changeable part 121-3L, and the strap 402-2 extending from the left side of the mask 4 is inserted through the looped part 125 formed by the changeable part 121-4L. In addition, the strap 402-3 extending from the right side of the mask 4 is inserted through the looped part 125 formed by the changeable part 121-3R, and the strap 402-4 extending from the right side of the mask 4 is inserted through the looped part 125 formed by the changeable part 121-4R.

Further, in the face shield 1-17 according to the seventeenth embodiment, a notch 126 is formed in the face shield 1-17 at a position to be opposed to the respiratory organs of the user similarly to the face shield 1-2 according to the second embodiment.

Figure 32:
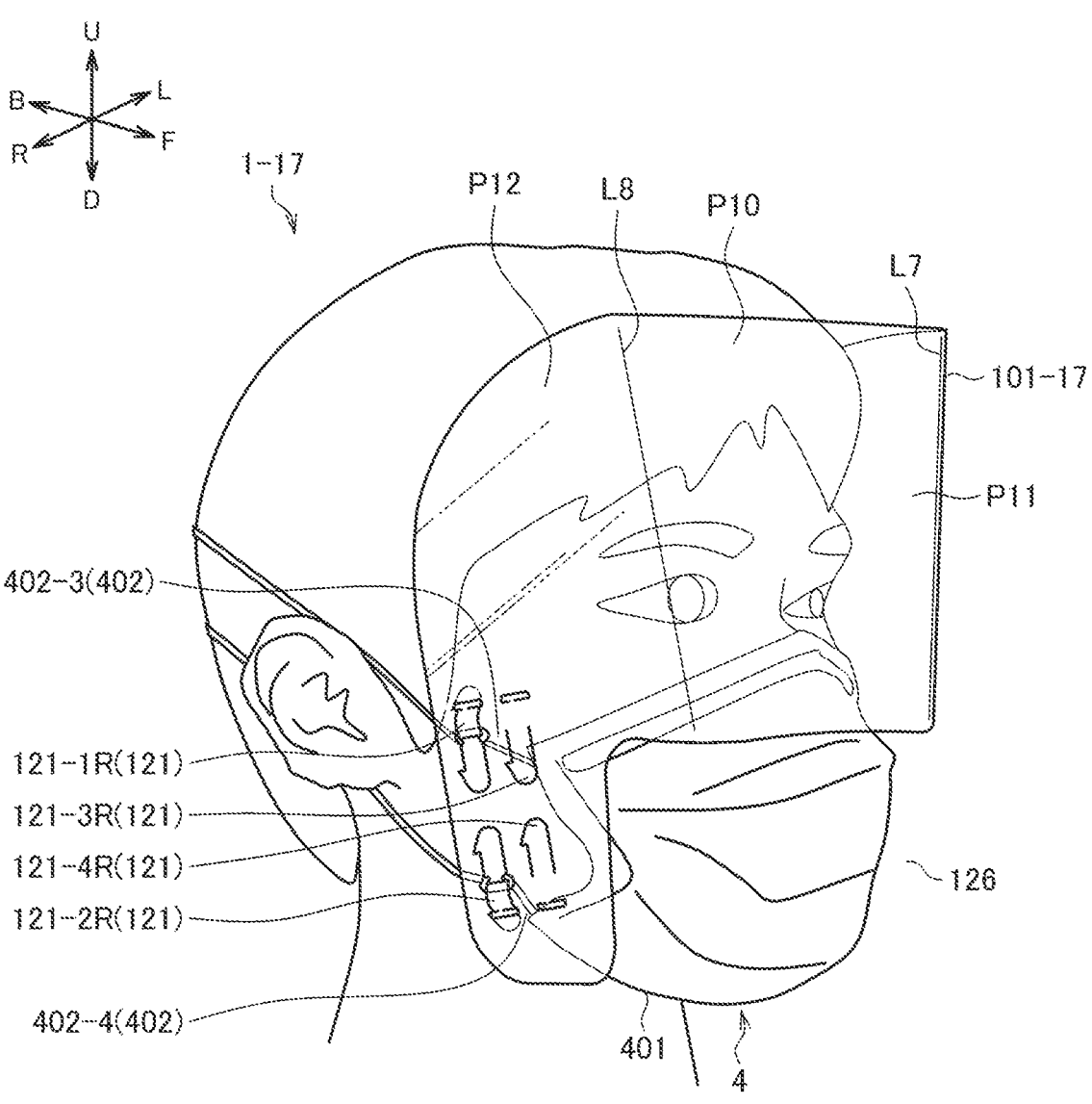
FIG. 32 is a perspective view showing a usage state of the face shield according to the seventeenth embodiment of the present invention.

As shown in FIG. 32, the notch 126 is formed at the position to be opposed to the respiratory organs (for example, the mouth and the nose) of the user when in use. Thus, air exhaled from the respiratory organs of the user passes through or bypasses the mask 4, and is then discharged to the outside of the face shield 1-17 through the notch 126. This can effectively prevent the face shield 1-17 from fogging up because of exhaled air of the user, and enables the field of view to be kept well.

Further, in the face shield 1-17 according to the seventeenth embodiment, folding lines L7 and L8 are arranged between a portion P10 of the face shield 1-17 to be located on the front side of the face of the user and portions P11, P12 to be located on lateral sides of the face of the user similarly to the face shield 1-6 according to the sixth embodiment.

Note that as shown in FIG. 30, a left part of the face shield 1-17 in which the changeable parts 121-1L, 121-2L, 121-3L, and 121-4L are formed is the portion P11 (hereinafter referred to as "the left lateral portion P11") to be located on the left lateral side of the face of the user. A right part of the face shield 1-17 in which the changeable parts 121-1R, 121-2R, 121-3R, and 121-4R are formed is the portion P12 (hereinafter referred to as "the right lateral portion P12") to be located on the right lateral side of the face of the user. The portion P10 (hereinafter referred to as "the front portion P10") is a portion between the portion P11 and the portion P12 on the face shield 1-17. The left lateral portion P11 is foldable along the folding line L7 with respect to the front portion P10. The right lateral portion P12 is foldable along the folding line L8 with respect to the front portion P10. The folding lines L7 and L8 may be perforated so as to facilitate folding of the left lateral portion P11 and the right lateral portion P12.

When the face shield 1-17 is used, the left lateral portion P11 and the right lateral portion P12 are in a state folded along the folding lines L7 and L8 toward the face of the user as shown in FIG. 32. Thus, the portion P10 on the front side of the face shield 1-17 is opposed to the face of the user in a state maintaining a planar shape. In the case in which the front portion P10 of the face shield 1-17 has a planar shape, reflection of external light can thereby be reduced as compared with a case in which the front portion P10 has a curved shape, which enables the field of view to be kept well.

Eighteenth Embodiment

A face shield 1-18 according to an eighteenth embodiment of the present invention will be described with reference to FIGS. 33 and 34.

Figure 33:
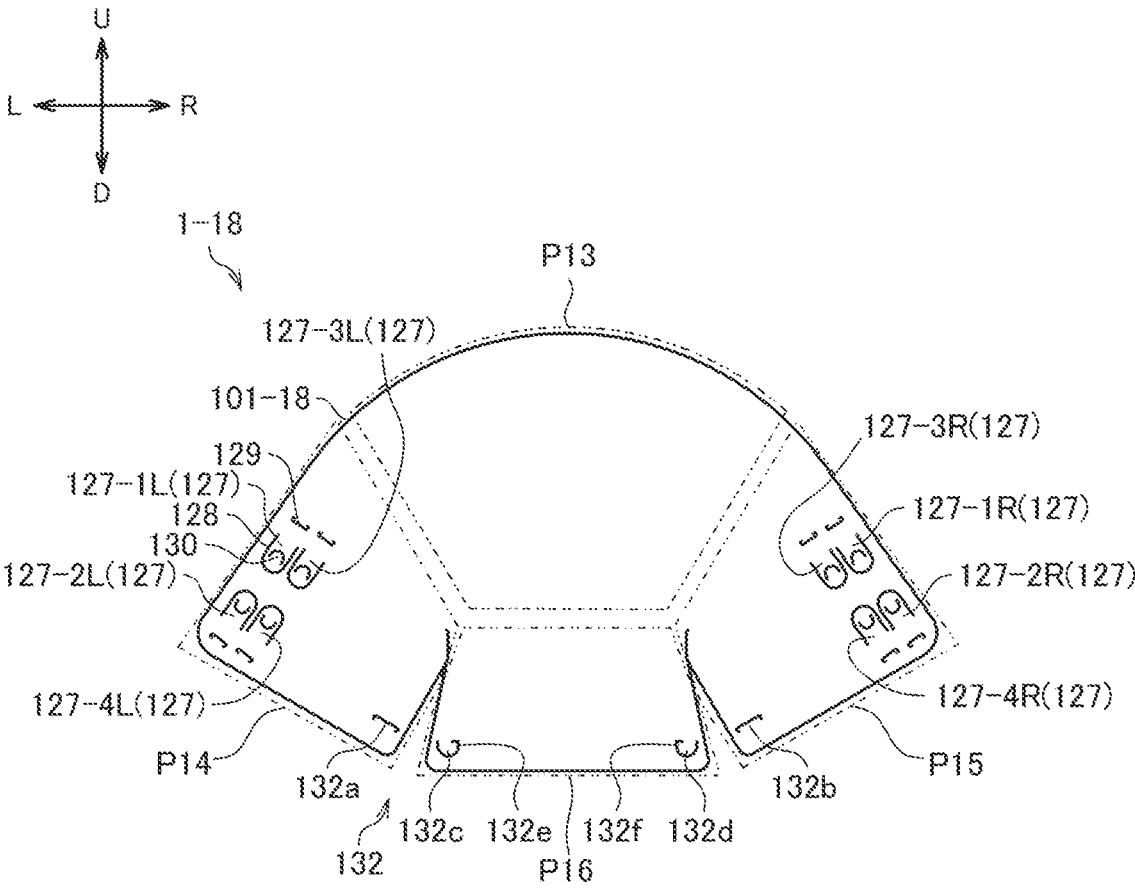
FIG. 33 is a plan view showing a face shield according to an eighteenth embodiment of the present invention.

FIG. 33 is a plan view showing the face shield 1-18. FIG. 34 is a schematic view showing states before and after a changeable part 127 which will be described later is deformed. Specifically, FIG. 34 is a drawing of the face shield 1-18 as seen from behind (that is, as seen from the user side).

The face shield 1-18 according to the eighteenth embodiment can also be attached/detached to/from the mask 4 of the overhead type besides the mask 2 of the ear-hung type or the mask 3 of the tie-string type similarly to the face shield 1-15 according to the fifteenth embodiment, the face shield 1-16 according to the sixteenth embodiment, and the face shield 1-17 according to the seventeenth embodiment. Hereinafter, an example in which the face shield 1-18 is attached to the mask 4 of the overhead type will be described as an example.

The face shield 1-18 according to the eighteenth embodiment is different from the face shield 1-16 according to the sixteenth embodiment and the face shield 1-17 according to the seventeenth embodiment in terms of a configuration of the changeable part 127.

As shown in FIG. 33, four pairs of the changeable parts 127 (changeable parts 127-1L, 127-1R, changeable parts 127-2L, 127-2R, changeable parts 127-3L, 127-3R, and changeable parts 127-4L, 127-4R) are formed in both left and right parts of the face shield 1-18 (specifically, a film 101-18 that forms the face shield 1-18). The changeable parts 127 are portions that can be deformed by being partially cut out along cut lines 128 formed in the face shield 1-18.

The changeable part 127-1L and the changeable part 127-1R form the first pair. The changeable part 127-2L and the changeable part 127-2R form the second pair. The changeable part 127-3L and the changeable part 127-3R form the third pair. The changeable part 127-4L and the changeable part 127-4R form the fourth pair. The changeable parts 127-1L and 127-1R (the first pair) are arranged above the changeable parts 127-2L and 127-2R (the second pair). The changeable parts 127-3L and 127-3R (the third pair) are arranged above the changeable parts 127-4L and 127-4R (the fourth pair). The changeable parts 127-1L and 127-1R (the first pair) are arranged on the outer side of the face shield 1-18 with respect to the changeable parts 127-3L and 127-3R (the third pair). The changeable parts 127-2L and 127-2R (the second pair) are arranged on the outer side of the face shield 1-18 with respect to the changeable parts 127-4L and 127-4R (the fourth pair). However, the number of pairs of the changeable parts 127 should only be at least one, and may be other than four.

The cut lines 128 have a U-shape. Both ends of the cut lines 128 that form the changeable parts 127-1L and 127-1R (the first pair) and the changeable parts 127-3L and 127-3R (the third pair) are arranged on the upper side, and the cut lines 128 are formed so as to extend downward from both the ends. Thus, the respective changeable parts 127 of the changeable parts 127-1L and 127-1R (the first pair) and the changeable parts 127-3L and 127-3R (the third pair) are foldable using the upper ends of the respective changeable parts 127 as fulcrum points. Both ends of the cut lines 128 that form the changeable parts 127-2L and 127-2R (the second pair) and the changeable parts 127-4L and 127-4R (the fourth pair) are arranged on the lower side, and the cut line 128 are formed so as to extend upward from both the ends. Thus, the respective changeable parts 127 of the changeable parts 127-2L and 127-2R (the second pair) and the changeable parts 127-4L and 127-4R (the fourth pair) are foldable using the lower ends of the respective changeable parts 127 as fulcrum points. However, the shape of the cut lines 128 is not limited to this example, and may be an arc shape, for example.

Insertion parts 129 in which the changeable parts 127 can be inserted are formed in the face shield 1-18 at positions adjacent to the changeable parts 127. The insertion parts 129 are formed of cut lines (specifically, U-shaped closed-type cut lines). However, the insertion parts 129 may be closed-type cut lines formed so as to extend in the left-right direction as in the sixteenth embodiment. Specifically, the insertion parts 129 in which the changeable parts 127-1L and 127-1R (the first pair) and the changeable parts 127-3L and 127-3R (the third pair) can be inserted are formed above the respective changeable parts 127. The insertion parts 129 in which the changeable parts 127-2L and 127-2R (the second pair) and the changeable parts 127-4L and 127-4R (the fourth pair) can be inserted are formed below the respective changeable parts 127.

Herein, a locking claw 130 for locking the changeable part 127 in the insertion part 129 is formed on a leading end side of the changeable part 127. The locking claw 130 is a portion partially cut out along an arc-shaped closed-type cut line which is curved toward a base end of the changeable part 127. However, the above-described closed-type cut line should only be formed so as to protrude toward the base end side of the changeable part 127, and may have a polygonal shape, or may have a shape including a linear part and a curve-shaped portion, for example.

Figure 34:
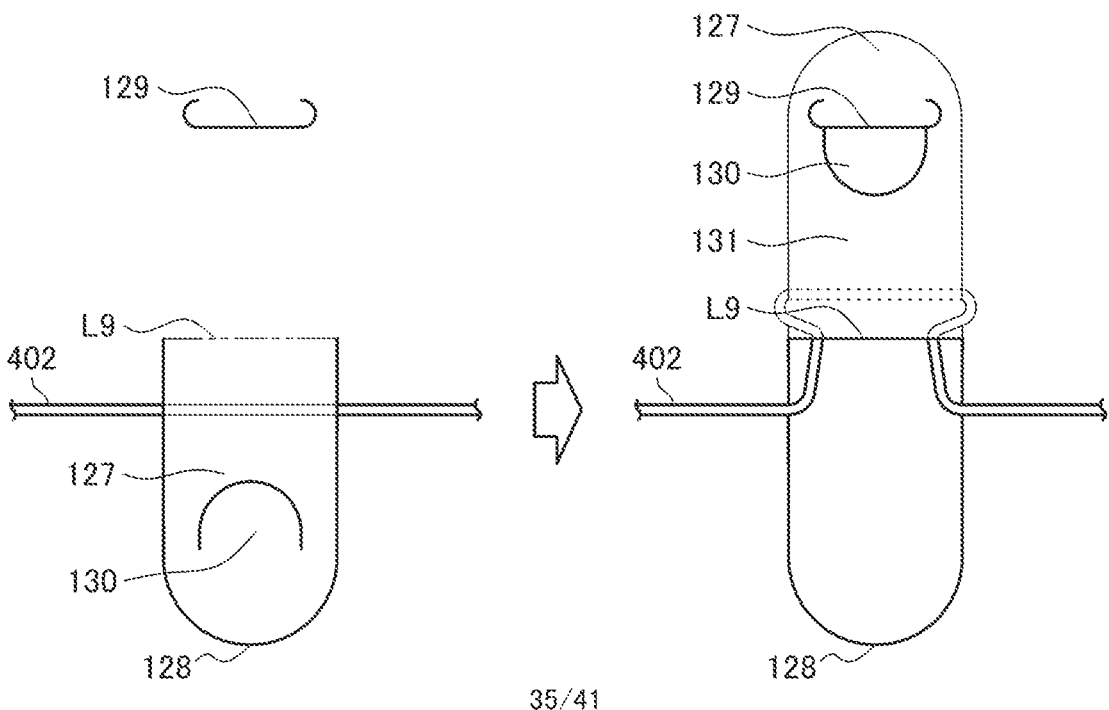
FIG. 34 is a schematic view showing states before and after a changeable part according to the eighteenth embodiment of the present invention is deformed.

As shown in FIG. 34, the changeable part 127 is deformed such that leading end of the changeable part 127 is inserted in the insertion part 129. Before the changeable part 127 is deformed, the strap 402 of the mask 4 is set in a state being caught in the front-back direction by the changeable part 127 and portions of the film 101-18 on both sides of the changeable part 127. In this state, specifically, the strap 402 of the mask 4 passes behind the portions of the film 101-18 on both the sides of the changeable part 127, and passes in front of the changeable part 127. The changeable part 127 is folded from this state together with the strap 402. At this time, the changeable part 127 is folded along a folding line L9 arranged at the base end of the changeable part 127.

The changeable part 127 is locked in the insertion part 129 with the locking claw 130 in a state in which the changeable part 127 is folded and inserted in the insertion part 129. After the changeable part 127 is deformed, a looped part 131 through which the strap 402 of the mask 4 can be inserted is formed by the changeable part 127 having been deformed and the film 101-18 similarly to the sixteenth embodiment and the seventeenth embodiment. The looped part 131 is engaged with the strap 402 inserted through the looped part 131. Note that the shape of the looped part 131 is not particularly limited similarly to the looped part 120 according to the sixteenth embodiment and the looped part 125 according to the seventeenth embodiment.

Specifically, the strap 402-1 extending from the left side of the mask 4 is inserted through the looped part 131 formed by the changeable part 127-1L or the changeable part 127-3L, and is engaged with the looped part 131. The strap 402-2 extending from the left side of the mask 4 is inserted through the looped part 131 formed by the changeable part 127-2L or the changeable part 127-4L, and is engaged with the looped part 131. The strap 402-3 extending from the right side of the mask 4 is inserted through the looped part 131 formed by the changeable part 127-1R or the changeable part 127-3R, and is engaged with the looped part 131. The strap 402-4 extending from the right side of the mask 4 is inserted through the looped part 131 formed by the changeable part 127-2R or the changeable part 127-4R, and is engaged with the looped part 131. Particularly from the perspective of stably holding and fixing the face shield 1-18, a portion of the strap 402 located as close to the main body part 401 as possible preferably is engaged with the looped part 131.

As described above, in the face shield 1-18 according to the eighteenth embodiment, the looped part 131 is formed by deformation of the changeable part 127 similarly to the sixteenth embodiment and the seventeenth embodiment. Specifically, the looped part 131 is formed by insertion of the changeable part 127 in the insertion part 129. The looped part 131 is stably formed particularly by locking of the changeable part 127 in the insertion part 129 with the locking claw 130. Then, movement of the strap 402 in the direction in which the strap 402 is inserted through the looped part 131 is restricted by engagement of the strap 402 with the looped part 131. Thus, the face shield 1-18 can easily be attached/detached to/from the mask 4, and the face shield 1-18 can stably be held by and fixed to the mask 4 when in use.

Herein, the interval from the changeable part 127-1L and the changeable part 127-2L to the changeable part 127-1R and the changeable part 127-2R is wider than the interval from the changeable part 127-3L and the changeable part 127-4L to the changeable part 127-3R and the changeable part 127-4R Thus, by selecting a pair of the changeable parts 127 to be used in accordance with the size of the face of a user or the mask similarly to the seventeenth embodiment, the gap between the face shield 1-18 and the mask 4 can be maintained, and the face shield 1-18 can fit well to the face of the user.

A user whose face is large, for example, can use the changeable part 127-1L, the changeable part 127-2L, the changeable part 127-1R, and the changeable part 127-2R to maintain the gap between the face shield 1-18 and the mask 4, and the face shield 1-18 can fit well to his/her face. Alternatively, a user whose face is small, for example, can use the changeable part 127-3L, the changeable part 127-4L, the changeable part 127-3R, and the changeable part 127-4R to maintain the gap between the face shield 1-18 and the mask 4, and the face shield 1-18 can fit well to his/her face.

Further, the face shield 1-18 according to the eighteenth embodiment has a formative structure 132 that can be formed into a shape that tapers with distance from the face of a user similarly to the face shield 1-10 according to the tenth embodiment.

As shown in FIG. 33, the face shield 1-18 (specifically, a film 101-18 that forms the face shield 1-18) has a portion P13 to be located on the front side of the face of the user and opposed to the eyes, a portion P14 to be located on the left lateral side of the face of the user, a portion P15 to be located on the right lateral side of the face of the user, and a portion P16 to be located on the front side of the face of the user and opposed to the respiratory organs.

In the plan view shown in FIG. 33, the portion P14 (that is, a left part of the face shield 1-18) is formed so as to extend from the portion P13 (that is, an upper part of the face shield 1-18) in a lower left direction similarly to the face shield 1-10 according to the tenth embodiment. The portion P15 (that is, a right part of the face shield 1-18) is formed so as to extend from the portion P13 in a lower right direction. The portion P16 (that is, a lower part of the face shield 1-18) is formed between the portion P14 and the portion P15 so as to extend downward from the portion P13. The portion P16 is spaced from each of the portion P14 and the portion P15 in the left-right direction.

The formative structure 132 includes a cut line 132*a* formed in the portion P14, a cut line 132*b* formed in the portion P15, protruding parts 132*c*, 132*d* formed in the portion P16, and locking parts 132*e* and 132*f* respectively formed in the protruding parts 132*c* and 132*d*.

The cut lines 132a and 132b are closed-type cut lines. The cut line 132a is formed on the lower right side of the portion P14, and extends along an outer edge on the lower left side of the portion P14. The cut line 132b is formed on the lower left side of the portion P15, and extends along an outer edge on the lower right side of the portion P15. The protruding part 132c is formed on the lower left side of the portion P16, and protrudes in the down direction. The protruding part 132d is formed on the lower right side of the portion P16, and protrudes in the down direction. The protruding parts 132c and 132d are portions partially cut out along arc-shaped closed-type cut lines which are curved in the down direction. However, the above-described closed-type cut lines should only be formed so as to protrude in the down direction, and may have a polygonal shape, or may have a shape including a linear part and a curve-shaped portion, for example. The locking part 132e and 132f are hook-shaped portions formed on the sides of the protruding parts 132c and 132d.

In a case of forming the face shield 1-18 using the formative structure 132, the protruding part 132c in the portion P16 is inserted through the cut line 132a in the portion P14. At this time, the protruding part 132c is locked in the cut line 132a with the locking part 132e formed on the protruding part 132c. In addition, the protruding part 132d in the portion P16 is inserted through the cut line 132b in the portion P15. At this time, the protruding part 132d is locked in the cut line 132b with the locking part 132f formed on the protruding part 132d. In this manner, the face shield 1-18 is formed into a three-dimensional spatial shape (for example, the shape shown in FIG. 20) that tapers with distance from the face of the user similarly to the face shield 1-10 according to the tenth embodiment. Thus, the face shield 1-18 according to the eighteenth embodiment enables effects similar to those of the face shield 1-10 according to the tenth embodiment to be obtained.

Nineteenth Embodiment

A face shield 1-19 according to a nineteenth embodiment of the present invention will be described with reference to FIGS. 35 to 37.

Figure 35:
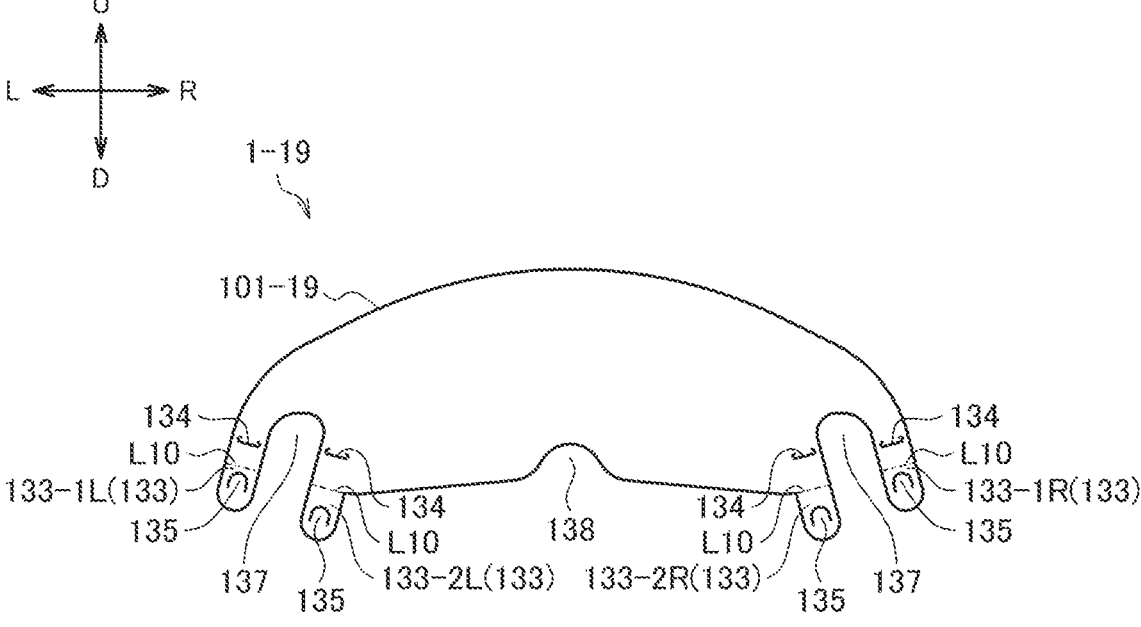
FIG. 35 is a plan view showing a face shield according to a nineteenth embodiment of the present invention.

FIG. 35 is a plan view showing the face shield 1-19. FIG. 36 is a schematic view showing states before and after changeable parts 133 (specifically, changeable parts 133-1L and 133-2L) which will be described later are deformed. Specifically, FIG. 36 is a drawing of the face shield 1-19 as seen from behind (that is, as seen from the user side). FIG. 37 is a perspective view showing a usage state of the face shield 1-19. FIG. 37 shows an example in which the face shield 1-19 is attached to the mask 2 of the ear-hung type. However, the face shield 1-19 can also be attached/detached to/from the mask 3 of the tie-string type or the mask 4 of the overhead type besides the mask 2 of the ear-hung type similarly to the face shields 1-15, 1-16, 1-17, and 1-18.

The face shield 1-19 according to the nineteenth embodiment is different from the face shield 1-16 according to the sixteenth embodiment, the face shield 1-17 according to the seventeenth embodiment, and the face shield 1-18 according to the eighteenth embodiment in that looped parts 136 (see FIG. 36) formed by the changeable parts 133 are not engaged with the strap 202 of the mask 2. In other words, when the strap 202 is inserted through the looped parts 136, the looped parts 136 are relatively movable with respect to the strap 202 in the direction in which the strap 202 is inserted.

In addition, the face shields 1-16, 1-17, and 1-18 according to the sixteenth, seventeenth, and eighteenth embodiments and the like described above are attached to both the upper straps 202-1, 202-3 and the lower straps 202-2, 202-4 of the mask 2. In contrast, the face shield 1-19 according to the nineteenth embodiment is attached only to the upper straps 202-1 and 202-3 of the mask 2, and is not attached to the lower straps 202-2 and 202-4.

As shown in FIG. 35, two pairs of the changeable parts 133 (the changeable parts 133-1L, 133-1R and the changeable parts 133-2L, 133-2R) are formed in both left and right parts of the face shield 1-19 (specifically, a film 101-19 that forms the face shield 1-19). The changeable parts 133 are portions of the face shield 1-19 that can be deformed. Specifically, the changeable parts 133 are portions in which the film 101-19 can easily be folded.

The changeable part 133-1L and the changeable part 133-1R form the first pair. The changeable part 133-2L and the changeable part 133-2R form the second pair. The changeable parts 133-1L and 133-1R (the first pair) are arranged on the outer side of the face shield 1-19 with respect to the changeable parts 133-2L and 133-2R (the second pair). The changeable part 133-1L and the changeable part 133-2L are formed away from each other in the left-right direction on the left side of the face shield 1-19. The changeable part 133-1R and the changeable part 133-2R are formed away from each other in the left-right direction on the right side of the face shield 1-19. In this manner, the two changeable parts 133 are formed away from each other in the left-right direction on one side in the left-right direction of the face shield 1-19.

However, if two or more looped parts 136 which will be described later can be formed on one side in the left-right direction of the face shield 1-19, the number of the changeable parts 133 formed on one side in the left-right direction of the face shield 1-19 should only be at least one, and may be three or more. In addition, the number of the changeable parts 133 formed on the left side of the face shield 1-19 and the number of the changeable parts 133 formed on the right side of the face shield 1-19 may be different from each other.

The changeable parts 133 are formed so as to extend downward from both the left and right parts of the face shield 1-19. Outer edges of the changeable parts 133 have a shape protruding downward (for example, a U-shape). However, the shape of the outer edges of the changeable parts 133 is not limited to this example, and may be an arc shape, an oval shape, any curved shape, a rectangular protruding shape, or the like, for example. Each of the changeable parts 133 is foldable upward along a folding line L10 arranged at a base end of each of the changeable parts 133.

Insertion parts 134 in which the changeable parts 133 can be inserted are formed in the face shield 1-19 at positions adjacent to the changeable parts 133. The insertion parts 134 are formed of cut lines (specifically, U-shaped closed-type cut lines). However, the insertion parts 134 may be closed-type cut lines formed so as to extend in the left-right direction as in the sixteenth embodiment. Specifically, the insertion parts 134 are formed above the respective changeable parts 133.

Herein, a locking claw 135 for locking the changeable part 133 in the insertion part 134 is formed on the leading end side of the changeable part 133. The locking claw 135 is a portion partially cut out along an arc-shaped closed-type cut line which is curved to be convex toward the base end side of the changeable part 133. However, the above-described closed-type cut line should only be formed so as to protrude toward the base end side of the changeable part 133, and may have a polygonal shape, or may have a shape including a linear part and a curve-shaped portion, for example.

Figure 36:
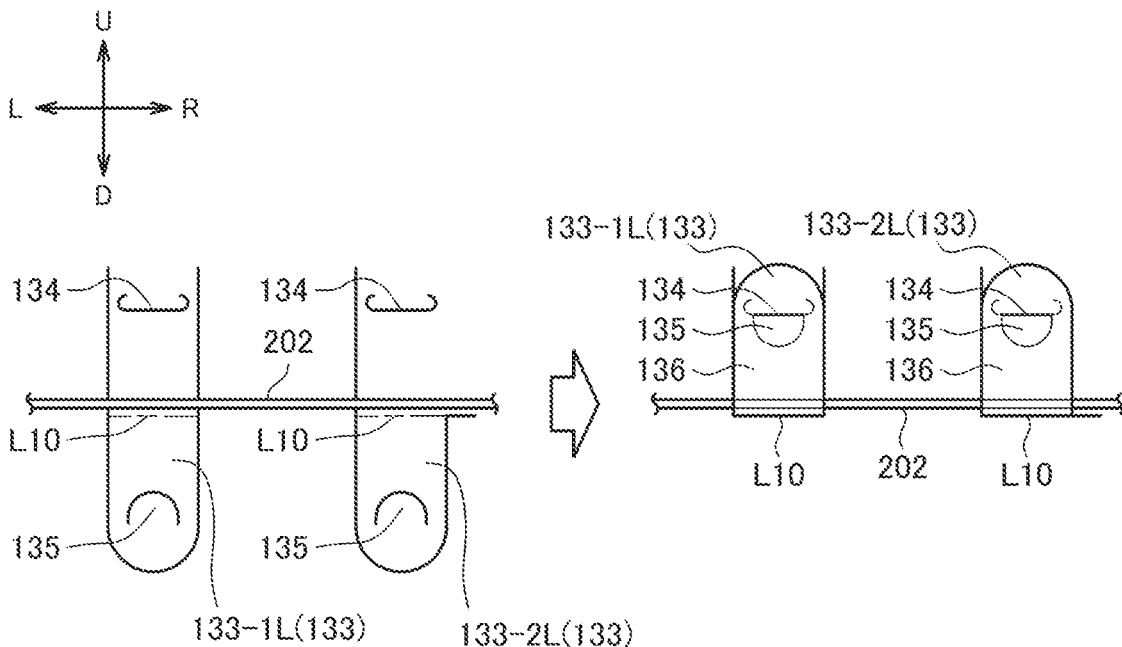
FIG. 36 is a schematic view showing states before and after a changeable part according to the nineteenth embodiment of the present invention is deformed.
Figure 37:
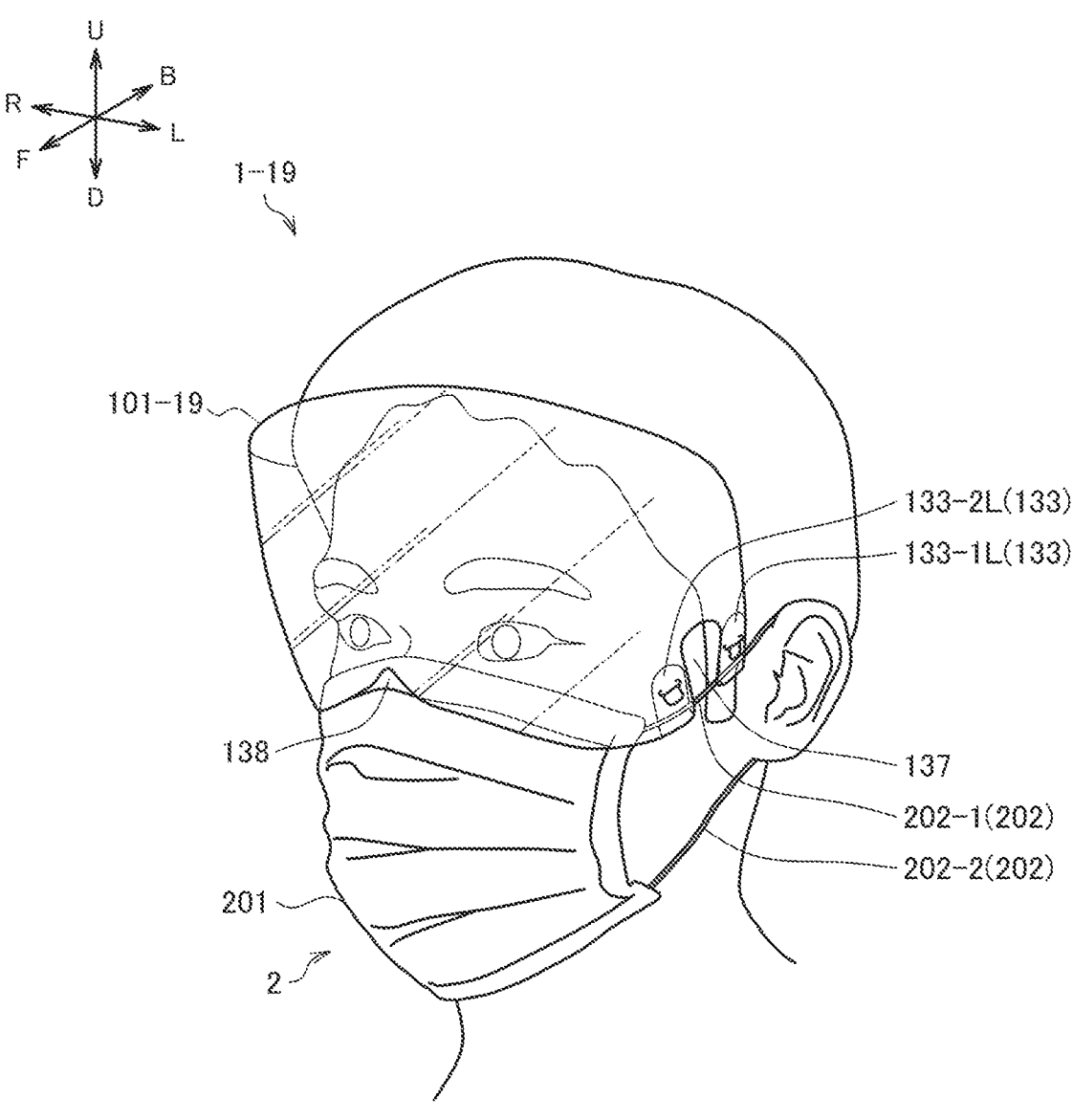
FIG. 37 is a perspective view showing a usage state of the face shield according to the nineteenth embodiment of the present invention.

As shown in FIG. 36, the changeable parts 133 are deformed such that leading ends of the changeable parts 133 are inserted in the insertion parts 134. Before the changeable parts 133 are deformed, the strap 202 of the mask 2 is set in a state passing behind the two changeable parts 133 (for example, the changeable parts 133-1L and 133-2L) on one side in the left-right direction of the face shield 1-19. The two changeable parts 133 are folded from this state along the folding line L10 so as to catch the strap 202.

The changeable parts 133 are locked in the insertion parts 134 with the locking claws 135 in a state in which the changeable parts 133 are folded and inserted in the insertion parts 134. After the changeable parts 133 are deformed, the looped parts 136 through which the strap 202 of the mask 2 can be inserted are formed by the changeable parts 133 having been deformed and the film 101-19 similarly to the sixteenth embodiment to the eighteenth embodiment. In the nineteenth embodiment, the two looped parts 136 are formed away from each other in the left-right direction by deformation of the two changeable parts 133 on one side in the left-right direction of the face shield 1-19.

Note that the shape of the looped parts 136 is not particularly limited similarly to the sixteenth embodiment to the eighteenth embodiment. In addition, in a case in which the number of the changeable parts 133 formed on one side in the left-right direction of the face shield 1-19 is three or more, the number of the looped parts 136 formed on the one side in the left-right direction of the face shield 1-19 is three or more. In addition, the number of the looped parts 136 formed on the left side of the face shield 1-19 and the number of the looped parts 136 formed on the right side of the face shield 1-19 may be different from each other.

Of the upper and lower two straps 202 on one side in the left-right direction of the mask 2, the upper strap 202 of the mask 2 (specifically, the strap 202-1 or the strap 202-3) is inserted through the two looped parts 136. Specifically, the upper strap 202-1 of the straps 202 extending from the left side of the mask 2 is inserted through the two looped parts 136 formed by the changeable part 133-1L and the changeable part 133-2L (that is, the two looped parts 136 formed on the left side of the face shield 1-19). The upper strap 202-3 of the straps 202 extending from the right side of the mask 2 is inserted through the two looped parts 136 (that is, the two looped parts 136 formed on the right side of the face shield 1-19) formed by the changeable part 133-1R and the changeable part 133-2R. The face shield 1-19 is thereby attached to the mask 2 as shown in FIG. 37. The face shield 1-19 mainly covers the eyes and a region around the eyes on the face of a user. Note that in the example shown in FIG. 37, not only the eyes of the user but also the whole area of the forehead are covered by the face shield 1-19. However, a width of the face shield 1-19 in the up-down direction may be narrower than the width in this example, so that only the eyes of the user and a lower part of the forehead are covered by the face shield 1-19.

As described above, in the face shield 1-19 according to the nineteenth embodiment, the looped parts 136 are formed by deformation of the changeable parts 133. Specifically, the looped parts 136 are formed by insertion of the changeable parts 133 in the insertion parts 134. The looped parts 136 are stably formed particularly by locking of the changeable parts 133 in the insertion parts 134 with the locking claws 135. Then, the upper straps 202 of the mask 2 are inserted through the looped parts 136. Since the face shield 1-19 is thereby supported only by the upper two straps 202 of the mask 2, the need to form the looped parts 136 through which the lower two straps 202 of the mask 2 are to be inserted is eliminated unlike the case of being supported by a total of the four straps 202 (for example, the sixteenth embodiment to the eighteenth embodiment described above). Since portions provided in the face shield 1-19 for forming the looped parts 136 through which the lower two straps 202 of the mask 2 are to be inserted can thus be omitted, the film 101-19 can be reduced in area. Various effects (such as weight reduction, for example) associated with the reduction in area of the film 101-19 can thereby be exerted as will be described later in detail.

In addition, in the face shield 1-19 according to the nineteenth embodiment, the looped parts 136 are not engaged with the straps 202. Thus, when the straps 202 are inserted through the looped parts 136, the looped parts 136 are relatively movable with respect to the straps 202 in the direction in which the straps 202 are inserted. Since this facilitates adjustment of the positional relationship between the face shield 1-19 and the mask 2 as compared with the case in which the looped parts 136 are engaged with the straps 202 (for example, the sixteenth embodiment to the eighteenth embodiment described above), the face shield 1-19 is easier to attach/detach to/from the mask 2, and the distance between the face shield 1-19 and the face is easier to adjust. On the other hand, the face shield 1-19 may be more likely to be displaced or fallen down when in use than in the case in which the looped parts 136 are engaged with the straps 202. In particular, since the face shield 1-19 is supported only by a total of two straps 202, it may be difficult to stably hold and fix the face shield 1-19.

Thus, as described above, the two looped parts 136 are formed away from each other in the left-right direction on one side in the left-right direction of the face shield 1-19, and the upper straps 202 of the mask 2 are inserted through the two looped parts 136. The face shield 1-19 is thereby supported by the upper two straps 202 of the mask 2 at four points. Thus, the face shield 1-19 can be attached/detached to/from the mask 2 more easily while the face shield 1-19 can stably be held by and fixed to the mask 2 when in use. Note that in a case in which the number of the looped parts 136 formed on one side in the left-right direction of the face shield 1-19 is three or more, the face shield 1-19 is supported by the upper two straps 202 of the mask 2 at six or more points when in use, which enables effects similar to those described above to be exerted.

As described above, in the face shield 1-19 according to the nineteenth embodiment, the face shield 1-19 is supported only by the upper two straps 202 of the mask 2, and each of the upper straps 202 is inserted through the two looped parts 136 without being engaged with the looped parts 136. Since this can reduce the area of both the left and right parts of the face shield 1-19 for attaching the mask 2 to the face shield 1-19, the film 101-19 can be reduced in area. Further, the face shield 1-19 can be attached/detached to/from the mask 2 more easily while the face shield 1-19 can stably be held by and fixed to the mask 2 when in use.

As described above, the face shield 1-19 according to the nineteenth embodiment can exert various effects associated with the reduction in area of the film 101-19. For example, since the face shield 1-19 can be reduced in weight, the protective equipment to be worn by the user can be reduced in weight as a whole. This can reduce fatigue of the user, and can also improve a wearing feeling. In addition, it does not appear to be heavy equipment, and people around the user can have a good impression on the appearance. In addition, since the area in which the face shield 1-19 makes contact (is brought into close contact) with the face of the user, for example, can be reduced, the wearing feeling can be improved. In addition, when punching a plurality of the face shields 1-19 from a film in the manufacturing process of the face shield 1-19, for example, the efficiency of the punching (the number to be manufactured per unit area) can be improved. This enables the face shield 1-19 which is less expensive to be provided, can improve productivity, and also facilitates manufacturing.

In addition, the face shield 1-19 according to the nineteenth embodiment eliminates the need to arrange the film 101-19 around the changeable parts 133 (for example, portions on both the sides of the changeable parts 133) as compared with the case in which the looped parts 136 are engaged with the straps 202 (for example, the sixteenth embodiment to the eighteenth embodiment described above). This can improve the degree of freedom in design of the face shield 1-19, and enables a shield shape excellent in design to be designed.

In addition, since the face shield 1-19 according to the nineteenth embodiment enables the looped parts 136 to be relatively moved with respect to the strap 202 in the direction in which the strap 202 is inserted when the strap 202 is inserted through the looped parts 136, the gap between the mask 2 and the face shield 1-19 in the front-back direction can be adjusted. This can prevent the face shield 1-19 from fogging up because of exhaled air of the user, and enables the field of view to be kept well. In addition, glasses worn by the user can be prevented from making contact with the face shield 1-19. Note that since the face shield 1-19 is supported by the upper two straps 202 of the mask 2 at four or more points when in use as described above, the face shield 1-19 can also stably be held by and fixed to the mask 2 when adjusting the gap in the front-back direction between the mask 2 and the face shield 1-19.

In addition, in the face shield 1-19 according to the nineteenth embodiment, the two changeable parts 133 are formed away from each other in the left-right direction on one side in the left-right direction of the face shield 1-19 as described above. Thus, as shown in FIG. 35, a finger notch 137 is formed between the two changeable parts 133 adjacent to each other on one side in the left-right direction of the face shield 1-19. The finger notch 137 is a notch formed between the two changeable parts 133 adjacent to each other so as to extend upward from the lower end of the face shield 1-19. Although the upper end of the finger notch 137 is curved in the example shown in FIG. 35, the shape of the finger notch 137 is not limited to this example, and may be rectangular, for example. A finger of the user is inserted through the finger notch 137. When in use, the user is able to adjust the positional relationship between the face shield 1-19 and the mask 2 more easily by moving his/her finger in a state in which the finger is inserted through the finger notch 137. Note that in the case in which the number of the changeable parts 133 formed on one side in the left-right direction of the face shield 1-19 is three or more, two or more finger notches 137 are formed on the one side in the left-right direction of the face shield 1-19, and effects similar to those described above can be exerted.

In addition, in the face shield 1-19 according to the nineteenth embodiment, a nose notch 138 is formed in the face shield 1-19 at a position to be in contact with the nose of the user as shown in FIG. 35. The nose notch 138 is a notch formed so as to extend upward from the lower end of a central part of the face shield 1-19. Although the nose notch 138 has a curved shape in the example shown in FIG.

35, the shape of the nose notch 138 is not limited to this example, and may be a substantially triangular shape, for example. When the face shield 1-19 is used, the nose of the user fits in the nose notch 138 as shown in FIG. 37. Thus, the face shield 1-19 can be held and fixed more stably in a state in which the face of the user (mainly, the eyes and a region around the eyes) is covered by the face shield 1-19.

Twentieth Embodiment

A face shield 1-20 according to a twentieth embodiment of the present invention will be described with reference to FIGS. 38 and 39.

Figure 38:
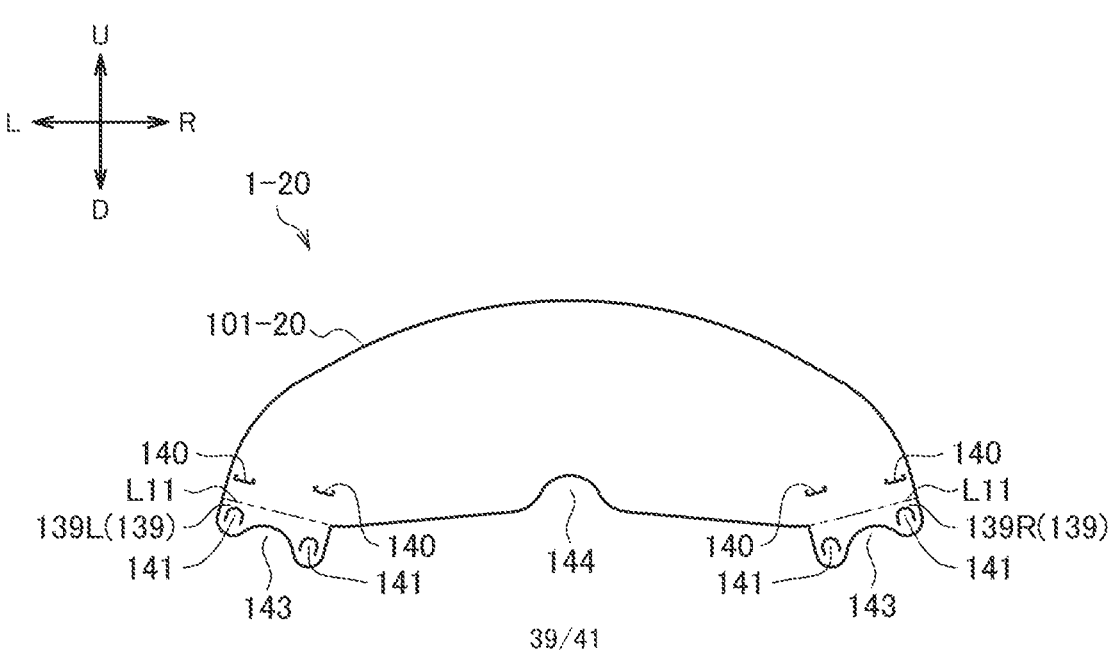
FIG. 38 is a plan view showing a face shield according to a twentieth embodiment of the present invention.

FIG. 38 is a plan view showing the face shield 1-20. FIG. 39 is a schematic view showing states before and after a changeable part 139 (specifically, a changeable part 139L) which will be described later is deformed. Specifically, FIG. 39 is a drawing of the face shield 1-20 as seen from behind (that is, as seen from the user side).

Hereinafter, an example in which the face shield 1-20 is attached to the mask 2 of the ear-hung type will be described as an example. However, the face shield 1-20 according to the twentieth embodiment can also be attached/detached to/from the mask 3 of the tie-string type or the mask 4 of the overhead type besides the mask 2 of the ear-hung type similarly to the face shield 1-19 according to the nineteenth embodiment.

In the face shield 1-20 according to the twentieth embodiment, looped parts 142 (see FIG. 39) formed by the changeable part 139 are not engaged with the strap 202 of the mask 2 similarly to the face shield 1-19 according to the nineteenth embodiment. In other words, when the strap 202 is inserted through the looped parts 142, the looped parts 142 are relatively movable with respect to the strap 202 in the direction in which the strap 202 is inserted. The twentieth embodiment is different from the nineteenth embodiment in that the single changeable part 139 is formed on one side in the left-right direction of the face shield 1-20. However, the twentieth embodiment is common to the nineteenth embodiment in that the number of the looped parts 142 formed on one side in the left-right direction of the face shield 1-20 is two.

As shown in FIG. 38, a pair of the changeable parts 139 (specifically, the changeable parts 139L and 139R) are formed in both left and right parts of the face shield 1-20 (specifically, a film 101-20 that forms the face shield 1-20). The changeable parts 139 are portions of the face shield 1-20 that can be deformed.

The changeable parts 139 are formed so as to extend downward from the face shield 1-20. An outer edge of the changeable parts 139 has a shape protruding downward (for example, a substantially W-shape). However, the shape of the outer edge of the changeable parts 139 is not limited to this example, and may be an arc shape, an oval shape, any curved shape, a rectangular protruding shape, or the like, for example. Each of the changeable parts 139 is foldable upward along a folding line L11 arranged at the base end of each of the changeable parts 139. The length in the left-right direction of the changeable parts 139 is larger than the length in the left-right direction of the changeable parts 133 according to the nineteenth embodiment.

Herein, in the face shield 1-20, two insertion parts 140 are formed away from each other in the left-right direction at positions adjacent to the changeable part 139. The insertion parts 140 are formed of cut lines (specifically, U-shaped closed-type cut lines) similarly to the insertion parts 134 according to the nineteenth embodiment. However, the shape of the insertion parts 140 is not particularly limited similarly to the insertion parts 134 according to the nineteenth embodiment. In addition, two locking claws 141 are formed on the leading end side of the changeable part 139 away from each other in the left-right direction. The locking claws 141 are portions partially cut out along arc-shaped closed-type cut lines which are curved toward the base end side of the changeable part 139 similarly to the locking claws 135 according to the nineteenth embodiment. However, the shape of the locking claws 141 is not particularly limited similarly to the locking claws 135 according to the nineteenth embodiment.

Figure 39:
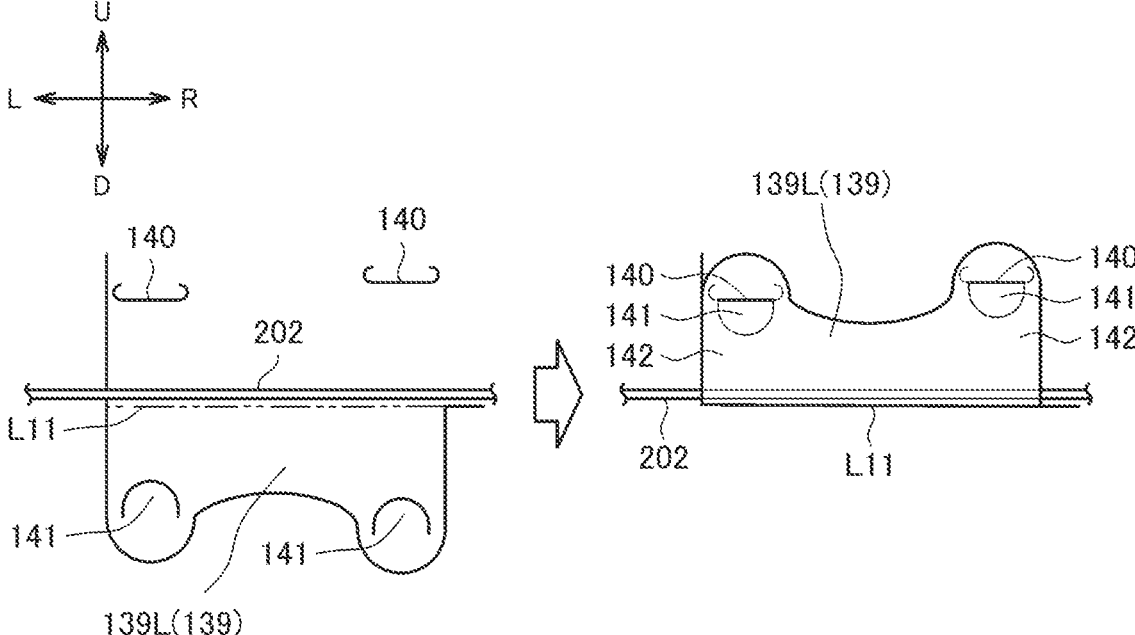
FIG. 39 is a schematic view showing states before and after a changeable part according to the twentieth embodiment of the present invention is deformed.

As shown in FIG. 39, before the changeable part 139 is deformed, the strap 202 of the mask 2 is set in a state passing behind the changeable part 139 (for example, the changeable part 139L) on one side in the left-right direction of the face shield 1-20. The changeable part 139 is folded from this state along the folding line L11 so as to catch the strap 202. The changeable part 139 is locked in the insertion parts 140 with the locking claws 141 in a state in which the changeable part 139 is folded and inserted in the insertion parts 140. Specifically, the locking claw 141 on the outer side (the left side in FIG. 39) is locked in the insertion part 140 on the outer side (the left side in FIG. 39), and the locking claw 141 on the inner side (the right side in FIG. 39) is locked in the insertion part 140 on the inner side (the right side in FIG. 39).

After the changeable part 139 is deformed, looped parts 142 through which the strap 202 of the mask 2 can be inserted are formed by the changeable part 139 having been deformed and the film 101-20 similarly to the sixteenth embodiment to nineteenth embodiment. In the twentieth embodiment, the two looped parts 142 are formed away from each other in the left-right direction by deformation of the single changeable part 139 on one side in the left-right direction of the face shield 1-20. Specifically, the looped part 142 on the outer side (the left side in FIG. 39) is formed by locking of the locking claw 141 on the outer side (the left side in FIG. 39) in the insertion part 140 on the outer side (the left side in FIG. 39). The looped part 142 on the inner side (the right side in FIG. 39) is formed by locking of the locking claw 141 on the inner side (the right side in FIG. 39) in the insertion part 140 on the inner side (the right side in FIG. 39). Note that the shape of the looped parts 142 is not particularly limited similarly to the sixteenth embodiment to nineteenth embodiment.

The upper strap 202 (specifically, the strap 202-1 or the strap 202-3) of the mask 2 is inserted through the two looped parts 142. Specifically, the upper strap 202-1 of the straps 202 extending from the left side of the mask 2 is inserted through the two looped parts 142 formed by the changeable part 139L (that is, the two looped parts 142 formed on the left side of the face shield 1-20). The upper strap 202-3 of the straps 202 extending from the right side of the mask 2 is inserted through the two looped parts 142 formed by the changeable part 139R (that is, the two looped parts 142 formed on the right side of the face shield 1-20). The face shield 1-20 is thereby attached to the mask 2. The face shield 1-20 mainly covers the eyes and a region around the eyes on the face of a user similarly to the face shield 1-19.

Note that in the example shown in FIGS. 38 and 39, the distance between the insertion part 140 and the locking claw 141 on the inner side (the right side in FIG. 39) is wider than the distance between the insertion part 140 and the locking claw 141 on the outer side (the left side in FIG. 39). However, the distance between the insertion part 140 and the locking claw 141 on the inner side (the right side in FIG. 39)

may be narrower than the distance between the insertion part 140 and the locking claw 141 on the outer side (the left side in FIG. 39), or may be equal to that distance. In addition, the number of the insertion parts 140 and the locking claws 141 formed for each of the changeable parts 139 may be three or more. In that case, the number of the looped parts 142 formed on one side in the left-right direction of the face shield 1-20 is three or more. In addition, the number of the insertion parts 140 formed for each of the changeable parts 139 may be smaller than the number of the locking claws 141 formed for each of the changeable parts 139. In addition, the number of the insertion parts 140 and the locking claws 141 formed for the changeable part 139L and the number of the insertion parts 140 and the locking claws 141 formed for the changeable part 139R may be different from each other. In that case, the number of the looped parts 142 formed on the left side of the face shield 1-20 and the number of the looped parts 142 formed on the right side of the face shield 1-20 are different from each other.

As described above, in the face shield 1-20 according to the twentieth embodiment, the face shield 1-20 is supported only by the upper two straps 202 of the mask 2, and each of the upper straps 202 is inserted through the two looped parts 142 without being engaged with the looped parts 142 similarly to the face shield 1-19 according to the nineteenth embodiment described above. This can reduce the area of the film 101-20, and further, the face shield 1-20 can be attached/detached to/from the mask 2 more easily while the face shield 1-20 can stably be held by and fixed to the mask 2 when in use.

In addition, the face shield 1-20 according to the twentieth embodiment is provided with a recessed part 143 formed so as to be recessed upward from a lower end of a central part of the changeable part 139 as shown in FIG. 38. The recessed part 143 is formed between the two locking claws 141 adjacent to each other in the changeable part 139. The area of the film 101-20 can be reduced more effectively by formation of the recessed part 143 in the changeable part 139.

In addition, in the face shield 1-20 according to the twentieth embodiment, a nose notch 144 is formed in the face shield 1-20 at a position to be in contact with the nose of the user as shown in FIG. 38. The position, shape, and installation purpose of the nose notch 144 are similar to those of the nose notch 138 of the face shield 1-19 according to the nineteenth embodiment described above.

Twenty-First Embodiment

A face shield 1-21 according to a twenty-first embodiment of the present invention will be described with reference to FIGS. 40 and 41.

Figure 40:
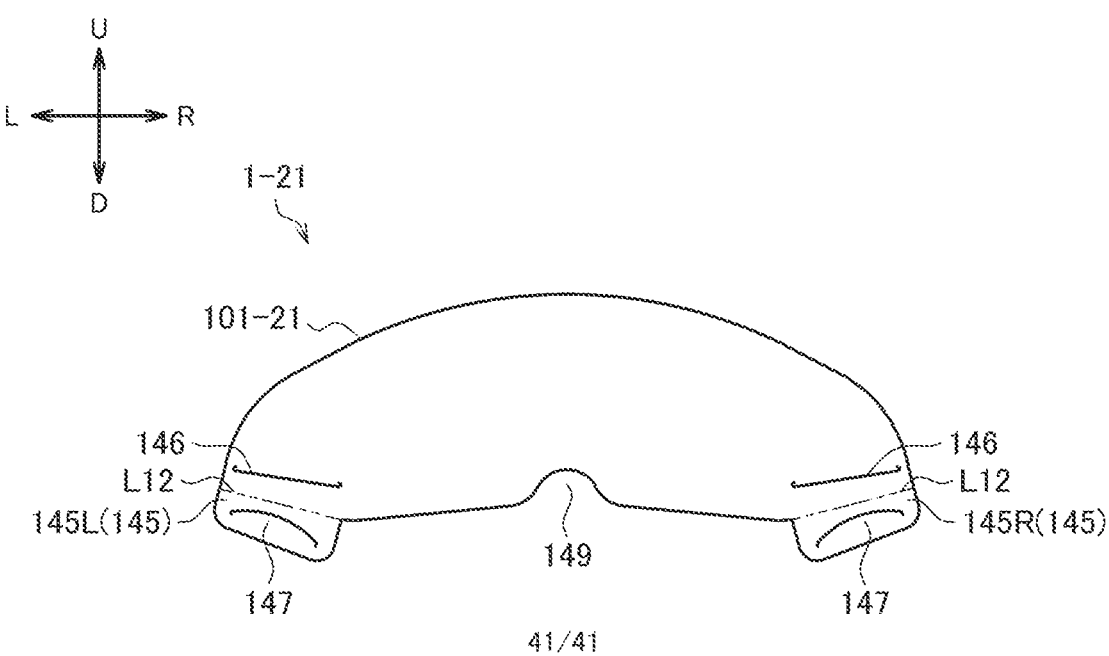
FIG. 40 is a plan view showing a face shield according to a twenty-first embodiment of the present invention.

FIG. 40 is a plan view showing the face shield 1-21. FIG. 41 is a schematic view showing states before and after a changeable part 145 (specifically, a changeable part 145L) which will be described later is deformed. Specifically, FIG. 41 is a drawing of the face shield 1-21 as seen from behind (that is, as seen from the user side).

Hereinafter, an example in which the face shield 1-21 is attached to the mask 2 of the ear-hung type will be described as an example. However, the face shield 1-21 according to the twenty-first embodiment can also be attached/detached to/from the mask 3 of the tie-string type or the mask 4 of the overhead type besides the mask 2 of the ear-hung type similarly to the face shield 1-19 according to the nineteenth embodiment and the face shield 1-20 according to the twentieth embodiment.

In the face shield 1-21 according to the twenty-first embodiment, a looped part 148 (see FIG. 41) formed by the changeable part 145 is not engaged with the strap 202 of the mask 2 similarly to the face shield 1-19 according to the nineteenth embodiment and the face shield 1-20 according to the twentieth embodiment. In other words, when the strap 202 is inserted through the looped part 148, the looped part 148 is relatively movable with respect to the strap 202 in the direction in which the strap 202 is inserted. The twenty-first embodiment is different from the nineteenth embodiment in that the single changeable part 145 is formed on one side in the left-right direction of the face shield 1-21, and in that the single looped part 148 is formed on one side in the left-right direction of the face shield 1-21.

As shown in FIG. 40, a pair of the changeable parts 145 (specifically, changeable parts 145L and 145R) are formed in both left and right parts of the face shield 1-21 (specifically, a film 101-21 that forms the face shield 1-21). The changeable parts 145 are portions of the face shield 1-21 that can be deformed.

The changeable parts 145 are formed so as to extend downward from the face shield 1-21. An outer edge of the changeable parts 145 has a shape protruding downward (for example, a substantially U-shape). However, the shape of the outer edge of the changeable parts 145 is not limited to this example, and may be an arc shape, an oval shape, any curved shape, a rectangular protruding shape, or the like, for example. Each of the changeable parts 145 is foldable upward along a folding line L12 arranged at a base end of each of the changeable parts 145. The length in the left-right direction of the changeable parts 145 is longer than the length in the left-right direction of the changeable parts 133 according to the nineteenth embodiment.

A single insertion part 146 in which the changeable part 145 can be inserted is formed in the face shield 1-21 at a position adjacent to the changeable part 145. In addition, a single locking claw 147 that locks the changeable part 145 in the insertion part 146 is formed on a leading end side of the changeable part 145. However, the shapes of the insertion part 146 and the locking claw 147 are not particularly limited similarly to the nineteenth embodiment. Herein, the lengths in the left-right direction of the insertion part 146 and the locking claw 147 are longer than the lengths in the left-right direction of the insertion part 134 and the locking claw 135 according to the nineteenth embodiment.

Figure 41:
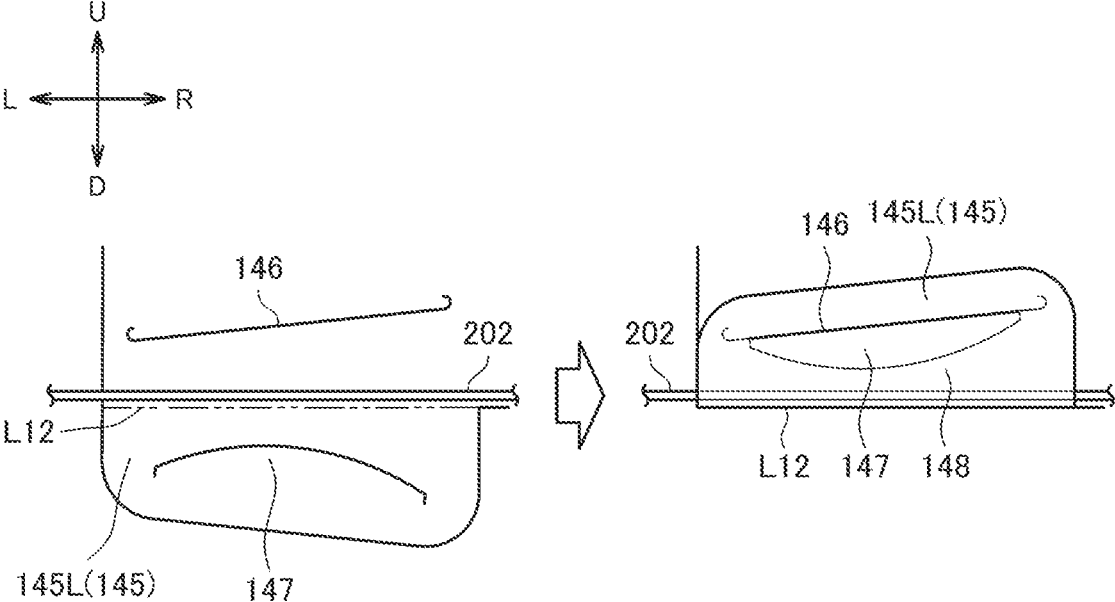
FIG. 41 is a schematic view showing states before and after a changeable part according to the twenty-first embodiment of the present invention is deformed.

As shown in FIG. 41, before the changeable part 145 is deformed, the strap 202 of the mask 2 is set in a state passing behind the changeable part 145 (for example, the changeable part 145L) on one side in the left-right direction of the face shield 1-21. The changeable part 145 is folded from this state along the folding line L12 so as to catch the strap 202. The changeable part 145 is locked in the insertion part 146 with the locking claw 147 in a state in which the changeable part 145 is folded and inserted in the insertion part 146. After the changeable part 145 is deformed, a looped part 148 through which the strap 202 of the mask 2 can be inserted is formed by the changeable part 145 having been deformed and the film 101-21 similarly to the sixteenth embodiment to the twentieth embodiment. The upper strap 202 of the mask 2 (specifically, the strap 202-1 or the strap 202-3) is inserted through the looped part 148. Note that the shape of the looped part 148 is not particularly limited similarly to the sixteenth embodiment to the twentieth embodiment.

Specifically, the upper strap 202-1 of the straps 202 extending from the left side of the mask 2 is inserted through the single looped part 148 formed by the changeable part 145L (that is, the single looped part 148 formed on the left side of the face shield 1-21). The upper strap 202-3 of the straps 202 extending from the right side of the mask 2 is inserted through the single looped part 148 formed by the changeable part 145R (that is, the single looped part 148 formed on the right side of the face shield 1-21). The face shield 1-21 is thereby attached to the mask 2. The face shield 1-21 mainly covers the eyes and a region around the eyes on the face of a user similarly to the face shield 1-19 and the face shield 1-20.

Note that in the example shown in FIGS. 40 and 41, the distance between the insertion part 146 and the locking claw 147 on the inner side (the right side in FIG. 41) is wider than the distance between the insertion part 146 and the locking claw 147 on the outer side (the left side in FIG. 41). However, the distance between the insertion part 146 and the locking claw 147 on the inner side (the right side in FIG. 41) may be narrower than or equal to the distance between the insertion part 146 and the locking claw 147 on the outer side (the left side in FIG. 41).

As described above, in the face shield 1-21 according to the twenty-first embodiment, the number of the looped parts 148 formed on one side in the left-right direction of the face shield 1-21 is not two but one unlike the face shield 1-19 according to the nineteenth embodiment described above. Thus, the face shield 1-21 is supported by the upper two straps 202 of the mask 2 at two points.

Herein, the looped part 148 is formed by locking of the locking claw 147 in the insertion part 146. The lengths in the left-right direction of the locking claw 147 and the insertion part 146 are longer than the lengths in the left-right direction of the locking claw 135 and the insertion part 134 in the face shield 1-19, as described above. Thus, the length in the left-right direction of the looped part 148 is longer than the length in the left-right direction of the looped part 136 in the face shield 1-19 described above. For example, the length in the left-right direction of the looped part 148 is more than or equal to 20 mm.

Thus, in the face shield 1-21, the face shield 1-21 is supported by the upper two straps 202 of the mask 2 at two points, but the somewhat long length in the left-right direction of the looped parts 148 enables the face shield 1-21 to stably be held by and fixed to the mask 2 when in use. Therefore, the face shield 1-21 according to the twenty-first embodiment enables the area of the film 101-21 to be reduced similarly to the face shield 1-19 according to the nineteenth embodiment described above, and further, the face shield 1-21 can be attached/detached to/from the mask 2 more easily while the face shield 1-21 can stably be held by and fixed to the mask 2 when in use.

In addition, in the face shield 1-21 according to the twenty-first embodiment, a nose notch 149 is formed in the face shield 1-21 at a position to be in contact with the nose of the user as shown in FIG. 40. The position, shape, and installation purpose of the nose notch 149 are similar to those of the nose notch 138 of the face shield 1-19 according to the nineteenth embodiment described above.

The embodiments of the present invention have been described above with reference to the drawings, whilst it goes without saying that the present invention is not limited to such embodiments. It is apparent that a person skilled in the art may find various alterations and modifications within the scope of the appended claims, and it should be understood that they will naturally come under the technical scope of the present invention Although the masks 2, 3, and 4 have been described above as masks to which the face shields according to the respective embodiments are attached, the masks are not limited to the above-described examples. For example, masks to which the face shields according to the respective embodiments are attached may have various materials, various dimensions, and various shapes.

In addition, the respective embodiments described above may be combined as appropriate.

In the second embodiment to the twelfth embodiment, for example, the cut line 102 is used as the mechanism through which straps of the masks are to be inserted and which is engaged with the straps. However, the cut line 102 in the second embodiment to the twelfth embodiment may be replaced by the cut line 113 according to the thirteenth embodiment, the cut line 114 according to the fourteenth embodiment, the cut line 115 according to the fifteenth embodiment, the changeable part 116 according to the sixteenth embodiment, the changeable part 121 according to the seventeenth embodiment, the changeable part 127 according to the eighteenth embodiment, the changeable part 133 according to the nineteenth embodiment, the changeable part 139 according to the twentieth embodiment, or the changeable part 145 according to the twenty-first embodiment. In addition, the mechanism to be engaged with the straps in the second embodiment to the twelfth embodiment may be provided in a plurality of pairs as in the eleventh embodiment and the twelfth embodiment.

In addition, for example, in each of the embodiments, all or part of the notch 103 according to the second embodiment, the through-holes 104 according to the third embodiment, the folding part 105 according to the fourth embodiment, the folding part 107 according to the fifth embodiment, the folding lines L3 and L4 according to the sixth embodiment, the antireflection layer 109 according to the seventh embodiment, the through-hole 111 according to the eighth embodiment, the mark according to the ninth embodiment, and the formative structure 112 according to the tenth embodiment may additionally be provided.

REFERENCE SIGNS LIST

1-1 to 1-21 face shield
2, 3, 4 mask
101-1 to 101-21 film
102 cut line
102a, 102b engagement part
103 notch
104 through-hole
105 folding part
107 folding part
109 antireflection layer
110 base layer
111 through-hole
112 formative structure
113 cut line
113a, 113b engagement part
114 cut line
114a, 114b engagement part
115 cut line
115a engagement part
116 changeable part
118 insertion part
119 locking claw
120 looped part
121 changeable part
123 insertion part
124 locking claw
125 looped part
126 notch
127 changeable part
129 insertion part
130 locking claw
131 looped part
132 formative structure
133 changeable part
134 insertion part
135 locking claw
136 looped part
137 finger notch
138 nose notch
139 changeable part
140 insertion part
141 locking claw
142 looped part
143 recessed part
144 nose notch
145 changeable part
146 insertion part
147 locking claw
148 looped part
149 nose notch
202 strap
302 strap
402 strap
L1 to L12 folding line

The invention claimed is:

1. A face shield that is attachable/detachable to/from a mask, and is configured to cover at least an eye of a face of a user who wears the mask, wherein the face shield is made of a film having flexibility and translucency, at least a pair of changeable parts that can be deformed are formed in both left and right parts of the face shield, and closed looped parts through which straps of the mask can be inserted are formed by deformation of the changeable parts, wherein two or more of the closed looped parts are formed away from each other in the left-right direction by deformation of the changeable parts on one side in the left-right direction of the face shield, and an upper one of the straps of the mask is inserted through the two or more of the closed looped parts, wherein insertion parts formed of cut lines are formed in the face shield at positions adjacent to the changeable parts, the closed looped parts are formed by insertion of the changeable parts in the insertion parts, the changeable parts are formed so as to extend downward from both the left and right parts of the face shield and are foldable upward, and the insertion parts are formed above the changeable parts.

2. The face shield according to claim 1, wherein the changeable parts can be deformed by being partially cut out along cut lines formed in the face shield, and the closed looped parts are engaged with the straps inserted through the closed looped parts.

3. The face shield according to claim 1, wherein two or more of the changeable parts are formed away from each other in the left-right direction on one side in the left-right direction of the face shield, and the two or more of the closed looped parts are formed by deformation of the two or more of the changeable parts.

4. The face shield according to claim 1, wherein when the upper one of the straps of the mask is inserted through the two or more of the closed looped parts, the closed looped parts are relatively movable with respect to the strap in a direction through which the strap is inserted.

5. The face shield according to claim 1, wherein locking claws that lock the changeable parts in the insertion parts are formed in the changeable parts.

* * * * *